US010729664B2

(12) United States Patent
Woolf et al.

(10) Patent No.: US 10,729,664 B2
(45) Date of Patent: Aug. 4, 2020

(54) PERMANENTLY CHARGED SODIUM AND CALCIUM CHANNEL BLOCKERS AS ANTI-INFLAMMATORY AGENTS

(71) Applicants: Children's Medical Center Corporation, Boston, MA (US); President and Fellows of Harvard College, Cambridge, MA (US)

(72) Inventors: Clifford J. Woolf, Newton, MA (US); Bruce P. Bean, Cambridge, MA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/216,489

(22) Filed: Dec. 11, 2018

(65) Prior Publication Data

US 2019/0216747 A1 Jul. 18, 2019

Related U.S. Application Data

(62) Division of application No. 13/382,834, filed as application No. PCT/US2010/041537 on Jul. 9, 2010, now abandoned.

(60) Provisional application No. 61/224,512, filed on Jul. 10, 2009.

(51) Int. Cl.
| | |
|---|---|
| *A61K 31/00* | (2006.01) |
| *A61K 31/165* | (2006.01) |
| *A61K 31/167* | (2006.01) |
| *A61K 31/277* | (2006.01) |
| *A61K 45/06* | (2006.01) |
| *C07D 235/14* | (2006.01) |
| *C07D 295/192* | (2006.01) |

(52) U.S. Cl.
CPC ............ *A61K 31/00* (2013.01); *A61K 31/165* (2013.01); *A61K 31/167* (2013.01); *A61K 31/277* (2013.01); *A61K 45/06* (2013.01); *C07D 235/14* (2013.01); *C07D 295/192* (2013.01)

(58) Field of Classification Search
None
See application file for complete search history.

(56) References Cited

U.S. PATENT DOCUMENTS

| | | |
|---|---|---|
| 812,554 A | 2/1906 | Einhorn |
| 1,889,645 A | 11/1932 | Otto |
| 2,441,498 A | 5/1948 | Loefgren et al. |
| 2,689,248 A | 9/1954 | Clinton et al. |
| 2,799,679 A | 7/1957 | Thuresson et al. |
| 2,955,111 A | 10/1960 | Thuresson et al. |
| 3,160,662 A | 12/1964 | Magnus et al. |
| 3,177,252 A | 4/1965 | Leon |
| 3,519,631 A | 7/1970 | Jerchel et al. |
| 3,773,939 A | 11/1973 | Janssen |
| 3,812,147 A | 5/1974 | Adams et al. |
| 3,900,481 A | 8/1975 | Banitt et al. |
| 3,931,195 A | 1/1976 | Dykstra et al. |
| 4,069,309 A | 1/1978 | Ciaudelli et al. |
| 4,070,347 A | 1/1978 | Schmitt |
| 4,293,539 A | 10/1981 | Ludwig et al. |
| 4,757,128 A | 7/1988 | Domb et al. |
| 4,877,805 A | 10/1989 | Kligman |
| 4,975,282 A | 12/1990 | Cullis et al. |
| 4,980,378 A | 12/1990 | Wong et al. |
| 4,994,213 A | 2/1991 | Aitcheson et al. |
| 5,000,958 A | 3/1991 | Fountain et al. |
| 5,023,087 A | 6/1991 | Yau-Young |
| 5,032,582 A | 7/1991 | Abra |
| 5,049,388 A | 9/1991 | Knight et al. |
| 5,082,866 A | 1/1992 | Wong et al. |
| 5,169,637 A | 12/1992 | Lenk et al. |
| 5,176,907 A | 1/1993 | Leong |
| 5,194,266 A | 3/1993 | Abra et al. |
| 5,194,581 A | 3/1993 | Leong |
| 5,356,633 A | 10/1994 | Woodle et al. |
| 5,409,704 A | 4/1995 | Bally et al. |
| 5,480,971 A | 1/1996 | Houghten et al. |
| 5,552,155 A | 6/1996 | Jones |
| 5,591,317 A | 1/1997 | Pitts, Jr. |
| 5,688,525 A | 11/1997 | Adler-Moore et al. |
| 5,747,470 A | 5/1998 | Becherer et al. |
| 5,783,683 A | 7/1998 | Morrison |
| 5,874,104 A | 2/1999 | Adler-Moore et al. |
| 5,883,228 A | 3/1999 | Darnell, Jr. et al. |
| 5,952,451 A | 9/1999 | Zhao |
| 6,008,318 A | 12/1999 | Zhao |

(Continued)

FOREIGN PATENT DOCUMENTS

| | | |
|---|---|---|
| CA | 982148 | 1/1976 |
| CA | 2 717 042 A1 | 9/2009 |

(Continued)

OTHER PUBLICATIONS

Anger et al. "Medicinal Chemistry of Neuronal Voltage-Gated Sodium Channel Blockers," J. Med. Chem. 2001; 44:2 (115-137). (Year: 2001).*
Extended European Search Report in connection with Patent Application No. 10797919.7, dated Oct. 29, 2012.
Extended European Search Report in connection with Patent Application No. 15002768.8, dated Nov. 24, 2015.
Extended European Search Report in connection with Patent Application No. 18211462.9, dated Apr. 23, 2019.
International Search Report and Written Opinion of International Application No. PCT/US2010/41537, dated Oct. 18, 2010.
International Preliminary Report on Patentability and Written Opinion for International Application No. PCT/US2010/041537, dated Jan. 10, 2012.

(Continued)

*Primary Examiner* — Jeffrey S Lundgren
*Assistant Examiner* — Michael J Schmitt
(74) *Attorney, Agent, or Firm* — Wolf, Greenfield & Sacks, P.C.

(57) ABSTRACT

The invention provides compounds, compositions, methods, and kits for the treatment of neurogenic inflammation.

25 Claims, 2 Drawing Sheets

(56) References Cited

U.S. PATENT DOCUMENTS

| | | |
|---|---|---|
| 6,051,576 A | 4/2000 | Ashton et al. |
| 6,083,996 A | 7/2000 | Buyuktimkin et al. |
| 6,103,255 A | 8/2000 | Levene |
| 6,118,020 A | 9/2000 | Buyuktimkin et al. |
| 6,153,212 A | 11/2000 | Mao et al. |
| 6,355,637 B1 | 3/2002 | Axt et al. |
| 6,362,197 B1 | 3/2002 | Page et al. |
| 6,413,961 B1 | 7/2002 | Demopulos et al. |
| 6,432,937 B1 | 8/2002 | Hallgren |
| 6,623,040 B1 | 9/2003 | Foley et al. |
| 6,709,406 B2 | 3/2004 | Laserow |
| 6,766,319 B1 | 7/2004 | Might |
| 6,825,190 B2 | 11/2004 | Moon et al. |
| 6,884,782 B2 | 4/2005 | Huang et al. |
| 7,166,590 B2 | 1/2007 | Seko et al. |
| 7,429,673 B2 | 9/2008 | Morazzoni et al. |
| 7,446,226 B2 | 11/2008 | Helsing et al. |
| 7,705,004 B2 | 4/2010 | Song et al. |
| 8,138,339 B2 | 3/2012 | Bauer et al. |
| 8,143,412 B2 | 3/2012 | Priebe et al. |
| 8,258,144 B2 | 9/2012 | Song et al. |
| 8,822,537 B2 | 9/2014 | Buyuktimkin et al. |
| 9,603,817 B2 | 3/2017 | Bean et al. |
| 10,179,116 B2 | 1/2019 | Bean et al. |
| 2003/0105126 A1 | 6/2003 | Demopulos et al. |
| 2003/0152637 A1 | 8/2003 | Chasin et al. |
| 2003/0166629 A1 | 9/2003 | Choi et al. |
| 2004/0146590 A1 | 7/2004 | Iadarola et al. |
| 2004/0220187 A1 | 11/2004 | Stephenson et al. |
| 2004/0266870 A1 | 12/2004 | Allegretti et al. |
| 2005/0009016 A1 | 1/2005 | Moskowitz et al. |
| 2005/0025765 A1 | 2/2005 | DiMauro et al. |
| 2005/0090557 A1 | 4/2005 | Muhammad et al. |
| 2005/0142596 A1 | 6/2005 | Krolewski et al. |
| 2005/0152957 A1 | 7/2005 | Cleary et al. |
| 2005/0233398 A1 | 10/2005 | Chu et al. |
| 2005/0277680 A1 | 12/2005 | Priebe et al. |
| 2006/0062739 A1 | 3/2006 | Hofmann et al. |
| 2006/0100272 A1 | 5/2006 | Maniar |
| 2006/0106020 A1 | 5/2006 | Rodgers et al. |
| 2006/0134008 A1 | 6/2006 | Deaver |
| 2006/0183906 A1 | 8/2006 | Rodgers et al. |
| 2007/0135461 A1 | 6/2007 | Rodgers et al. |
| 2007/0149469 A1 | 6/2007 | Korherr |
| 2007/0149506 A1 | 6/2007 | Arvanitis et al. |
| 2008/0188500 A1 | 8/2008 | Arvanitis et al. |
| 2008/0312212 A1 | 12/2008 | Collingwood et al. |
| 2009/0054485 A1 | 2/2009 | Gleich et al. |
| 2009/0060898 A1 | 3/2009 | Kandimalla et al. |
| 2009/0162333 A1 | 6/2009 | Pays et al. |
| 2010/0098685 A1 | 4/2010 | Zhu et al. |
| 2010/0099772 A1 | 4/2010 | Bean et al. |
| 2010/0113416 A1 | 5/2010 | Friedman et al. |
| 2010/0120781 A1 | 5/2010 | Neamati |
| 2011/0086818 A1 | 4/2011 | Bean et al. |
| 2012/0022142 A1 | 1/2012 | Jadhav et al. |
| 2012/0129867 A1 | 5/2012 | Bauer et al. |
| 2012/0172429 A1 | 7/2012 | Woolf et al. |
| 2012/0195902 A1 | 8/2012 | Friedman et al. |
| 2015/0087714 A1 | 3/2015 | Bean et al. |
| 2017/0319517 A1 | 11/2017 | Bean et al. |
| 2018/0237392 A1 | 8/2018 | Bean et al. |

FOREIGN PATENT DOCUMENTS

| | | |
|---|---|---|
| CN | 101156851 A | 4/2008 |
| CN | 101347427 A | 1/2009 |
| DE | 2 162 744 | 7/1972 |
| DE | 2 235 745 A1 | 2/1973 |
| DE | 2657728 A1 | 7/1977 |
| DE | 2915250 A1 | 10/1980 |
| DE | 150423 A1 | 9/1981 |
| DE | 151036 A1 | 9/1981 |
| DE | 100 39 449 A1 | 7/2003 |
| EP | 0586106 A1 | 3/1994 |
| JP | 2001-513106 | 8/2001 |
| JP | 2003-516966 | 5/2003 |
| JP | 2006-522832 A | 10/2006 |
| JP | 2008-514648 | 5/2008 |
| JP | 2009-520700 A | 5/2009 |
| JP | 6205133 B2 | 9/2017 |
| WO | WO 1985/00599 A1 | 2/1985 |
| WO | WO 1996/40061 A1 | 12/1996 |
| WO | WO 1998/24428 A1 | 6/1998 |
| WO | WO 1998/37896 A1 | 9/1998 |
| WO | WO 1999/11252 A2 | 3/1999 |
| WO | WO 1999/63985 A1 | 12/1999 |
| WO | WO 2001/44192 A1 | 6/2001 |
| WO | WO 2001/44218 A1 | 6/2001 |
| WO | WO 2001/45678 A2 | 6/2001 |
| WO | WO 2004/012757 A2 | 2/2004 |
| WO | WO 2004/110423 A1 | 12/2004 |
| WO | WO 2005/089206 A2 | 9/2005 |
| WO | WO 2005/117981 A1 | 12/2005 |
| WO | WO 2006/010587 A1 | 2/2006 |
| WO | WO 2006/065722 A2 | 6/2006 |
| WO | WO 2007/071055 A1 | 6/2007 |
| WO | WO 2008/063603 A | 5/2008 |
| WO | WO 2009/114139 A2 | 9/2009 |
| WO | WO 2010/017996 A1 | 2/2010 |
| WO | WO 2011/006073 A1 | 1/2011 |
| WO | WO 2011/133474 A2 | 10/2011 |
| WO | WO 2012/030912 A1 | 3/2012 |
| WO | WO 2012/162394 A2 | 11/2012 |
| WO | WO 2017/024037 A1 | 2/2017 |

OTHER PUBLICATIONS

[No Author Listed] NCBI Blast for Accession No. AAI42721.1. Retrieved on Jun. 9, 2015 (2 pages).

[No Author Listed] NCBI Blast for Accession No. AAI43039.1. Retrieved on Jun. 9, 2015 (2 pages).

[No Author Listed] NCBI Blast for Accession No. AF305224.1. Retrieved on Jun. 9, 2015 (2 pages).

[No Author Listed] NCBI Blast for Accession No. BC127186.1. Retrieved on Jun. 9, 2015 (3 pages).

[No Author Listed] NCBI Blast for Accession No. CAQ09089.1. Retrieved on Jun. 9, 2015 (2 pages).

[No Author Listed] NCBI Blast for Accession No. NC_000022.10. Retrieved on Jun. 9, 2015 (2 pages).

[No Author Listed] NCBI Blast for Accession No. NM_001136540.1. Retrieved on Jun. 9, 2015 (5 pages).

[No Author Listed] NCBI Blast for Accession No. NM_003661.3. Retrieved on Jun. 9, 2015 (5 pages).

[No Author Listed] NCBI Blast for Accession No. NM_145343.2. Retrieved on Jun. 9, 2015 (5 pages).

[No Author Listed] NCBI Blast for Accession No. NP_003652.2. Retrieved on Jun. 9, 2015 (3 pages).

[No Author Listed] NCBI Blast for Accession No. Z82215.1. Retrieved on Jun. 9, 2015 (31 pages).

[No Author Listed] NCBI Reference SNP(refSNP) Cluster Report: rs60910145, <http://www.ncbi.nlm.nih.gov/projects/SNP/snp_ref.cgi?rs=60910145>, retrieved on Dec. 15, 2011 (3 pages).

[No Author Listed] NCBI Reference SNP(refSNP) Cluster Report: rs73885319, <http://www.ncbi.nlm.nih.gov/projects/SNP/snp_ref.cgi?rs=73885319>, retrieved Dec. 15, 2011 (3 pages).

[No Author Listed] PubChem. Compound Summary: N-(2,6-Dimethylphenyl)-2-(1-ethylpiperidin-1-ium-1-yl)butanamide. CID: 126520527. Created Apr. 22, 2017. 9 pages.

Adams et al., The Bcl-2-regulated apoptosis switch: mechanism and therapeutic potential, available in PMC Sep. 29, 2009, published in final edited form as: Curr Opin Immunol. 2007;19(5):488-96(14 pages).

Allen et al., Clinical relevance of the neurotrophins and their receptors, Clin Sci (Lond). 2006;110(2):175-91.

Amir et al., The role of sodium channels in chronic inflammatory and neuropathic pain, J Pain. 2006; 7(5 Suppl 3):S1-29.

Anderson et al., The process of structure-based drug design. Chem Biol. Sep. 2003;10(9):787-97.

(56) References Cited

OTHER PUBLICATIONS

Andre et al., Transient receptor potential ankyrin receptor 1 is a novel target for pro-tussive agents. Br J Pharmacol. Nov. 2009; 158(6):1621-8.

Anger et al., Medicinal chemistry of neuronal voltage-gated sodium channel blockers, J. Med. Chem. 2001; 44(2):115-137.

Appel et al., Intensive blood-pressure control in hypertensive chronic kidney disease, N Engl J Med. 2010; 363(10): 918-29.

Aracava et al., Interactions of bupivacaine with ionic channels of the nicotinic receptor. Analysis of single-channel currents. Molecular Pharmacology. 1984; 26(2): 304-13.

Bautista et al., Fire in the hole: pore dilation of the capsaicin receptor TRPV1, Nat Neurosci. 2008;11(5):528-9.

Bentley et al., Variation in APOL1 Contributes to Ancestry-Level Differences in HDLc-Kidney Function Association, Int J Nephrol. 2012; 748984 (10 pages).

Berge et al., Pharmaceutical salts. J. Pharmaceutical Sciences 1977; 66(1):1-19.

Bernatowicz et al., 1H-Pyrazole-1-carboxamidine hydrochloride an attractive reagent for guanylation of amines and its application to peptide synthesis. J Org Chem. Apr. 1992 ;57(8):2497-2502.

Bernatowicz et al., Urethane protected derivatives of 1-guanylpyrazole for the mild and efficient preparation of guanidines. Tetrahderon Lett.May 1993;34(21):3389-3392.

Bessac et al., Breathtaking TRP channels: TRPA1 and TRPV1 in airway chemosensation and reflex control, Available in PMC Dec. 1, 2009, published in final edited form as: Physiology (Bethesda). 23:360-70 (2008) (20 pages).

Binshitok et al., Inhibition of nociceptors by TRPV-1 mediated entry of impermeant sodium channel blockers, Nature. 449(7162):607-10 (2007).

Binshtok et al., Coapplication of lidocaine and the permanently charged sodium channel blocker QX-314 produces a long-lasting nociceptive blockade in rodents. Anesthesiology, 2009; 111(1):127-37.

Binshtok et al., Lidocaine targets entry of the impermeant sodium channel blocker QX-314 into nociceptors to produce long-lasting regional analgesia, Program No. 170.6./KK27 2008 Neuroscience Meeting Planner. Washington, D.C.: Society for Neuroscience, 2008 (1 page). Online.

Birklein et al., Neuropeptides, neurogenic inflammation and complex regional pain syndrome (CRPS), Neurosci Lett. 2008; 437:199-202.

Birrell et al., TRPA1 Agonists Evoke Coughing in Guinea-pig and Human Volunteers. Am J Respir Crit Care Med. Dec. 1, 2009; 180(11):1042-7.

Bley et al., Extracellular application of QX-314 blocks sodium channels and causes local anesthesia, Soc Neurosci. 1995; 21:1820 (Abstract 716.7).

Bley, Recent developments in transient receptor potential vanilloid receptor 1 agonist-based therapies, Expert Opin Investig Drugs. 2004; 13(11):1445-56.

Blumberg, Lighting a backfire to quench the blaze: A combined drug approach targeting the vanilloid receptor TRPV1, Molecular Interventions. 2007; 7:310-312.

Bochner et al., Immunological aspects of allergic asthma, Annu. Rev. Immunol. 1994; 12:295-335.

Bonjardim et al., Nociceptive behavior induced by mustard oil injection into the temporomandibular joint is blocked by a peripheral non-opioid analgesic and a central opioid analgesic, Pharmacol Biochem Behav. 2009; 91:321-326.

Breznan et al., The lipid composition of high-density lipoprotein affects its re-absorption in the kidney by proximal tubule epithelial cells, Biochem J. 2004; 379(Pt 2):343-9.

Brill, Esters of Aminobenzoic Acids. J. Am. Chem. Soc. 1921; 43(6):1320-1323.

Caceres et al., A sensory neuronal ion channel essential for airway inflammation and hyperreactivity in asthma, Proc Natl Acad Sci U S A. 2009; 106(22):9099-104.

Cahalan et al., Interactions between quaternary lidocaine, the sodium channel gates, and tetrodotoxin, Biophys J. 1979; 27(1):39-55.

Cao, Voltage-gated calcium channels and pain, Pain. 2006; 126(1-3):5-9.

Carr, Neuroimmunology: Adding insult to allergy, Nat Rev Neurosci. 2015;16(8):444.

Chen et al., Differential Blockade of Nerve Injury-induced Thermal and Tactile Hypersensitivity by Systemically Administered Brain-penetrating and Peripherally Restricted Local Anesthetics, J. Pain. 2004;5:281-289.

Chiu et al., Bacteria activate sensory neurons that modulate pain and inflammation. Nature. Sep. 5, 2013; 501(7465):52-7. doi: 10.1038/nature12479. Epub Aug. 21, 2013.

Clare et al., Voltage-gated sodium channels as therapeutic targets, Drug Discovery Today. 2000;5(11):506-520.

Clark et al., Derivatives of 3:4-xylidine and related compounds as inhibitors of influenza virus: relationships between chemical structure and biological activity. Br J Pharmacol Chemother. Dec. 1958;13(4):424-35.

Clinton et al., Derivatives of 4-Amino-2-hydroxybenzoic Acid. II. J Am. Chem. Soc. 1952; 74(3):592-598.

Creveling et al., Batrachotoxin-induced depolarization and [3H]batrachotoxinin-A 20α-benzoate binding in a vesicular preparation from guinea pig cerebral cortex: inhibition by local anesthetics. Molecular Pharmacology. 1983; 23(2), 350-8.

Curtis et al., The Mechanism of Action of Local Anesthesia by Tetraethylammonium Derivatives, Anesthesiology. 1981; 54:270-277.

D'Agati et al., Focal segmental glomerulosclerosis, N Engl J Med. 2011; 365(25):2398-411.

Donner et al., New Generation Anticonvulsants for the Treatment of Epilepsy in Children, NeuroRx: The Journal of the American Society for Experimental NeuroTherapeutics. 2006; 3:170-180.

Duchateau et al., Apolipoprotein L, a new human high density lipoprotein apolipoprotein expressed by the pancreas. Identification, cloning, characterization, and plasma distribution of apolipoprotein L, J Biol Chem. 1997; 272(41):25576-82.

Dux et al., Inhibition of the neurogenic inflammatory response by lidocaine in rat skin, Inflamm Res. 1996; 45(1):10-3.

Edmondstone, Chest pain and non-respiratory symptoms in acute asthma, Postgrad Med J. 2000; 76(897):413-414.

Eller et al., High affinity interaction of mibefradil with voltage-gated calcium and sodium channels, British Journal of Pharmacology. 2000; 130(3):669-677.

Ferrarelli, Allergic sensations fuel asthma, Sci Signal. 2015; 8(387):ec201.

Field et al., Identification of the alpha2-delta-1 subunit of voltage-dependent calcium channels as a molecular target for pain mediating the analgesic actions of pregabalin, Proc Natl Acad Sci USA. 2006;103 (46):17537-42.

Fishman et al., Intravenous Lidocaine for Treatment-resistant Pruritus, Am J Med. 1997; 102(6):584-585.

Fourneau et al., Stereoisomerism and local anesthetic action. Bull. Sci. Pharmacol. 1928; 35:273.

Frazier et al., The site of action and active form of local anesthetics. II. Experiments with quaternary compounds, J. Pharmacol. Exp. Ther. 1970; 171:45-51.

Freedman et al., The apolipoprotein L1 (APOL1) gene and nondiabetic nephropathy in African Americans, J Am Soc Nephrol. 2010; 21(9):1422-6 (5 pages).

Gennaro, Remington: The Science and Practice of Pharmacy, 19th edition, 1995, Lippincott Williams & Wilkins, Philadelphia.

Genovese et al., Association of trypanolytic ApoL1 variants with kidney disease in African Americans, Science. 2010; 329(5993):841-5.

Gentry et al., Local Anesthetics Noncompetitively Inhibit Function of Four Distinct Nicotinic Acetylcholine Receptor Subtypes, J Pharmacol Exp Ther. 2001; 299(3):1038-48.

Geppetti et al., The concept of neurogenic inflammation. BJU Int. Mar. 2008; 101 Suppl 3:2-6.

Geppetti et al., The transient receptor potential vanilloid 1: role in airway inflammation and disease, Eur J Pharmacol. 2006; 533(1-3):207-14.

(56) References Cited

OTHER PUBLICATIONS

Gerner et al., Capsaicin Combined with Local Anesthetics Preferentially Prolongs Sensory/Nociceptive Block in Rat Sciatic Nerve, Anesthesiology. 2008; 109:872-878.
Gerner et al., Spinal Tonicaine: Potency and Differential Blockade of Sensory and Motor Functions, Anesthesiology. 2000; 92:1350-1360.
Gibson et al., The human serum resistance associated gene is ubiquitous and conserved in Trypanosoma brucei rhodesiense throughout East Africa, Infect Genet Evol. 2002; 1(3):207-14.
Grantham et al., Fluspirilene Block of N-Type Calcium Current in NGF-Differentiated PC12 Cells, Br. J. Pharmacol. 1994; 111:483-488.
Green, Gastrin-releasing peptide, substance P and cytokines in rheumatoid arthritis. Arthritis Res. Ther. 2005; 7(3):111-3.
Gribkoff, The Role of Voltage-Gated Calcium Channels in Pain and Nociception, Semin. Cell Dev. Biol. 2006; 17:555-564.
Gribkoff, Voltage-gated sodium channels in spinal ganglia: Tempting targets for new pain medications, Drug Discov Today. 2006; 3(4):585-91.
Gross et al., Role of neuropeptides in inflammatory bowel disease. Inflamm Bowel Dis 2007; 13(7):918-32.
Guy, Neurogenic Factors in Contact Dermatitis. AMA Arch Derm Syphilol. 1952; 66(1):1-8.
Hahn et al., Neuromyotonia in hereditary motor neuropathy, J Neurol Neurosurg Psychiatry. 1991; 54:230-5.
Hahnenkamp et al., Local anaesthetics inhibit signalling of human NMDA receptors recombinantly expressed in Xenopus laevis oocytes: role of protein kinase C, Br J Anaesth. 2006; 96(1):77-87.
Hartman et al., Global changes in STAT target selection and transcription regulation upon interferon treatments, Genes Dev. 2005; 19(24):2953-68.
Hellwig et al., TRPV1 Acts as Proton Channel to Induce Acidification in Nociceptive Neurons, The Journal of Biological Chemistry. 2004; 279:34553-34561.
Hill et al., TRPA1 Is Differentially Modulated by the Amphipathic Molecules Trinitrophenol and Chlorpromazine J Biol Chem. 2007; 282:7145-7153.
Hille, The pH-dependent rate of action of local anesthetics on the node of Ranvier. Journal of General Physiology. 1977; 69(4), 475-96.
Holmdahl et al., A substance P antagonist, [D-Pro2, D-Trp7,9]SP, inhibits inflammatory responses in the rabbit eye Science. Nov. 27, 1981;214(4524):1029-31.
Hu et al., Human apolipoprotein L1 (ApoL1) in cancer and chronic kidney disease (Review Paper), available in PMC Apr. 5, 2012, published in final edited form as: FEBS Lett. 2012; 586(7):947-55 (19 pages).
Hunt et al., Treatment of asthma with nebulized lidocaine: a randomized, placebo-controlled study. J Allergy Clin Immunol 2004; 113(5):853-9.
Hunter et al., The Contribution of Peripheral Sensory Neuronal Input towards the Maintenance of Neuropathic Pain Soc Neurosci. 1995; 21:1411. (Abstract Only).
Ikeda et al., Interactions of bupivacaine with ionic channels of the nicotinic receptor. Electrophysiological and biochemical studies. Molecular Pharmacology. 1984; 26(2), 293-303.
Ikoma et al., The neurobiology of itch. Nat Rev Neurosci. Jul. 2006;7(7):535-47. Review.
Jasmin et al., The Cold Plate as a Test of Nociceptive Behaviors: Description and Application to the Study of Chronic Neuropathic and Inflammatory Pain Models, Pain. 1998; 75:367-382.
Jia et al., TRPV1 receptor: a target for the treatment of pain, cough, airway disease and urinary incontinence, Drug News Perspect. 2005; 18(3):165-71. Abstract only.
Joos et al., Role of tachykinins in asthma. Allergy 2000; 55(4):321-37.
Juengst, What next for human gene therapy? Gene transfer often has multiple and unpredictable effects on cells, BMJ. 2003; 326(7404):1410-1.

Kalso et al., Sodium channel blockers in neuropathic pain, Current Pharmaceutical Design. 2005; 11(23):3005-11. Abstract Only.
Kaufman et al., Transgenic analysis of a 100-kb human beta-globin cluster-containing DNA fragment propagated as a bacterial artificial chromosome, Blood. 1999; 94(9):3178-84.
Kawamata et al., Effects of systemic administration of lidocaine and QX-314 on hyperexcitability of spinal dorsal horn neurons after incision in the rat, Pain. 2006; 122(1-2):68-80.
Kiberstis, Letter and reviews from Science (1189125), E-mail to Martin Pollak dated Mar. 16, 2010 (3 pages).
Kim et al., Monosubstituted guanidines from primary amines and aminoiminomethanesulfonic acid. Tetrahedron Lett. Dec. 1988;29(26):3183-3186.
Kirkpatrick et al., Comparison of the effects of procaine, chlorpromazine and their quaternary derivatives on nerve action potentials, Res Commun Chem Pathol Pharmacol. 1970; 1(1):149-155.
Kochegarov, Pharmacological modulators of voltage-gated calcium channels and their therapeutical application, Cell Calcium. 2003; 33(3):145-62.
Kutchai et al., Inhibition of the Na,K-ATPase of canine renal medulla by several local anesthetics, Pharmacol Res. 2001; 43(4):399-403.
Lecordier et al., C-terminal mutants of apolipoprotein L-I efficiently kill both Trypanosoma brucei brucei and Trypanosoma brucei rhodesiense, PLoS Pathog 2009; 5(12):e1000685 1-11.
Lee et al., Role of TRPV1 in inflammation-induced airway hypersensitivity, Curr Opin Phamacol. 2009; 9(3):243-9.
Leffler et al., The Vanilloid Receptor TRPV1 is Activated and Sensitized by Local Anesthetics in Rodent Sensory Neurons, J. Clin. Invest. 2008; 118:763-776.
Levine et al., The contribution of neurogenic inflammation in experimental arthritis. J Immunol. 1985; 135(2):843-847.
Levy, Target neurons to relieve asthma, Nature 2015; 523:8-9.
Li et al., Distribution and effect of apoL-I genotype on plasma lipid and apolipoprotein levels in Chinese normalipidemic and endogenous hypertriglyceridemic subjects, Clin Chim Acta. 2009; 403(1-2):152-5.
Lim et al., The Quaternary Lidocaine Derivative, QX-314, Produces Long-lasting Local Anesthesia in Animal Models In Vivo, Anesthesiology. 2007; 107:305-311.
Lin et al., Alternative splicing in the voltage-sensing region of N-Type CaV2.2 channels modulates channel kinetics. J Neurophysiol. Nov. 2004; 92(5):2820-30.
Longobardo et al., Effects of a quaternary bupivacaine derivative on delayed rectifier K+ currents. British Journal of Pharmacology. 2000;130(2): 391-401.
Lucioni et al., Botulinum toxin type A inhibits sensory neuropeptide release in rat bladder models of acute injury and chronic inflammation. BJU Int. Feb. 2008; 101(3):366-70.
Lukacs et al., Non-blocking modulation contributes to sodium channel inhibition by a covalently attached photoreactive riluzole analog. Sci Rep. May 25, 2018;8(1):8110.
Lundberg et al., Vascular permeability changes and smooth muscle contraction in relation to capsaicin-sensitive substance P afferents in the guinea-pig. Acta Physiol Scand. Feb. 1984;120(2):217-27.
MacPherson et al., Noxious compounds activate TRPA1 ion channels through covalent modification of cysteines. Nature. Feb. 1, 2007; 445(7127):541-5.
March, Advanced Organic Chemistry: Reactions, Mechanisms and Structure, John Wiley & Sons, Inc., 1992, p. 383.
McCleskey, Neuroscience: a local route to pain relief, Nature. 2007; 449(7162):545-6.
McGivern et al., Voltage-Gated Calcium Channels as Targets for the Treatment of Chronic Pain, Curr. Drug Targets CNS Neurol. Disord. 2004; 3:457-478.
Meyers et al., Lighting up the Senses: FM1-43 Loading of Sensory Cells through Nonselective Ion Channels, J. Neurosci. 2003; 23:4054-4065.
Mizogami et al., Local anesthetics adsorbed onto infusion balloon, Anesth Analg. 2004; 99(3):764-8.
Molina-Portela et al., Distinct roles of apolipoprotein components within the trypanosome lytic factor complex revealed in a novel transgenic mouse model, J Exp Med. 2008; 205(8):1721-8.

(56) References Cited

OTHER PUBLICATIONS

Nazif et al., Neural upregulation in interstitial cystitis. Urology Apr. 2007; 69(4 Suppl):24-33.
Nguyen et al., Colitis induced by proteinase-activated receptor-2 agonists is mediated by a neurogenic mechanism. Canadian J. Phys. Pharm. 2003; 81(9):920-927.
Ni et al., Thermal sensitivity of isolated vagal pulmonary sensory neurons: role of transient receptor potential vanilloid receptors, Am J Physiol Regul Integr Comp Physiol. 2006; 291(3):R541-50.
Nielsen et al., Assessment of the combined approach of N-alkylation and salt formation to enhance aqueous solubility of tertiary amines using bupivacaine as a model drug, Eur J of Pharm Sci. 2005; 24(1):85-93.
Nielsen et al., Bioreversible quaternary N-acyloxymethyl derivatives of the tertiary amines bupivacaine and lidocaine-synthesis, aqueous solubility and stability in buffer, human plasma and simulated intestinal fluid European Journal of Pharmaceutical Sciences. 2005; 24:433-440.
O'Connor et al., The role of substance P in inflammatory disease. J Cell Physiol 2004; 201(2):167-80.
O'Dell et al., Fatty acyl amides of endogenous tetrahydroisoquinolines are active at the recombinant human TRPV1 receptor. Bioorg Med Chem 2007; 15(18):6164-6149.
Omana-Zapata et al., QX-314 inhibits ectopic nerve activity associated with neuropathic pain, Brain Res. 1997; 771:228-237.
Owsianik et al., Permeation and selectivity of TRP channels, Annu Rev Physiol. 2006; 68:685-717.
Page et al., Polymorphisms in the Apolipoprotein L1 gene and their effects on blood lipid and glucose levels in middle age males, Genes Nutr. 2006; 1(2):133-5.
Page et al., The human apolipoprotein L gene cluster: identification, classification, and sites of distribution, Genomics 2001; 74(1):71-8.
Paliani-Katsitadze et al., Comparative study of the antiarrhythmic effects of bonnecor and some mesidides of α-azacycloalkanecarboxylic acids. Eksperimental'naya i Klinicheskaya Farmakologiya. 1994; 57(3), 15-17.
Paul, Genes linked to kidney disease, Genetics Abstract, <http://geneticabstracts.blogspot.com/2008/10/genes-linked-to-kidney-disease.html>, retrieved on Aug. 22, 2011 (2 pages).
Perez-Reyes, Molecular physiology of low-voltage-activated T-type calcium channels, Physiol Rev. 2003; 83(1):117-61.
Poss et al., A mild and efficient method for the preparation of guanidines. Tetrahedron Lett. Sep. 1992;33(40):5933-5936.
Puopolo et al., Permeation and block of TRPV1 channels by cationic local anesthetics. Program No. 628.11. Neuroscience Meeting Planner, Sep. 10, 2008, Washington, D.C: Society for Neuroscience. Online (2 pages).
Qu et al., Molecular determinants of drug access to the receptor site for antiarrhythmic drugs in the cardiac Na+ channel, Proc Natl Acad Sci USA. 1995; 92:11839-11843.
Rathmell et al., Assessment of Differential Sensory Blockade Using QX-314 and Capsaicin in Large Animals. Presentation No. PW 233. 12th World Congress on Pain Itinerary Planner, Glasgow, Scotland: International Association for the Study of Pain, 2008. Retrieved Online Jan. 31, 2008 (2 pages).
Ren et al., Interactions between the immune and nervous systems in pain. Nat Med. Nov. 2010; 16(11):1267-76. Epub Oct. 14, 2010.
Renz et al., The role of neurotrophins in bronchial asthma: contribution of the pan-neurotrophin receptor p75. Prog Brain Res. 2004; 146:325-33.
Rich et al., Quaternary quinidine derivatives as a tool to study: block of human potassium channels, Biophys J. 1994; 66(2):A143.
Ross et al., Cyclization of three N-w-haloalkyl-N-methylaminoaceto-2,6-xylidide derivatives in relation to their local anesthetic effect in vitro and in vivo. J Pharmacol Exp Ther. Aug. 1972;182(2):351-61.
Ross et al., Formation of a piperidinium derivative from N-(5'-chloropentyl)-N-methylaminoaceto-2,6-xylidide in relation to the sustained local anaesthetic action on the sciatic nerve of the guinea-pig in vivo. Nat New Biol. Apr. 28, 1971;230(17):274-5.
Ruparel et al., Homologous and heterologous desensitization of capsaicin and mustard oil responses utilize different cellular pathways in nociceptors, Pain. 2008; 135(3):271-9.
Schlama et al., One-Step Synthesis of Chiral Guanidinium Salts from Phosgeniminium Salts. J. Org. Chem.1997; 62(12):4200-4202.
Schwarz et al., Effects of QX-314 on membrane properties of neurons in the ventrobasal thalamus, Proc West Pharmacol Soc. 2002; 45:29-31.
Schwarz et al., Lumbar intrathecal administration of the quaternary lidocaine derivative, QX-314, produces neurotoxicity in mice, Can. J. Anaesth. 2008; 55(1):473931 (Abstract Only).
Seko et al., Structure—Activity Study and Analgesic Efficacy of Amino Acid Derivatives as Ntype Calcium Channel Blockers Bioorganic & Medicinal Chemistry Letters Aug. 20, 2001; 11(16):2067-2070.
Sexton et al., 12-Lipoxygenase-derived eicosanoids protect against myocardial ischemia/reperfusion injury via activation of neuronal TRPV1. FASEB J. Sep. 2007; 21(11):2695-703.
Shiyi, Experimental study on analgesic effects of Epidural Capsaicin. Chin J Pain Med. 1(10):37-41 (2004) (English Abstract Provided).
Snutch, Targeting chronic and neuropathic pain: the N-type calcium channel comes of age, NeuroRx. 2005; 2(4):662-70.
Spitzker et al., Mechanisms of potassium- and capsaicin-induced axonal calcitonin gene-related peptide release: involvement of L- and T-type calcium channels and TRPV1 but not sodium channels. Neuroscience 2008; 151(3):836-42.
Steinhoff et al., Neurophysiological, Neuroimmunological, and Neuroendocrine Basis of Pruritus, J. Invest Dermatol. 2006; 126(8):1705-1718.
Strichartz et al., The inhibition of sodium currents in myelinated nerve by quarternary derivatives of lidocaine, J Gen Physiol. 1973; 62:37-57.
Stys et al., Tertiary and quaternary local anesthetics protect CNS white matter from anoxic injury at concentrations that do not block excitability, J Neurophysiol. 1992; 67:236-240.
Sullivan et al., Synergistic inhibition of lysophosphatidic acid signaling by charged and uncharged local anesthetics, Anesth Analg. 1999; 88(5):1117-24.
Szallasi et al., The vanilloid receptor TRPV1: 10 years from channel cloning to antagonist proof-of-concept, Nat Rev Drug Discov. 2007; 6(5):357-72 (17 pages).
Talbot et al., Silencing Nociceptor Neurons Reduces Allergic Airway Inflammation. Neuron. Jul. 15, 2015;87(2):341-54. Epub Jun. 25, 2015.
Tanelian et al., Sodium channel-blocking agents: Their use in neuropathic pain conditions, Pain Forum. 1995; 4(2):75-80.
Tarlap et al., Chemical modification of lyophilized proteins in nonaqueous environments. J Protein Chem. 1997; Apr.;16(3):183-93.
Taylor et al., Persistent cardiovascular and behavioral nociceptive responses to subcutaneous formalin require peripheral nerve input, J Neurosci. 1995; 15(11):7575-7584.
Taylor-Clark et al., Prostaglandin-induced activation of nociceptive neurons via direct interaction with transient receptor potential A1 (TRPA1). Mol Pharmacol. Feb. 2008;73(2):274-81.
Theil et al., Structure-aided drug design's next generation. Nat Biotechnol. May 2004;22(5):513-9.
Triggle, The pharmacology of ion channels: with particular reference to voltage-gated Ca2+ channels, Eur J Pharmacol. 1999; 375(1-3):311-25.
Tzur et al., Missense mutations in the APOL1 gene are highly associated with end stage kidney disease risk previously attributed to the MYH9 gene, Hum Genet. 2010; 128(3):345-50.
Vanhamme et al., The trypanosome lytic factor of human serum and the molecular basis of sleeping sickness, Int J Parasitol. 2004; 34(8):887-98.
Vanhollebeke et al., Distinct roles of haptoglobin-related protein and apolipoprotein L-I in trypanolysis by human serum, Proc Natl Acad Sci USA. 2007; 104(10):4118-23.
Vanhollebeke et al., Human Trypanosoma evansi infection linked to a lack of apolipoprotein L-I, N Engl J Med. 2006;355(26):2752-6.

(56) References Cited

OTHER PUBLICATIONS

Vieira et al., Effect of ricinoleic acid in acute and subchronic experimental models of inflammation, Med of Inflam. 2000; 9(5):223-228.

Wan et al., Apolipoprotein L1, a novel Bcl-2 homology domain 3-only lipid-binding protein, induces autophagic cell death, J Biol Chem. 2008; 283(31): 21540-9.

Wang et al., N-Butyl Tetracaine as a Neurolytic Agent for Ultralong Sciatic Nerve Block, Anesthesiology 1996; 85:1386-1394.

Wang et al., Quaternary Ammonium Derivative of Lidocaine as a Long-acting Local Anesthetic, Anesthesiology 1995; 83:1293-1301.

Wang et al., Rapid analysis of gene expression (RAGE) facilitates universal expression profiling, Nucelic Acids Res. 1999; 27(23):4609-18.

Winkelman et al., Inhibition of the A-type K+ channels of dorsal root ganglion neurons by the long-duration anesthetic butamben, J Pharmacol Exp Ther. 2005;314(3):1177-86.

Wood et al., Voltage-gated sodium channel blockers; target validation and therapeutic potential, Current Topics in Medicinal Chemistry, 5(6):529-537 (2005). Abstract Only.

Woolf et al., Neuropathic pain: aetiology, symptoms, mechanisms, and management, Lancet. 1999;353(9168):1959-64.

Woolf, Evidence for a central component of post-injury pain hypersensitivity, Nature. 1983;306:686-688.

Yaksh, Calcium channels as therapeutic targets in neuropathic pain, J Pain 2006;7:S13-S30.

Yamazaki et al., J Pharm. Soc. Japan 1953; 73:294.

Yanagidate et al., Local anesthetics, Handb Exp Pharmacol. 2006; 177:95-127.

Yeh, Sodium inactivation mechanism modulates QX-314 block of sodium channels in squid axons, Biophys J. 1978; 24(2):569-74.

U.S. Appl. No. 12/515,429, filed Dec. 21, 2009, Bean et al.
U.S. Appl. No. 14/496,629, filed Sep. 25, 2014, Bean et al.
U.S. Appl. No. 15/470,324, filed Mar. 27, 2017, Bean et al.
U.S. Appl. No. 16/245,895, filed Jan. 11, 2019, Bean et al.
U.S. Appl. No. 16/562,083, filed Sep. 5, 2019, Bean et al.
U.S. Appl. No. 13/382,834, filed Mar. 26, 2012, Woolf et al.
U.S. Appl. No. 16/246,885, filed Jan. 14, 2019, Woolf et al.
U.S. Appl. No. 15/749,885, filed Feb. 2, 2018, Bean et al.
U.S. Appl. No. 16/733,762, filed Jan. 3, 2020, Bean et al.
EP 10797919.7, Oct. 29, 2012, Extended European Search Report.
EP 15002768.8, Nov. 24, 2015, Extended European Search Report.
EP 18211462, Apr. 23, 2019, Extended European Search Report.
PCT/US2010/041537, Oct. 18, 2010, International Search Report.
PCT/US2010/041537, Jan. 10, 2012, International Preliminary Report on Patentability and Written Opinion.

* cited by examiner

PERMANENTLY CHARGED SODIUM AND CALCIUM CHANNEL BLOCKERS AS ANTI-INFLAMMATORY AGENTS

CROSS-REFERENCE TO RELATED APPLICATIONS

This application is a divisional of and claims priority under 35 U.S.C. § 120 to U.S. patent application Ser. No. 13/382,834, filed Mar. 26, 2012, which is a national stage filing under 35 U.S.C. § 371 of international PCT application, PCT/US2010/041537, filed Jul. 9, 2010, which claims priority under 35 U.S.C. § 119(e) to U.S. Provisional Application Ser. No. 61/224,512, filed Jul. 10, 2009, each of which is hereby incorporated by reference.

FIELD OF THE INVENTION

The invention provides compounds, methods and kits for the treatment of neurogenic inflammation.

BACKGROUND OF THE INVENTION

The invention features methods and kits for the treatment of neurogenic inflammation by targeting nociceptors with drugs of low molecular weight, while minimizing effects on non-pain-sensing neurons or other types of cells.

According to the method of the invention, small, hydrophilic drug molecules gain access to the intracellular compartment of pain-sensing neurons via entry through receptor/channels that are present in pain-sensing neurons but to a lesser extent or not at all in other types of neurons or in other types of tissue.

Neurogenic inflammation is a mode of inflammation mediated by the efferent (motor) functions of sensory neurons, in which pro-inflammatory mediator molecules released in the periphery by pain-sensing neurons (nociceptors) both activate a variety of inflammatory pathways and also act on the vascular system to alter blood flow and capillary permeability.

Neurogenic inflammation contributes to the peripheral inflammation elicited by tissue injury, autoimmune disease, infection, exposure to irritants in a variety of tissues, and is thought to play an important role in the pathogenesis of numerous disorders (e.g. migraine, arthritis, rhinitis, gastritis, colitis, cystitis, and sunburn).

One way to reduce neurogenic inflammation is to block excitability in nociceptors, thereby preventing the activation of nociceptor peripheral terminals and the release of pro-inflammatory chemicals. Local anesthetics such as lidocaine and articaine act by inhibiting voltage gated ion channels in neurons. Local anesthetics are relatively hydrophobic molecules that gain access to their blocking site on the sodium channel by diffusing into or through the cell membrane. However, these anesthetics block sodium or calcium channels and thereby the excitability of all neurons, not just pain-sensing neurons. Thus, administration of local anesthetics produces unwanted or deleterious effects such as general numbness from block of low threshold pressure and touch receptors, motor deficits from block of motor axons and other complications from block of autonomic fibers. Local anesthetics also act on sodium channels on smooth muscle in the cardiovascular and respiratory systems producing deleterious effects.

Accordingly, there is a need for an approach to reducing neurogenic inflammation that selectively targets nociceptors.

SUMMARY OF THE INVENTION

In a first aspect, the invention features a method for treating neurogenic inflammation in a patient, such as a human, by administering a therapeutically effective amount of a compound that is capable of entering a nociceptor through a channel-forming receptor present in the nociceptor when the receptor is activated and inhibiting a voltage-gated ion channel present in the nociceptor, wherein the compound does not substantially inhibit said channel when applied to the extracellular face of the channel and when the receptor is not activated. In certain embodiments, the compound is an inhibitor of voltage-gated sodium channels. Exemplary inhibitors of this class are QX-314, N-methyl-procaine, QX-222, N-octyl-guanidine, 9-aminoacridine and pancuronium. In other embodiments, the compound is a quarternary amine derivative or other charged derivative of a compound selected from riluzole, mexilitine, phenytoin, carbamazepine, procaine, articaine, bupivicaine, mepivicaine, tocainide, prilocaine, diisopyramide, bencyclane, quinidine, bretylium, lifarizine, lamotrigine, flunarizine, and fluspirilene. In other embodiments, the compound is an inhibitor of calcium channels. Inhibitors of this class include D-890, CERM 11888, N-methyl-verapamil, N-methylgallopamil, N-methyl-devapamil, dodecyltrimethylammonium, and terpene compounds (e.g., sesquiterpenes), as well as charged derivatives (e.g., a quarternary amine derivative or a guanylated derivative) of verapamil, gallopamil, devapamil, diltiazem, fendiline, mibefradil, or farnesyl amine. Still other exemplary inhibitors of calcium channels can be described by Formulas XI-XIV) and in Tables 1, 2, and 3. In further embodiments, the ion channel inhibitor is a charged derivative (e.g., a quarternary amine derivative or a guanylated derivative) of any of compounds (1)-(563). Exemplary derivatives are described herein.

The channel-forming receptor can be activated prior to administering the compound by administration of a second compound that opens the channel. Alternatively, the channel-forming receptor can be activated by endogenous compounds present in the patient.

The invention also features a kit that includes a composition for treating neurogenic inflammation in a patient and instructions for the administration of the composition to a patient to treat neurogenic inflammation. The composition includes a compound that is capable of entering a nociceptor through a channel-forming receptor present in the nociceptor when the receptor is activated and inhibiting a voltage-gated ion channel present in the nociceptor, wherein the compound does not substantially inhibit said channel when applied to the extracellular face of the channel and when the receptor is not activated. In certain embodiments, the compound is an inhibitor of voltage-gated sodium channels or calcium channels, such as those described herein. In some embodiments, the compound is QX-314, N-methyl-procaine, QX-222, N-octyl-guanidine, 9-aminoacridine, pancuronium, or another low molecular weight, charged molecule that inhibits voltage-gated sodium channels when present inside of said nociceptor. In other embodiments, the compound is D-890, CERM 11888, N-methyl-verapamil, N-methylgallopamil, N-methyl-devapamil, and dodecyltrimethylammonium; a quarternary amine derivative, of verapamil, gallopamil, devapamil, diltiazem, fendiline, mibefradil, or farnesyl amine; a compound according to any of Formulas (XI), (XII), (XIII-A), (XIII-B), (XIII-C), and (XIV); or a quarternary amine derivative or other charged derivative of any of compounds (1)-(563).

Any of the compositions, methods, and kits of the invention may optionally feature a second compound that activates the channel-forming receptor. In one embodiment, the second compound activates a channel-forming receptor selected from TRPV1, P2X(2/3), TRPA1, and TRPM8.

Activators of TRPV1 receptors include but are not limited to capsaicin, eugenol, camphor, clotrimazole, arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldopamine (NADA), 6'-iodoresiniferatoxin (6'-IRTX), C18 N-acylethanolamines, lipoxygenase derivatives such as 12-hydroperoxyeicosatetraenoic acid, inhibitor cysteine knot (ICK) peptides (vanillotoxins), piperine, MSK195 (N-[2-(3,4-dimethylbenzyl)-3-(pivaloyloxy)propyl]-2-[4-(2-aminoethoxy)-3-methoxyphenyl]acetamide), JYL79 (N-[2-(3,4-dimethylbenzyl)-3-(pivaloyloxy)propyl]-N'-(4-hydroxy-3-methoxybenzyl)thiourea), hydroxy-alpha-sanshool, 2-aminoethoxydiphenyl borate, 10-shogaol, oleylgingerol, oleylshogaol, SU200 (N-(4-tert-butylbenzyl)-N'-(4-hydroxy-3-methoxybenzyl)thiourea), amylocaine, articaine, benzocaine, bupivacaine, carbocaine, carticaine, chloroprocaine, cyclomethycaine, dibucaine (cinchocaine), dimethocaine (larocaine), etidocaine, hexylcaine, levobupivacaine, lidocaine, mepivacaine, meprylcaine (oracaine), metabutoxycaine, piperocaine, prilocaine, procaine (novacaine), proparacaine, propoxycaine, risocaine, ropivacaine, tetracaine (amethocaine), and trimecaine. Other activators of TRPV1 receptors are described in O'Dell et al., Bioorg Med Chem. (2007) 15:6164-6149, and Sexton et al., FASEB J (2007) 21:2695-2703. Still other TRPV1 activators include black pepper compounds (e.g., Okumura et al., Biosci Biotechnol Biochem. 74(5):1068-72 (2010) and Riera et al., Br J Pharmacol. 57(8):1398-409 (2009)), terpenoids (Iwasaki et al., Life Sci. 85(1-2)60-69 (2009)), nickel (Luebbert et al., Pflugers Arch. 459(5):737-50 (2010)), SA13353 ([1-[2-(1-adamantyl)ethyl]-1-pentyl-3-[3-(4-pyridyl)propyl]urea]; see, e.g., Tsuji et al., Eur J Pharmacol. 627(1-3):332-9 (2010)), oxidized linoleic metabolites (Patwardhan et al., Proc Natl Acad Sci USA. 106(44):18820-4 (2009)), diallyl sulfides (Koizumi et al., Biochem Biophys Res Commun. 382(3):545-8 (2009)), and alkylamides derived from sanshool (Menozzi-Smarrito et al., J Agric Food Chem. 57(5):1982-9 (2009)).

Still other activators of TRPV1 receptors include capsaicinoids and capsaicinoid analogs as described herein (e.g., vanilloids (e.g., N-vanillyl-alkanedienamides, N-vanillyl-alkanedienyls, and N-vanillyl-cis-monounsaturated alkenamides), capsiate, dihydrocapsiate, nordihydrocapsiate and other capsinoids, capsiconiate, dihydrocapsiconiate and other coniferyl esters, capsiconinoid, resiniferatoxin, tinyatoxin, civamide, N-phenylmethylalkenamide capsaicin derivatives, olvanil, N-[(4-(2-aminoethoxy)-3-methoxyphenyl)methyl]-9Z-octa-decanamide, N-oleyl-homovanillamide, triprenyl phenols (e.g., scutigeral), gingerols, piperines, shogaols, guaiacol, eugenol, zingerone, nuvanil, NE-19550, NE-21610, and NE-28345). Additional capsaicinoids, their structures, and methods of their manufacture are described in U.S. Pat. Nos. 7,446,226 and 7,429,673, which are hereby incorporated by reference.

Activators of TRPA1 receptors include but are not limited to cinnamaldehyde, allyl-isothiocyanate, diallyl disulfide, icilin, cinnamon oil, wintergreen oil, clove oil, acrolein, hydroxy-alpha-sanshool, 2-aminoethoxydiphenyl borate, 4-hydroxynonenal, methyl p-hydroxybenzoate, mustard oil, 3'-carbamoylbiphenyl-3-yl cyclohexylcarbamate (URB597), amylocaine, articaine, benzocaine, bupivacaine, carbocaine, carticaine, chloroprocaine, cyclomethycaine, dibucaine (cinchocaine), dimethocaine (larocaine), etidocaine, hexylcaine, levobupivacaine, lidocaine, mepivacaine, meprylcaine (oracaine), metabutoxycaine, piperocaine, prilocaine, procaine (novacaine), proparacaine, propoxycaine, risocaine, ropivacaine, tetracaine (amethocaine), and trimecaine. Other activators of TRPA1 receptors are described in Taylor-Clark et al., Mol Pharmacol (2007) PMID: 18000030; Macpherson et al., Nature (2007) 445: 541-545; and Hill et al., J. Biol. Chem. (2007) 282:7145-7153. Still other TRPA1 activators include: fenamate NSAIDS (Hu et al., Pflugers Arch. 459(4):579-92 (2010)), congeners of AP18 (Defalco et al, Bioorg Med Chem Lett. 20(1):276-9 (2010)), tear gasses CN, CR, and CS (Brône et al., ToxicolAppl Pharmacol. 231(2):150-6 (2008)), nicotine (Talavera et al, Nat Neurosci. 12(10):1293-9 (2009)), Sichuan and Melegueta peppers (Riera et al., Br J Pharmacol. 157(8):1398-409 (2009)), diallyl sulfides nifedipine, nimodipine, nicardipine, and nitrendipine, L-type calcium channel agaonist BayK8644 (Fajardo et al., Channels (Austin) 2(6):429-38 (2008)), and isovelleral and polygodial (Escalera et al., J. Biol. Chem. 283(35):24136-44 (2008)).

Activators of P2X receptors include but are not limited to ATP, 2-methylthio-ATP, 2' and 3'-O-(4-benzoylbenzoyl)-ATP, and ATP5'-O-(3-thiotriphosphate).

Activators of TRPM8 receptors include but are not limited to menthol, icilin, eucalyptol, linalool, geraniol, and hydroxycitronellal.

In another aspect, the invention features compounds according to Formula (XI),

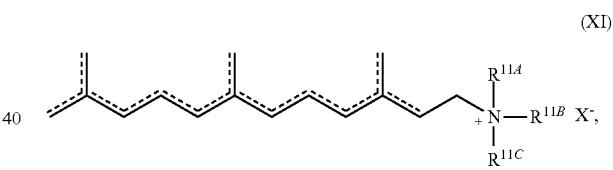

(XI)

where each $R^{11A}$, $R^{11B}$, and $R^{11C}$ is selected, independently, from H or $C_{1-4}$ alkyl, and where 0, 1, 2, or 3 of the dashed bonds represents a carbon-carbon double bond (i.e., compounds of Formula (XI) can include 0, 1, 2, or 3 double bonds), provided that when 2 or 3 carbon-carbon double bonds are present, the double bonds are not adjacent to one another. In some embodiments, compounds of Formula (XI) can be represented by the following formula (XI-A),

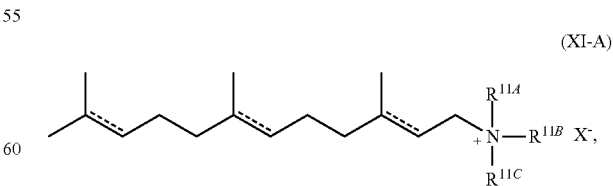

(XI-A)

where each $R^{11A}$, $R^{11B}$, $R^{11C}$, and X is according to Formula (XI), and where each dashed bond represents an optional carbon-carbon double bond, or by formula (XI-B),

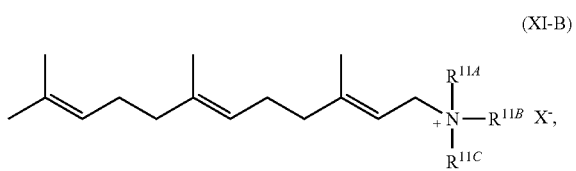

(XI-B)

where each $R^{11A}$, $R^{11B}$, $R^{11C}$, and X is according to Formula (XI). In some embodiments, the compound of Formula (XI) is

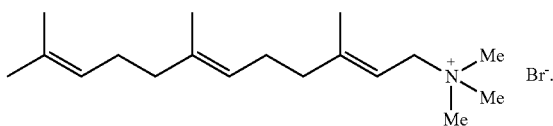

In another aspect, the invention features compounds according to Formula (XII),

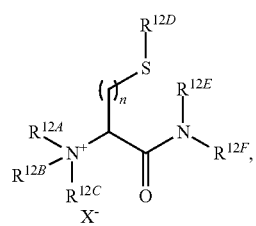

(XII)

each of $R^{12A}$, $R^{12B}$, $R^{12C}$, and $R^{12D}$ is, independently, selected from $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, and $C_{3-10}$ alkheterocyclyl; or $R^{12A}$ and $R^{12B}$ together complete a heterocyclic ring having at least one nitrogen atom; n is an integer between 1-5; each of $R^{12E}$ and $R^{12F}$ is, independently, selected from H, $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, or $C_{3-10}$ alkheterocyclyl; and X is any pharmaceutically acceptable anion. In some embodiments, the compound has the following structure,

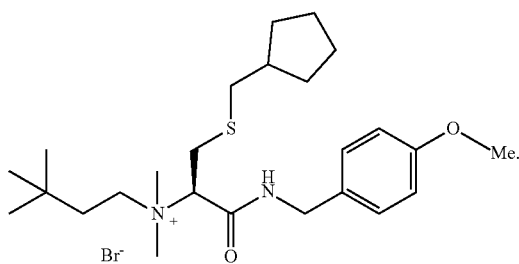

In another aspect, the invention features a compound having a structure according to one of the following formulas:

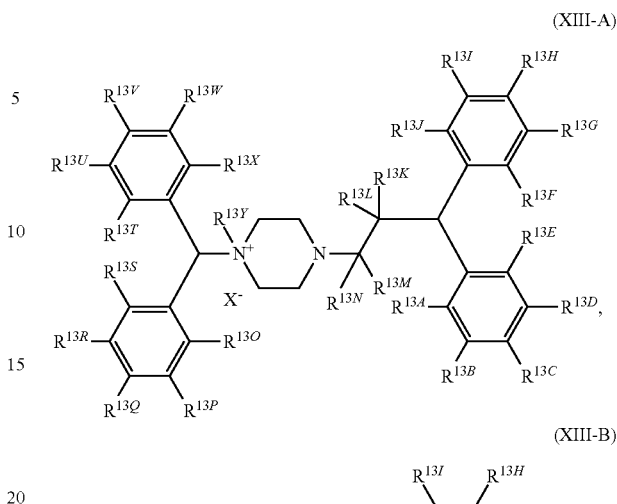

(XIII-A)

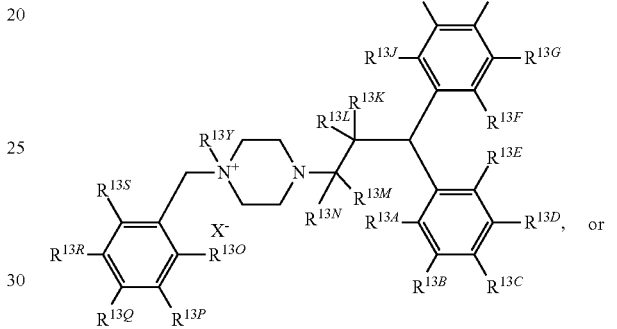

(XIII-B), or

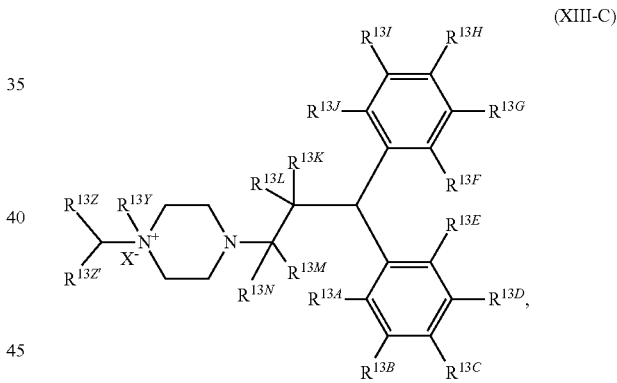

(XIII-C)

where each $R^{13A}$-$R^{13J}$ and $R^{13O}$-$R^{13T}$ is selected, independently, from H, halogen, $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, and $C_{3-10}$ alkheterocyclyl, $OR^{13AA}$, $NR^{13AB}R^{13AC}$, $NR^{13AD}C(O)R^{13AE}$, $S(O)R^{13AF}$, $SO_2R^{13AG}R^{13AH}$, $SO_2NR^{13AI}R^{13AJ}$, $SO_3^{13AK}$, $CO_2R^{13AL}$, $C(O)R^{13AM}$, and $C(O)NR^{13AN}R^{13AO}$; each of $R^{13AA}$-$R^{13AO}$ is, independently, selected from H, $C_{1-4}$ alkyl, $C_{2-4}$ alkenyl, $C_{2-4}$ alkynyl, and $C_{2-4}$ heteroalkyl; each $R^{13K}$, $R^{13L}$, $R^{13M}$, $R^{13N}$ is, independently, H or $C_{1-4}$ alkyl, or $R^{13K}$ and $R^{13L}$, or $R^{13M}$ and $R^{13N}$, combine to form C=O, or $R^{13K}$ and $R^{13M}$ combine to form C=C; $R^{13Y}$ is H or $C_{1-4}$ alkyl; $R^{13Z}$ and $R^{13Z'}$ are, independently, selected from H, halogen, $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, and $C_{3-10}$ alkheterocyclyl; and $X^-$ is any pharmaceutically acceptable anion. In some embodiments, the compound is selected from the group consisting of:

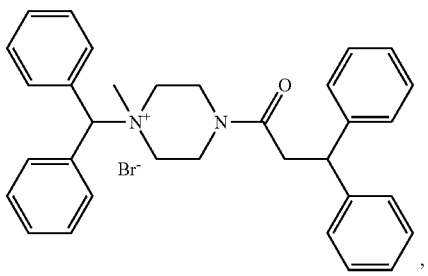

,

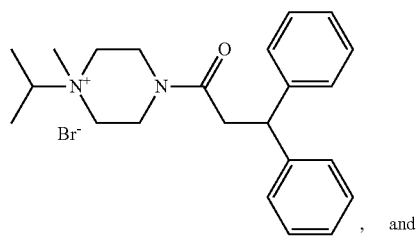

, and

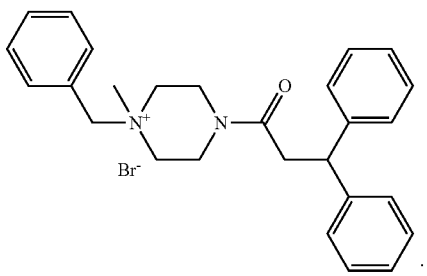

.

In another aspect, the invention features compounds according to the following formula,

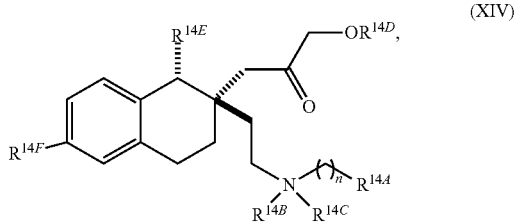

(XIV)

where n is an integer between 0-5; $R^{14A}$ is heterocyclyl, each of $R^{14B}R^{14C}$, $R^{14D}$, and $R^{14E}$ is, independently, $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, and $C_{3-10}$ alkheterocyclyl; and $R^{14F}$ is selected from H, halogen, $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, and $C_{3-10}$ alkheterocyclyl, $OR^{14G}$, $NR^{14H}R^{14I}$, $NR^{14J}C(O)R^{14K}$, $S(O)R^{14L}$, $SO_2R^{14M}R^{14N}$, $SO_2NR^{14O}R^{14P}$, $SO_3R^{14Q}$, $CO_2R^{14R}$, $C(O)R^{14S}$, and $C(O)NR^{14T}R^{14V}$; and each of $R^{14G}$-$R^{13AO}$ is, independently, selected from H, $C_{1-4}$ alkyl, $C_{2-4}$ alkenyl, $C_{2-4}$ alkynyl, and $C_{2-4}$ heteroalkyl. In some embodiments, the compound is

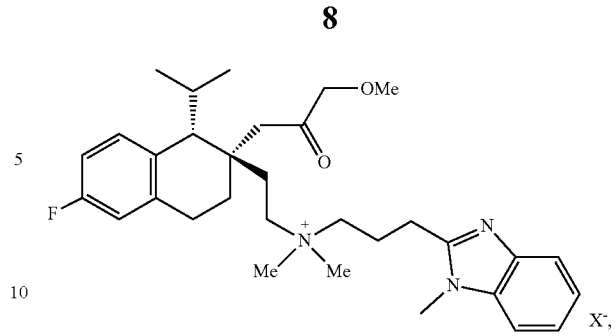

where X is a pharmaceutically acceptable anion.

The invention also features pharmaceutical compositions that include a compound according to any of Formulas (XI)-(XIV), or any of compounds (1)-(563), and a pharmaceutically acceptable excipient. In some embodiments, the pharmaceutical composition is formulated for oral, nasal, or inhalation administration.

In certain embodiments, the compounds, compositions, methods, and kits of the invention may be used to treat any disorder that is caused, wholly or in part, by neurogenic inflammation. Non-limiting examples of such disorders include asthma, rhinitis, conjunctivitis, arthritis, colitis, contact dermatitis, pancreatitis, chronic cough, sinusisitis (e.g., chronic rhinosinusistis), traumatic brain injury, sepsis (e.g., polymicrobial sepsis), tendinopathics chronic urticaria, rheumatic disease, acute lung injury, exposure to irritants, inhalation of irritants, pollutants or chemical warfare agents, eczema, cystitis, gastritis, urethritis, migraine headache, psoriasis, rhinitis, rosacea, sunburn, chemical warfare agents, inhaled tear gases, or inhaled pollutants.

Some methods and kits of the invention also feature one or more acetaminophens, NSAIDs, glucocorticoids, narcotics, tricyclic antidepressants, amine transporter inhibitors, anticonvulsants, antiproliferative agents, or immune modulators.

In another embodiment, the compositions are administered by intraarticular, surgical, intravenous, intramuscular, oral, rectal, cutaneous, subcutaneous, topical, transdermal, sublingual, nasal, vaginal, intraurethral, intravesicular, intrathecal, epidural, mucosal, aural, or ocular administration by injection, inhalation, or direct contact. In yet another embodiment, the composition is formulated for controlled or sustained release over time.

By "biologically active" is meant that a molecule, including biological molecules, such as nucleic acids, peptides, polypeptides, and proteins, exerts a physical or chemical activity on itself or other molecule. For example, a "biologically active" molecule may possess, e.g., enzymatic activity, protein binding activity (e.g., antibody interactions), or cytotoxic activities (e.g., anti-cancer properties). Biologically active agents that can be used in the methods and kits described herein include, without limitation, an antibody or antibody fragment, an antibiotic, a polynucleotide, a polypeptide, a protein, an anti-cancer agent, a growth factor, and a vaccine.

By "inflammation" is meant any types of inflammation, such those caused by the immune system (immune-mediated inflammation) and by the nervous system (neurogenic inflammation), and any symptom of inflammation, including redness, heat, swelling, pain, and/or loss of function.

By "neurogenic inflammation" is meant any type of inflammation mediated by neurons (e.g. nociceptors) or any other component of the central or peripheral nervous system.

By "patient" is meant any animal. In one embodiment, the patient is a human. Other animals that can be treated using the methods and kits of the invention include, but are not limited to, non-human primates (e.g., monkeys, gorillas, chimpanzees), domesticated animals (e.g., horses, pigs, goats, rabbits, sheep, cattle, llamas), and companion animals (e.g., guinea pigs, rats, mice, lizards, snakes, dogs, cats, fish, hamsters, and birds).

Compounds useful in the invention include, but are not limited to, those described herein in any of their pharmaceutically acceptable forms, including isomers such as diastereomers and enantiomers, salts, esters, amides, thioesters, solvates, and polymorphs thereof, as well as racemic mixtures and pure isomers of the compounds described herein.

By "low molecular weight" is meant less than about 650 Daltons.

The term "pharmaceutically acceptable salt" represents those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared in situ during the final isolation and purification of the compounds of the invention, or separately by reacting the free base function with a suitable organic acid. Representative acid addition salts include, but are not limited to, acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, isethionate, lactobionate, lactate, laurate, lauryl sulfate, malate, maleate, malonate, mesylate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. These acid addition salts may also be referred to as "pharmaceutically acceptable anions." Representative alkali or alkaline earth metal salts include, but are not limited to, sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-12}$ heteroalkyl, for example, includes from 1 to 12 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups.

By "$C_{1-4}$ alkyl" is meant a branched or unbranched hydrocarbon group having from 1 to 4 carbon atoms. A $C_{1-4}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-4}$ alkyls include, without limitation, methyl, ethyl, n-propyl, isopropyl, cyclopropyl, cyclopropylmethyl, n-butyl, iso-butyl, sec-butyl, tert-butyl, and cyclobutyl.

By "$C_{2-4}$ alkenyl" is meant a branched or unbranched hydrocarbon group containing one or more double bonds and having from 2 to 4 carbon atoms. A $C_{2-4}$ alkenyl may optionally include monocyclic or polycyclic rings, in which each ring desirably has from three to six members. The $C_{2-4}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-4}$ alkenyls include, without limitation, vinyl, allyl, 2-cyclopropyl-1-ethenyl, 1-propenyl, 1-butenyl, 2-butenyl, 3-butenyl, 2-methyl-1-propenyl, and 2-methyl-2-propenyl.

By "$C_{2-4}$ alkynyl" is meant a branched or unbranched hydrocarbon group containing one or more triple bonds and having from 2 to 4 carbon atoms. A $C_{2-4}$ alkynyl may optionally include monocyclic, bicyclic, or tricyclic rings, in which each ring desirably has five or six members. The $C_{2-4}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-4}$ alkynyls include, without limitation, ethynyl, 1-propynyl, 2-propynyl, I-butynyl, 2-butynyl, and 3-butynyl.

By "$C_{2-6}$ heterocyclyl" is meant a stable 5- to 7-membered monocyclic or 7- to 14-membered bicyclic heterocyclic ring which is saturated partially unsaturated or unsaturated (aromatic), and which consists of 2 to 6 carbon atoms and 1, 2, 3 or 4 heteroatoms independently selected from N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2- dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkcycloalkyl" is meant an alkyl substituted by a cycloalkyl group (e.g., cyclopropyl, cyclobutyl, cyclopentyl, cyclohexyl, cycloheptyl, or cyclooctyl) having from 3-10 carbon atoms.

By "$C_{3-10}$ alkheterocyclyl" is meant an alkyl substituted heterocyclic group having from 3 to 10 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, hydroxyalkyl, carboxyalkyl, and carboxyl groups. Examples of $C_{1-7}$ heteroalkyls include, without limitation, methoxymethyl and ethoxyethyl.

By "halide" is meant bromine, chlorine, iodine, or fluorine.

By "fluoroalkyl" is meant an alkyl group that is substituted with a fluorine atom.

By "perfluoroalkyl" is meant an alkyl group consisting of only carbon and fluorine atoms.

By "carboxyalkyl" is meant a chemical moiety with the formula —(R)—COOH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^{+}$, wherein R, R', R'', and R''' are each independently an optionally substituted alkyl, heteroalkyl, alkaryl, alkcycloalkyl, alkheterocyclyl, alkenyl, alkynyl, heteroaryl, or aryl group as described herein. R may be an alkyl group linking the quaternary amino nitrogen atom, as a substituent, to another moiety. The nitrogen atom, N, is covalently attached to four carbon atoms of the alkyl, heteroalkyl, alkaryl, alkcycloalkyl, alkheterocyclyl, alkenyl, alkynyl, heteroaryl, and/or aryl groups, resulting in a positive charge at the nitrogen atom.

By "charged moiety" is meant a moiety which gains a proton at physiological pH thereby becoming positively charged (e.g., ammonium, guanidinium, or amidinium) or a moiety that includes a net formal positive charge without protonation (e.g., quaternary ammonium). The charged moiety may be either permanently charged or transiently charged.

As used herein, the term "parent" refers to a channel blocking compound which can be modified by quaternization or guanylation of an amine nitrogen atom present in the parent compound. The quaternized and guanylated compounds are derivatives of the parent compound. The guanidyl derivatives described herein are presented in their uncharged base form. These compounds can be administered either as a salt (i.e., an acid addition salt) or in their uncharged base form, which undergoes protonation in situ to form a charged moiety.

By "therapeutically effective amount" means an amount sufficient to produce a desired result, for example, the reduction or elimination of neurogenic inflammation in a patient (e.g., a human) suffering from a condition, disease, or illness that is caused wholly or in part by neurogenic inflammation (e.g. asthma, arthritis, colitis, contact dermatitis, diabetes, eczema, cystitis, gastritis, migraine headache, psoriasis, rhinitis, rosacea, or sunburn).

Other features and advantages of the invention will be apparent from the following detailed description, and from the claims.

DETAILED DESCRIPTION OF THE INVENTION

Figure 1:
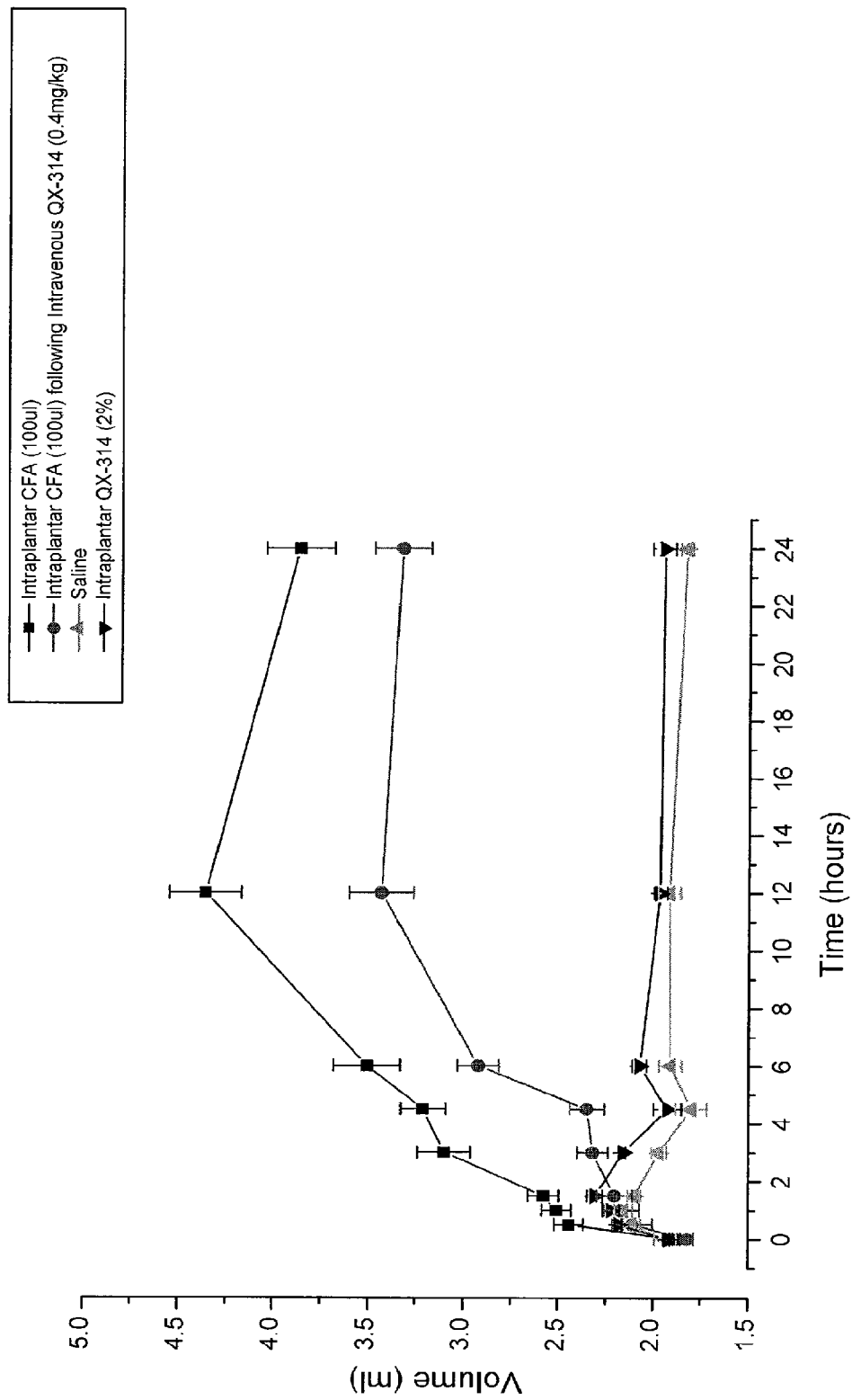
FIG. 1 is a graph showing the effect of intravenous QX-314 (0.4 mg/kg) on the edema elicited by injection of complete Freund's adjuvant (CFA) in the rat hindpaw determined by measuring the total volume of the hindpaw by plethysmography. The degree of swelling produced by injection of CFA is reduced by administration of QX-314 reflecting reduction in neurogenic edema resulting from the blockade of nociceptors by QX314. QX-314 by itself has no effect different from administration of saline.

The present invention features methods and kits for the treatment of neurogenic inflammation by administering a positively-charged, voltage-gated ion channel inhibitor. In embodiments of the invention, the positively-charged, voltage-gated ion channel inhibitor is administered alone or in combination with a TRP channel agonist such as capsaicinoid (e.g. capsaicin), mustard oil, or a "caine" drug (e.g., amylocaine, articaine, benzocaine, bupivacaine, carbocaine, carticaine, chloroprocaine, cyclomethycaine, dibucaine (cinchocaine), dimethocaine (larocaine), etidocaine, hexylcaine, levobupivacaine, lidocaine, mepivacaine, meprylcaine (oracaine), metabutoxycaine, piperocaine, prilocaine, procaine (novacaine), proparacainc, propoxycaine, risocaine, ropivacaine, tetracaine (amethocaine), or trimecaine).

Voltage-gated ion channels in pain-sensing neurons are currently of great interest in developing strategies to treat neurogenic inflammation. Blocking voltage-dependent sodium channels in nociceptors can reduce or eliminate neurogenic inflammation by preventing activation of nociceptor peripheral terminals and the release of pro-inflammatory chemicals. A limitation in designing small organic molecules that inhibit sodium channels or calcium channels is that they must be active when applied externally to the target cell. The vast majority of such externally-applied molecules are hydrophobic and can pass through cell membranes. Accordingly, such molecules will enter all cells and thus exhibit no selectivity for affecting only nociceptors.

Some inhibitors, such as the quarternary ammonium derivative QX-314, are membrane-impermeant and are only effective when present inside the nociceptor cell, and thus must pass through through the cell membrane via a channel or receptor, such as a transient receptor potential ion channel (TRP channels, e.g., TRPAV1, TRPA1, TRPM8, and P2X (2/3)), in order to produce an effect. Under normal circumstances, most TRP channels in nociceptors are not active but require a noxious thermal, mechanical, or chemical stimulus to activate them. For example, TRP channels in nociceptors can be activated by an exogenous TRP ligand (i.e. TRP agonist) such as capsaicin, which opens the TRPV1 channel.

Thus, one approach to selectively targeting nociceptors is to co-administer the membrane-impermeant ion channel inhibitor with an exogenous TRP ligand that permits passage of the inhibitor through the TRP channel into the cell. In addition to capsaicin, the exogenous TRP ligand can also be another capsaicinoid, mustard oil, or lidocaine. In another example, TRP channels may be active in response to exogenous irritant activators such as inhaled acrolein from smoke or chemical warfare agents such as tear gas.

Under certain circumstances, TRP channels can be activated in the absence of exogenous TRP activators/ligands by endogenous inflammatory activators that are generated by tissue damage, infection, autoimmunity, atopy, ischemia, hypoxia, cellular stress, immune cell activation, immune mediator production, and oxidative stress. Under such conditions, endogenous molecules (e.g., protons, lipids, and reactive oxygen species) can activate TRP channels expressed on nociceptors, allowing membrane-impermeant, voltage-gated ion channel blockers to gain access to the inside of the nociceptor through the endogenously-activated TRP channels. Endogenous inflammatory activators of TRP channels include, for example, prostaglandins, nitric oxide (NO), peroxide ($H_2O_2$), cysteine-reactive inflammatory mediators like 4-hydroxynonenal, endogenous alkenyl aldehydes, endocannabinoids, and immune mediators (e.g., interleukin 1 (IL-1), nerve growth factor (NGF), and bradykinin).

Thus, the inventors have discovered that membrane-impermeant, positively-charged inhibitors of voltage-gated ion channels (e.g., quarternary ammonium derivatives, such as QX-314), alone or in combination with an exogenous TRP ligand, can be used to selectively target nociceptors in order to effectively treat (e.g., eliminate or alleviate) neurogenic inflammation in a patient (e.g., a human).

The invention is described in more detail below.

Neurogenic Inflammation

Inflammation is a complex set of responses to harmful stimuli that results in localized redness, swelling, and pain. Inflammation has two components, one driven by antigens and mediated by immune cells (immune-mediated inflammation) and one mediated by the nervous system (neurogenic inflammation). Neurogenic inflammation results from the efferent functions of pain-sensing neurons (nociceptors), wherein neuropeptides and other chemicals that are pro-inflammatory mediators are released from the peripheral terminals of the nociceptors when they are activated. This release process is mediated by calcium influx and exocytosis of vesicles, and the pro-inflammatory mediators include substance P, neurokinin A and B (collectively known as tachykinins), and calcitonin gene-related peptide (CGRP).

The release of peripheral terminal chemicals stimulate a variety of inflammatory responses. First, the release of substance P can result in an increase in capillary permeability such that plasma proteins leak from the intravascular compartment into the extracellular space (plasma extravasation), causing edema. This can be detected as a wheal (a firm, elevated swelling of the skin) which is one component of a triad of inflammatory responses-wheal, red spot, and flare-known as the Lewis triple response. Second, the release of CGRP causes vasodilation, leading to increased blood flow. This can be detected as a flare, which is another component of the Lewis triple response.

Substance P also has a pro-inflammatory action on immune cells (e.g. macrophages, T-cells, mast cells, and dendritic cells) via their neurokinin-1 (NK1) receptor. This effect has been documented in allergic rhinitis, gastritis, and colitis, and represents an interface between the neurogenic and immune-mediated components of inflammation. Substance P released from one nociceptor may also act on NK1 receptors on neighboring nociceptors to sensitize or activate them, causing a spread of activation and afferent/efferent function.

These efferent functions of nociceptors can be triggered by: 1) Direct activation of a nociceptor terminal by a peripheral adequate stimulus applied to the terminal (e.g. a pinch); 2) Indirect antidromic activation of a non-stimulated nociceptor terminal by the axon reflex, wherein action potential input from one terminal of a nociceptor, upon reaching a converging axonal branch point in the periphery, results in an action potential traveling from the branch point down to the peripheral terminal of a non-stimulated terminal; and 3) Activation as a result of activity in nociceptor central terminals in the CNS traveling to the periphery (e.g., primary afferent depolarization of central terminals produced by GABA can be sufficient to initiate action potentials traveling the "wrong way").

Neurogenic Inflammatory Disorders

In certain disorders, neurogenic inflammation contributes to the peripheral inflammation elicited by tissue injury, autoimmune disease, infection, and exposure to irritants in soft tissue, skin, the respiratory system, joints, the urogenital and GI tract, the liver, and the brain. Neurogenic inflammatory disorders include asthma, rhinitis, conjunctivitis, arthritis, colitis, contact dermatitis, diabetes, eczema, cystitis, gastritis, migraine headache, psoriasis, rhinitis, rosacea, and sunburn. pancreatitis, chronic cough, chronic rhinosinusistis, traumatic brain injury, polymicrobial sepsis, tendinopathies chronic urticaria, rheumatic disease, acute lung injury, exposure to irritants, inhalation of irritants, pollutants, or chemical warfare agents, as described herein.

Asthma

Asthma is a chronic respiratory disorder that is characterized by airway obstruction, bronchial hyperresponsiveness, and bronchial inflammation. Asthma can be induced by a variety of stimuli, including natural inhaled allergens (e.g. dust mites, pollen, and mold), household organic compounds (e.g. soap, perfume, shampoo, creams, and lotions), medications, industrial chemicals, food allergies, exercise, hormonal changes, and psychological stress. Patients who chronicically suffer from asthma experience episodes of hypersensitivity to such stimuli where the bronchi contract in spasms. During an asthma episode, inflammation of the airways causes bronchoconstriction and excess mucus production, making it difficult for the patient to breathe.

Cells responsible for airway hyperresponsiveness and obstruction include sensory and motor neurons as well as epithelial and smooth muscle cells. Asthma is the result of a complex set of interactions between these cells and the immune system, particularly the T-helper-2 cells which control the inflammatory process. There is growing evidence that communication between immune cells and neurons can be mediated by neurophilins, which are produced in increased concentrations by immune cells that enter the airways in an asthmatic episode. Neurophilins modify the functional activity of neuronal function, leading to altered neuropeptide and tachykinin production that results in neurogenic inflammation. (Renz et al. *Prog. Brain Res.* 146:325, 2004.) TRPV1 and TRPA1 channels also contribute to the neurogenic component of allergic asthma as well as cough and rhinitis.

Arthritis

Arthritis is a group of conditions involving inflammation and damage to the joints of the body. Arthritis can have many causes, including physical trauma and aging (osteoarthritis), autoimmune disease (rheumatoid arthritis and psoriatic arthritis), infection (septic arthritis), and gout (gouty arthritis).

Rheumatoid arthritis (RA) is a chronic, systemic inflammatory disorder that principally affects the joints (synovitis), characterized by destruction of articular cartilage and bending/stiffness of the joints (ankylosis), and which leads to pain and substantial loss of mobility. RA can also cause inflammation in the skin, lungs, and kidneys. About 1% of the world population develops rheumatoid arthritis, with women having a three-fold higher risk than men.

The causes of autoimmunity in RA are not fully understood, but evidence suggests the involvement of abnormal B- and T-cell activation and the release of TNF and other cytokines. There has also been a causal link between cigarette smoke and RA. Studies have suggested that neurogenic inflammation makes an important contribution to the pathogenesis of joint pain in RA. See, for example, Levine et al. (*J. Immunol.* 135:843s, 1985), which showed that the severity of joint injury in RA is correlated with a greater local concentration of substance P.

Colitis

Colitis is a group of chronic autoimmune disorders characterized by inflammation of the colon. Symptoms of colitis include pain, tenderness of the abdomen, fatigue, rapid weight loss, ulcers (ulcerative colitis), and gastrointestinal bleeding. Colitis can also be triggered by many foods, including alcohol, caffeine, dairy products, spicy foods, nuts, seeds, meats, refined sugar, and raw vegetables. It is known that neurogenic mechanisms are important to the inflammatory processes in colitis. For example, studies have shown that induced colitis inflammation in mice can be mitigated using NK-1 and CGRP receptor antagonists. (Nguyen et al. *Canadian J. Phys. Pharm.* 81:920, 2003.)

Contact Dermatitis

Contact dermatitis is the local irritation of superficial regions of the skin caused by contact with irritants or allergens. In North America, the most common causes of allergic contact dermatitis are plants such as poison ivy and poison oak. Common causes of irritant contact dermatitis are chemicals such as harsh soaps, detergents, and cleaning products. Symptoms of contact dermatitis include rash, blisters, wheals, hives, and burning itch. The role of neurogenic inflammation in contact dermatitis has been discussed, for example, in Guy, *AMA Arch. Derm. Syphilol.* 66:1, 1952.

Gastritis

Gastritis refers to a collection of disorders which induce inflammation of the stomach lining. Gastritis can be caused by excessive alcohol consumption, prolonged use of NSAIDs such as aspirin or ibuprofen, and chronic infection by bacteria (primarily *Helicobacter pylori*). Certain autoimmune disorders can also cause gastritis. Symptoms include internal bleeding, pain (especially in the upper abdomen), vomiting, and bloating. Gastritis can also lead to increased risk of stomach cancer.

Migraine

Migraine is a neurological disorder, more common in women than in men, that is characterized by headache, nausea, and altered perception. Migraine proceeds in several phases: 1) a prodrome phase that includes fatigue, food craving, neck stiffness, altered mood, and constipation or diarrhea; 2) an aura phase that includes disturbances of vision consisting of white/multicolored flashes of lights or dazzling lines, feelings of "pins-and-needles" in the hand and arm, auditory/olfactory hallucinations, vertigo, tingling/numbness of the face, and hypersensitivity to touch; 3) a pain phase that includes a throbbing headache accompanied by nausea, vomiting, blurred vision, nasal stuffiness, diarrhea, and local edema; and 4) a postdrome phase including fatigue and feelings of "hangover."

There are many theories about the cause of migraine. Among these is the theory that certain nerves, when irritated, release the pro-inflammatory mediators such as substance P that lead to neurogenic inflammation and associated pain.

Rhinitis

Rhinitis, known commonly as the running nose, is a disorder involving irritation and inflammation of internal nasal mucous membranes. Rhinitis is characterized by the generation of large amounts of mucus, producing running nose, nasal congestion, and post-nasal drip. According to recent estimates, more than 50 million people in the U.S. alone suffer from rhinitis yearly. Rhinitis is categorized into infective rhinitis (caused by bacterial infection), nonallergic rhinitis (caused by hormones, drugs, and foods), and allergic rhinitis (caused by immune reactions to allergens, e.g. hayfever). The role of neurogenic inflammation in the pathogenesis of rhinitis is similar to that of asthma, where environmental substances enhance the immune response, leading to downstream release of substance P from neurons.

Cystitis

Cystitis is inflammation of the urinary bladder. There are several types of cystitis, including traumatic cystitis, interstitial cystitis, eosinophilic cystitis, radiation cystitis, and hemorrhagic cystitis. Interstitial cystitis, also known as painful bladder syndrome, is a disorder characterized by urination pain, urinary frequency, urgency, and pressure in the bladder. Unlike traumatic cystitis, interstitial cystitis has not been shown to be caused by bacterial infection. The cause of interstitial cystitis is unknown but has been proposed to involve neurogenic inflammation. For example, animal studies have shown that interstitial cystitis is correlated with both central and peripheral neural upregulation (Nazif et al., Urology 69:24-33 (2007)), and that acute bladder injury resulted in a significant increase in the release of substance P and CGRP (Lucioni et al., BJU Int. 101:366-370, 2008).

Additional Neurogenic Inflammatory Disorders

Additional neurogenic inflammatory disorders will be known to those skilled in the art, and include, but are not limited to sunburn, inflammatory conditions with a neurogenic component such as inflammation of blood vessels, eczema, rosacea, psoriasis, gingivitis, pancreatitis, chronic cough, chronic rhinosinusistis, traumatic brain injury, polymicrobial sepsis, tendinopathies chronic urticaria, acute lung injury, exposure to irritants, inhalation of irritants, pollutants, or chemical warfare agents.

Inhibitors of Voltage-Gated Ion Channels

Inhibitors of voltage-gated ion channels that are suitable for use in the methods and kits of the invention for the treatment of neurogenic inflammation are desirably positively-charged, hydrophilic compounds. In one embodiment, the compounds are permanently charged (i.e., have a charge that is not transient). In another embodiment, the compounds are transiently charged. Suitable inhibitors of voltage-gated sodium channels include, but are not limited to, QX-314, N-methyl-procaine (QX-222), N-octyl-guanidine, 9-aminoacridine, and pancuronium. Suitable inhibitors of voltage-gated calcium channels include, but are not limited to, D-890 (quaternary methoxyverapamil), CERM 11888 (quaternary bepridil), N-methyl-verapamil, N-methylgallopamil, N-methyl-devapamil, dodecyltrimethylammonium, and other compounds as described herein (see, e.g., charged derivatives of the compounds described in Tables 1 and 2).

Additionally, there are many known inhibitors of voltage-gated ion channels that would be of a suitable size to be useful in the methods of the invention (e.g., from about 100 to 4,000 Da, 100 to 3,000 Da, 100 to 2,000 Da, 150 to 1,500 Da, or even 200 to 1,200 Da) and that have amine groups, or can be modified to contain amine groups, that can be readily modified to be charged (e.g., as positively-charged quarternary amines, or as transiently charged, e.g., guanylated, compounds). Such inhibitors include, but are not limited to, riluzole, mexilitine, phenytoin, carbamazepine, procaine, tocainide, prilocaine, diisopyramide, bencyclane, quinidine, bretylium, lifarizine, lamotrigine, flunarizine, articaine, bupivicaine, mepivicaine, and fluspirilene.

Compounds that can be used in the methods and kits of the invention for the treatment of inflammation include compounds of formulas I-X, below.

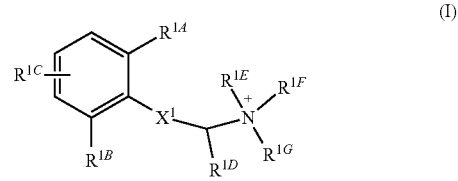

(I)

In formula I, each of $R^{1A}$, $R^{1B}$, and $R^{1C}$ is, independently, selected from H, halogen, $C_{1-4}$ alkyl, $C_{2-4}$ alkenyl, $C_{2-4}$ alkynyl, $OR^{1H}$, $NR^{1I}R^{1J}$, $NR^{1K}C(O)R^{1L}$, $S(O)R^{1M}$, $SO_2R^{1N}R^{1O}$, $SO_2NR^{1P}R^{1Q}$, $SO_3R^{1R}$, $CO_2R^{1S}$, $C(O)R^{1T}$, and $C(O)NR^{1U}R^{1V}$; and each of $R^{1H}$, $R^{1I}$, $R^{1J}$, $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, $R^{1U}$, and $R^{1V}$ is, independently, selected from from H, $C_{1-4}$ alkyl, $C_{2-4}$ alkenyl, $C_{2-4}$ alkynyl, and $C_{2-4}$ heteroalkyl $X^1$ is selected from —$CR^{1W}R^{1X}$—, —$NR^{1Y}C(O)$—, —OC(O)—, —SC(O)—, —C(O)NR^{1Z}—, —CO_2—, and —OC(S)—; and each of $R^{1W}$, $R^{1X}$, $R^{1Y}$, and $R^{1Z}$ is, independently, selected from H, $C_{1-4}$ alkyl, $C_{2-4}$ alkenyl, $C_{2-4}$ alkynyl, and $C_{2-4}$ heteroalkyl; RID is selected from H, $C_{1-4}$ alkyl, $C_{2-4}$ alkenyl, $C_{2-4}$ alkynyl, and $C_{2-4}$ heteroalkyl; and each of $R^{1E}$, $R^{1F}$, and $R^{1G}$ is, independently, selected from $C_{1-4}$ alkyl, $C_{2-4}$ alkenyl, $C_{2-4}$ alkynyl, and $C_{2-4}$ heteroalkyl; or $R^{1D}$ and $R^{1G}$ together complete a heterocyclic ring having at least one nitrogen atom. In a preferred embodiment, $X^1$ is —NHC(O)—. Exemplary compounds of formula I include methylated quaternary ammonium derivatives of anesthetic drugs, such as N-methyl lidocaine, N,N-dimethyl prilocaine, N,N,N-trimethyl tocainide, N-methyl etidocaine, N-methyl ropivacaine, N-methyl bupivacaine, N-methyl levobupivacaine, N-methyl mepivacaine. These derivatives can be prepared using methods analogous to those described in Scheme 1. Compounds of formula I include QX-314 (CAS 21306-56-9) and QX-222 (CAS 21236-55-5) (below).

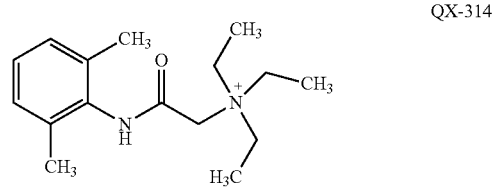

QX-314

-continued

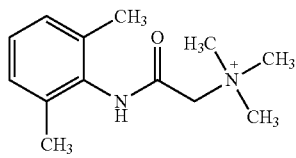
QX-222

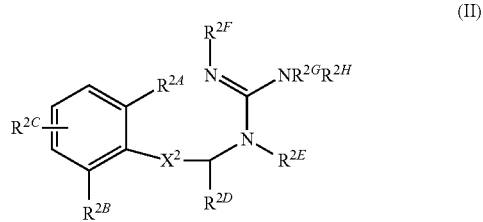
(II)

In formula II, each of $R^{2A}$, $R^{2B}$, and $R^{2C}$ is, independently, selected from H, halogen, $C_{1-4}$ alkyl, $C_{2-4}$ alkenyl, $C_{2-4}$ alkynyl, $OR^{2I}$, $NR^{2J}R^{2K}$, $NR^{2L}C(O)R^{2M}$, $S(O)R^{2N}$, $SO_2R^{2O}R^{2P}$, $SO_2NR^{2Q}R^{2R}$, $SO_3R^{2S}$, $CO_2R^{2T}$, $C(O)R^{2U}$, and $C(O)NR^{2V}R^{2W}$; and each of $R^{2I}$, $R^{2J}$, $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, $R^{2V}$, $R^{2W}$ is, independently, selected from H, $C_{1-4}$ alkyl, $C_{2-4}$ alkenyl, $C_{2-4}$ alkynyl, and $C_{2-4}$ heteroalkyl; $X^2$ is selected from $-CR^{2X}R^{2Y}-$, $-NR^{2Z}C(O)-$, $-OC(O)-$, $-SC(O)-$, $-C(O)NR^{2AA}-$, $-CO_2-$, and $-OC(S)-$; and each of $R^{2X}$, $R^{2Y}$, $R^{2Z}$, and $R^{2AA}$ is, independently, selected from H, $C_{1-4}$ alkyl, $C_{2-4}$ alkenyl, $C_{2-4}$ alkynyl, and $C_{2-4}$ heteroalkyl; $R^{2D}$ is selected from H, $C_{1-4}$ alkyl, $C_{2-4}$ alkenyl, $C_{2-4}$ alkynyl, and $C_{2-4}$ heteroalkyl; $R^{2E}$ is H or $C_{1-4}$ alkyl; and each of $R^{2F}$, $R^{2G}$, and $R^{2H}$ is, independently, selected from H, $C_{1-4}$ alkyl, $C_{2-4}$ alkenyl, $C_{2-4}$ alkynyl, and $C_{2-4}$ heteroalkyl; or $R^{2F}$ and $R^{2G}$ together complete a heterocyclic ring having two nitrogen atoms. Where $R^{2F}$ and $R^{2G}$ form a heterocyclic ring having two nitrogen atoms, the resulting guanidine group is, desirably, selected from

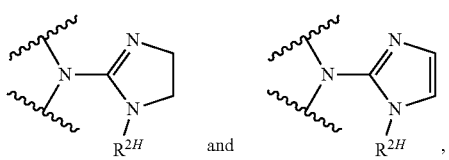

where $R^{2H}$ is H or $CH_3$. Desirably, $R^{2F}$ and $R^{2G}$ combine to form an alkylene or alkenylene of from 2 to 4 carbon atoms, e.g., ring systems of 5, 6, and 7-membered rings. In a preferred embodiment, $X^2$ is $-NHC(O)-$. Exemplary compounds of formula II include N-guanidyl derivatives (e.g., $-C(NH)NH_2$ derivatives) of anesthetic drugs, such as desethyl-N-guanidyl lidocaine, N-guanidyl prilocaine, N-guanidyl tocainide, desethyl-N-guanidyl etidocaine, desbutyl-N-guanidyl ropivacaine, desbutyl-N-guanidyl bupivacaine, desbutyl-N-guanidyl levobupivacaine, desmethyl-N-guanidyl mepivacaine. These derivatives can be prepared using methods analogous to those described in Schemes 2-5.

The guanidyl derivatives described herein (e.g., the compounds of formula II) are presented in their uncharged base form. These compounds can be administered either as a salt (i.e., an acid addition salt) or in their uncharged base form, which undergoes protonation in situ to form a charged moiety.

The synthesis of parent drugs of formulas I and II are described in the literature. See, for example, U.S. Pat. No. 2,441,498 (synthesis of lidocaine), U.S. Pat. No. 3,160,662 (synthesis of prilocaine), DE Patent No. 2235745 (synthesis of tocainide), DE Patent No. 2162744 (synthesis of etidocaine), PCT Publication No. WO85/00599 (synthesis of ropivacaine), U.S. Pat. No. 2,955,111 (synthesis of bupivacaine and levobupivacaine), and U.S. Pat. No. 2,799,679 (synthesis of mepivacaine).

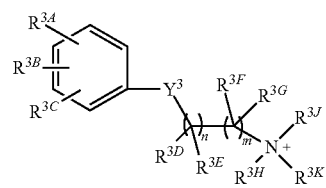
(III)

In formula III, n=0-3 and m=0-3, with (n+m)=0-6; each of $R^{3A}$, $R^{3B}$, and $R^{3C}$ is, independently, selected from H, halogen, $C_{1-4}$ alkyl, $C_{2-4}$ alkenyl, $C_{2-4}$ alkynyl, $C_{2-4}$ heteroalkyl, $OR^{3L}$, $NR^{3M}R^{3N}$, $NR^{3O}C(O)R^3$, $S(O)R^{3Q}$, $SO_2R^{3R}R^{3S}$, $SO_2NR^{3T}R^{3U}$, $SO_3R^{3V}$, $CO_2R^{3W}$, $C(O)R^{3X}$, and $C(O)NR^{3Y}R^{3Z}$; and each of $R^{3L}$, $R^{3M}$, $R^{3N}$, $R^{3O}$, $R^{3P}$, $R^{3Q}$, $R^{3R}$, $R^{3S}$, $R^{3T}$, $R^{3U}$, $R^{3V}$, $R^{3W}$, $R^{3X}$, $R^{3Y}$, $R^{3Z}$ is, independently, selected from H, $C_{1-4}$ alkyl, $C_{2-4}$ alkenyl, $C_{2-4}$ alkynyl, and $C_{2-4}$ heteroalkyl; $Y^3$ is selected from from $-CR^{3AA}R^{3AB}-$, $-NR^{3AC}C(O)-$, $-OC(O)-$, $-SC(O)-$, $-C(O)NR^{3AD}-$, $-CO_2-$, and $-OC(S)-$; and each of $R^{3AA}$, $R^{3AB}$, $R^{3AC}$, and $R^{3AD}$ is, independently, selected from H, $C_{1-4}$ alkyl, $C_{2-4}$ alkenyl, $C_{2-4}$ alkynyl, and $C_{2-4}$ heteroalkyl; each of $R^{3D}$, $R^{3E}$, $R^{3F}$, and $R^{3G}$ is, independently, selected from H, $C_{1-4}$ alkyl, $C_{2-4}$ alkenyl, $C_{2-4}$ alkynyl, $C_{2-4}$ heteroalkyl, $C_{2-6}$ heterocyclyl, $C_{6-12}$ aryl, $C_{7-14}$ alkaryl, and $C_{3-10}$ alkheterocyclyl; each of $R^{3H}$, $R^{3J}$, and $R^{3K}$ is, independently, selected from $C_{1-4}$ alkyl, $C_{2-4}$ alkenyl, $C_{1-4}$ alkynyl, and $C_{2-4}$ heteroalkyl. The quaternary nitrogen in formula III is identified herein as N'. Exemplary compounds of formula III include methylated quaternary ammonium derivatives of anesthetic drugs, such as N'-methyl procaine, N'-methyl proparacaine, N'-methyl allocain, N'-methyl encainide, N'-methyl procainamide, N'-methyl metoclopramide, N'-methyl stovaine, N'-methyl propoxycaine, N'-methyl chloroprocaine, N',N'-dimethyl flecainide, and N'-methyl tetracaine. These derivatives can be prepared using methods analogous to those described in Scheme 1.

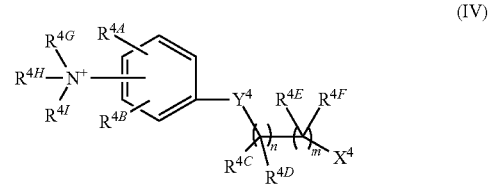
(IV)

In formula IV, n=0-3 and m=0-3, with (n+m)=0-6; each of $R^{4A}$ and $R^{4B}$ is, independently, selected from H, halogen, $C_{1-4}$ alkyl, $C_{2-4}$ alkenyl, $C_{2-4}$ alkynyl, $C_{2-4}$ heteroalkyl, $OR^{4L}$, $NR^{4M}R^{4N}$, $NR^{4O}C(O)R^{4P}$, $S(O)R^{4Q}$, $SO_2R^{4R}R^{4S}$, $SO_2NR^{4T}R^{4U}$, $SO_3R^{4V}$, $CO_2R^{4W}$, $C(O)R^{4X}$, and $C(O)NR^{4Y}R^{4Z}$; and each of $R^{4L}$, $R^{4M}R^{4N}$, $R^{4O}$, $R^{4P}$, $R^{4Q}$, $R^{4R}$, $R^{4S}$, $R^{4T}$, $R^{4U}$, $R^{4V}$, $R^{4W}$, $R^{4X}$, $R^{4Y}$, and $R^{4Z}$ is, independently, selected from H, $C_{1-4}$ alkyl, $C_{2-4}$ alkenyl, $C_{2-4}$ alkynyl, and $C_{2-4}$ heteroalkyl; $Y^4$ is selected from $-CR^{4AA}R^{4AB}-$, $-NR^{4AC}C(O)-$, $-OC(O)-$, $-SC$ (O)—, —C(O)NR$^{4AD}$—, —CO$_2$—, and —OC(S)—; and each of R$^{4AA}$, R$^{4AB}$, R$^{4A}$, and R$^{4AD}$ is, independently, selected from H, C$_{1-4}$ alkyl, C$_{2-4}$ alkenyl, C$_{2-4}$ alkynyl, and C$_{2-4}$ heteroalkyl; each of R$^{4C}$, R$^{4D}$, R$^{4E}$, and R$^{4F}$ is, independently, selected from H, C$_{1-4}$ alkyl, C$_{2-4}$ alkenyl, C$_{2-4}$ alkynyl, C$_{2-4}$ heteroalkyl, C$_{2-6}$ heterocyclyl, C$_{6-12}$ aryl, C$_{7-14}$ alkaryl, and C$_{3-10}$ alkheterocyclyl; X$^4$ is selected from H, C$_{1-4}$ alkyl, C$_{2-4}$ alkenyl, C$_{2-4}$ alkynyl, and NR$^{4J}$R$^{4K}$; each of R$^{4J}$ and R$^{4K}$ is, independently, selected from H, C$_{1-4}$ alkyl, C$_{2-4}$ alkenyl, C$_{2-4}$ alkynyl, and C$_{2-4}$ heteroalkyl; and each of R$^{4G}$, R$^{4H}$, and R$^{4I}$ is, independently, selected from C$_{1-4}$ alkyl, C$_{2-4}$ alkenyl, C$_{2-4}$ alkynyl, and C$_{2-4}$ heteroalkyl. The quaternary nitrogen in formula IV is identified herein as N''. Exemplary compounds of formula III include methylated quaternary ammonium derivatives of anesthetic drugs, such as N'',N'',N''-trimethyl procaine, N'',N'',N''-trimethyl proparacaine, N'',N'',N''-trimethyl procainamide, N'',N'',N''-trimethyl metoclopramide, N'',N'',N''-trimethyl propoxycaine, N'',N'',N''-trimethyl chloroprocaine, N'',N''-dimethyl tetracaine, N'',N'',N''-trimethyl benzocaine, and N'',N'',N''-trimethyl butamben. These derivatives can be prepared using methods analogous to those described in Scheme 1.

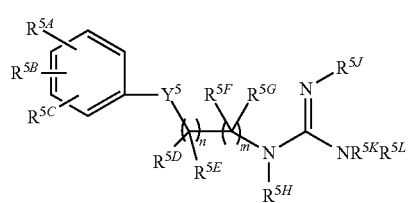

(V)

In formula V, n=0-3 and m=0-3, with (n+m)=0-6; each of R$^{5A}$, R$^{5B}$, and R$^{5C}$ is, independently, selected from H, halogen, C$_{1-4}$ alkyl, C$_{2-4}$ alkenyl, C$_{2-4}$ alkynyl, C$_{2-4}$ heteroalkyl, OR$^{5M}$, NR$^{5N}$R$^{5O}$, NR$^{5P}$C(O)R$^{5Q}$, S(O)R$^{5R}$, SO$_2$R$^{5S}$R$^{5T}$, SO$_2$NR$^{5U}$R$^{5V}$, SO$_3$R$^{5W}$, CO$_2$R$^{5X}$, C(O)R$^{5Y}$, and C(O)NR$^{5Z}$R$^{5AA}$; and each of R$^{5M}$, R$^{5N}$, R$^{5O}$, R$^{5P}$, R$^{5Q}$, R$^{5R}$, R$^{5S}$, R$^{5T}$, R$^{5U}$, R$^{5V}$, R$^{5W}$, R$^{5X}$, R$^{5Y}$, R$^{5Z}$ and R$^{5AA}$ is, independently, selected from H, C$_{1-4}$ alkyl, C$_{2-4}$ alkenyl, C$_{2-4}$ alkynyl, and C$_{2-4}$ heteroalkyl; Y$^5$ is selected from —CR$^{5AB}$R$^{5AC}$—, —NR$^{5AD}$C(O)—, —OC(O)—, —SC(O)—, —C(O)NR$^{5AE}$—, —CO$_2$—, and —OC(S)—; and each of R$^{5AB}$, R$^{5AC}$, R$^{5AD}$, and R$^{5AE}$ is, independently, selected from H, C$_{1-4}$ alkyl, C$_{2-4}$ alkenyl, C$_{2-4}$ alkynyl, and C$_{2-4}$ heteroalkyl; each of R$^{5D}$, R$^{5E}$, R$^{5F}$, and R$^{5G}$ is, independently, selected from H, C$_{1-4}$ alkyl, C$_{2-4}$ alkenyl, C$_{2-4}$alkynyl, C$_{2-4}$ heteroalkyl, C$_{2-6}$ heterocyclyl, C$_{6-12}$ aryl, C$_{7-14}$ alkaryl, and C$_{3-10}$ alkheterocyclyl; R$^{5H}$ is H or C$_{1-4}$ alkyl; and each of R$^{5J}$, R$^{5K}$, and R$^{5L}$ is, independently, selected from H, C$_{1-4}$ alkyl, C$_{2-4}$ alkenyl, C$_{2-4}$ alkynyl, and C$_{2-4}$ heteroalkyl; or R$^{5J}$ and R$^{5K}$ together complete a heterocyclic ring having two nitrogen atoms. Where R$^{5J}$ and R$^{5K}$ form a heterocyclic ring having two nitrogen atoms, the resulting guanidine group is, desirably, selected from

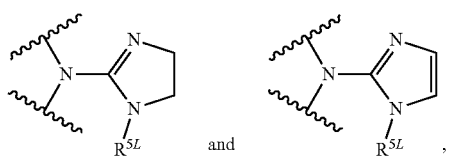

where R$^{5L}$ is H or CH$_3$. Desirably, R$^{5J}$ and R$^{5K}$ combine to form an alkylene or alkenylene of from 2 to 4 carbon atoms, e.g., ring systems of 5, 6, and 7-membered rings. The guanylated nitrogen in formula V is identified herein as N'. Exemplary compounds of formula V include N-guanidyl derivatives (e.g., —C(NH)NH$_2$ derivatives) of anesthetic drugs, such as such as desethyl-N'-guanidyl procaine, desethyl-N'-guanidyl proparacaine, desethyl-N'-guanidyl allocain, desmethyl-N'-guanidyl encainide, desethyl-N'-guanidyl procainamide, desethyl-N'-guanidyl metoclopramide, desmethyl-N'-guanidyl stovaine, desethyl-N'-guanidyl propoxycaine, desethyl-N'-guanidyl chloroprocaine, N'-guanidyl flecainide, and desethyl-N'-guanidyl tetracaine. These derivatives can be prepared using methods analogous to those described in Schemes 2-5.

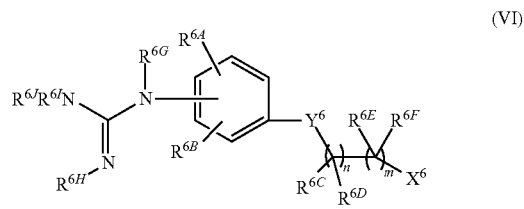

(VI)

In formula VI, n=0-3 and m=0-3, with (n+m)=0-6; each of R$^{6A}$ and R$^{6B}$ is, independently, selected from H, halogen, C$_{1-4}$ alkyl, C$_{2-4}$ alkenyl, C$_{2-4}$ alkynyl, C$_{2-4}$ heteroalkyl, OR$^{6K}$, NR$^{6L}$R$^{6M}$, NR$^{6N}$C(O)R$^{6O}$, S(O)R$^{6P}$, SO$_2$R$^{6Q}$R$^{6R}$, SO$_2$NR$^{6S}$R$^{6T}$, SO$_3$R$^{6U}$, CO$_2$R$^{6V}$, C(O)R$^{6W}$, and C(O)NR$^{6X}$R$^{6Y}$; and each of R$^{6K}$, R$^{6L}$, R$^{6M}$, R$^{6N}$, R$^{6O}$, R$^{6P}$, R$^{6Q}$, R$^{6R}$, R$^{6S}$, R$^{6T}$, R$^{6U}$, R$^{6V}$, R$^{6W}$, R$^{6X}$, and R$^{6Y}$ is, independently, selected from H, C$_{1-4}$ alkyl, C$_{2-4}$ alkenyl, C$_{21}$ alkynyl, and C$_{2-4}$ heteroalkyl; Y$^6$ is selected from —CR$^{7Z}$R$^{6AA}$—, —NR$^{6AB}$C(O)—, —OC(O)—, —SC(O)—, —C(O)NR$^{6AC}$—, —CO$_2$—, and —OC(S)—; and each of R$^{6Z}$, R$^{6AA}$, R$^{6AB}$, and R$^{6AC}$ is, independently, selected from H, C$_{1-4}$ alkyl, C$_{2-4}$ alkenyl, C$_{2-4}$ alkynyl, and C$_2$ heteroalkyl; each of R$^{6C}$, R$^{6D}$, R$^{6E}$, and R$^{6F}$ is, independently, selected from H, C$_{1-4}$ alkyl, C$_{2-4}$ alkenyl, C$_{2-4}$ alkynyl, C$_{2-4}$ heteroalkyl, C$_{2-6}$ heterocyclyl, C$_{6-12}$ aryl, C$_{7-14}$ alkaryl, and C$_{3-10}$ alkheterocyclyl; X$^6$ is selected from H, C$_{1-4}$ alkyl, C$_{2-4}$ alkenyl, C$_{2-4}$ alkynyl, and NR$^{6AD}$R$^{6AE}$; each of R$^{6AD}$ and R$^{6AE}$ is, independently, selected from H, C$_{1-4}$ alkyl, C$_{2-4}$ alkenyl, C$_{2-4}$ alkynyl, and C$_{2-4}$ heteroalkyl; R$^{6G}$ is H or C$_{1-4}$ alkyl; and each of R$^{6H}$, R$^{6I}$, and R$^{6J}$ is, independently, selected from H, C$_{1-4}$ alkyl, C$_{2-4}$ alkenyl, C$_{2-4}$ alkynyl, and C$_{2-4}$ heteroalkyl; or R$^{6H}$ and R$^{6I}$ together complete a heterocyclic ring having two nitrogen atoms. Where R$^{6H}$ and R$^{6I}$ form a heterocyclic ring having two nitrogen atoms, the resulting guanidine group is, desirably, selected from

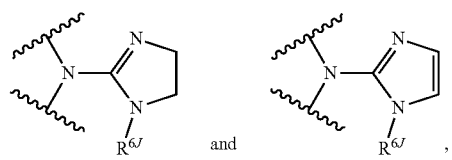

where R$^{6J}$ is H or CH$_3$. Desirably, R$^{6H}$ and R$^{6I}$ combine to form an alkylene or alkenylene of from 2 to 4 carbon atoms, e.g., ring systems of 5, 6, and 7-membered rings. The guanylated nitrogen in formula V is identified herein as N'''. Exemplary compounds of formula VI include N-guanidyl derivatives (e.g., —C(NH)NH$_2$ derivatives) of anesthetic drugs, such as such as N"-guanidyl procaine, N"-guanidyl proparacaine, N"-guanidyl procainamide, N"-guanidyl metoclopramide, N"-guanidyl propoxycaine, N"-guanidyl chloroprocaine, N"-guanidyl tetracaine, N"-guanidyl benzocaine, and N"-guanidyl butamben. These derivatives can be prepared using methods analogous to those described in Schemes 2-5.

The synthesis of parent drugs of formulas III-VI are described in the literature. See, for example, U.S. Pat. No. 812,554 (synthesis of procaine), Clinton et al., *J. Am. Chem. Soc.* 74:592 (1952) (synthesis of proparacaine), U.S. Pat. No. 2,689,248 (synthesis of propoxycaine), Hadicke et al., *Pharm. Zentralh.* 94:384 (1955) (synthesis of chloroprocaine), U.S. Pat. No. 1,889,645 (synthesis of tetracaine), Salkowski et al., *Ber.* 28:1921 (1895) (synthesis of benzocaine), Brill et al., *J. Am. Chem. Soc.* 43:1322 (1921) (synthesis of butamben), U.S. Pat. No. 3,931,195 (synthesis of encainide), Yamazaki et al., *J. Pharm. Soc. Japan* 73:294 (1953) (synthesis of procainamide), U.S. Pat. No. 3,177,252 (synthesis of metoclopramide), U.S. Pat. No. 3,900,481 (synthesis of flecainide), and Fourneau et al., *Bull. Sci. Pharmacol.* 35:273 (1928) (synthesis of stovaine), each of which is hereby incorporated by reference.

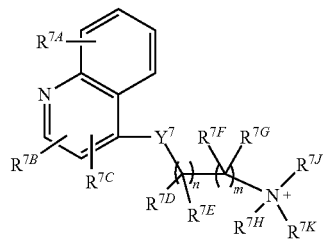

(VII)

In formula VII, n=0-3 and m=0-3, with (n+m)=0-6; each of $R^{7A}$, $R^{7B}$, and $R^{7C}$ is, independently, selected from H, halogen, $C_{1-4}$ alkyl, $C_{2-4}$ alkenyl, $C_{2-4}$ alkynyl, $C_{2-4}$ heteroalkyl, $OR^{7L}$, $NR^{7M}R^{7N}$, $NR^{7O}C(O)R^{7P}$, $S(O)R^{7Q}$, $SO_2R^{7R}R^{7S}$, $SO_2NR^{7T}R^{7U}$, $SO_3R^{7V}$, $CO_2R^{7W}$, $C(O)R^{7X}$, and $C(O)NR^{7Y}R^{7Z}$; and each of $R^{7L}$, $R^{7M}$, $R^{7N}$, $R^{7O}$, $R^{7P}$, $R^{7Q}$, $R^{7R}$, $R^{7S}$, $R^{7T}$, $R^{7U}$, $R^{7V}$, $R^{7W}$, $R^{7X}$, $R^{7Y}$, and $R^{7Z}$ is, independently, selected from H, $C_{1-4}$ alkyl, $C_{2-4}$ alkenyl, $C_{2-4}$ alkynyl, and $C_{2-4}$ heteroalkyl; $X^7$ is selected from —$CR^{7AA}R^{7AB}$—, —$NR^{7AC}C(O)$—, —$OC(O)$—, —SC(O)—, —$C(O)NR^{7AD}$—, —$CO_2$—, and —$OC(S)$—; and each of $R^{7AA}$, $R^{7AB}$, $R^{7A}$, and $R^{7AD}$ is, independently, selected from H, $C_{1-4}$ alkyl, $C_{2-4}$ alkenyl, $C_{2-4}$ alkynyl, and $C_{2-4}$ heteroalkyl; each of $R^{7D}$, $R^{7E}$, $R^{7F}$, and $R^{7G}$ is, independently, selected from H, $C_{1-4}$ alkyl, $C_{2-4}$ alkenyl, $C_{2-4}$ alkynyl, $C_{2-4}$ heteroalkyl, $C_{2-6}$ heterocyclyl, $C_{6-12}$ aryl, $C_{7-14}$ alkaryl, and $C_{3-10}$ alkheterocyclyl; and each of $R^{7H}$, $R^{7J}$, and $R^{7K}$ is, independently, selected from $C_{1-4}$ alkyl, $C_{2-4}$ alkenyl, $C_{2-4}$ alkynyl, and $C_{2-4}$ heteroalkyl. In a preferred embodiment, $X^7$ is —C(O)NH—. Exemplary compounds of formula VII include methylated quaternary ammonium derivatives of anesthetic drugs, such as N'-methyl dibucaine. These derivatives can be prepared using methods analogous to those described in Scheme 1.

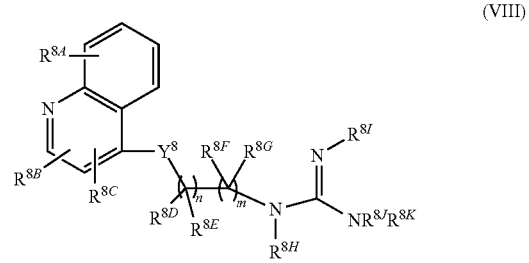

(VIII)

In formula VIII, n=0-3 and m=0-3, with (n+m)=0-6; each of $R^{8A}$, $R^{8B}$, and $R^{8C}$ is, independently, selected from H, halogen, $C_{1-4}$ alkyl, $C_{2-4}$ alkenyl, $C_{2-4}$ alkynyl, $C_{2-4}$ heteroalkyl, $OR^{8L}$, $NR^{8M}R^{8N}$, $NR^{8O}C(O)R^{8P}$, $S(O)R^{8Q}$, $SO_2R^{8R}R^{8S}$, $SO_2NR^{8T}R^{8U}$, $SO_3R^{8V}$, $CO_2R^{8W}$, $C(O)R^{8X}$, and $C(O)NR^{8Y}R^{8Z}$; and each of $R^{8L}$, $R^{8M}$, $R^{8N}$, $R^{8O}$, $R^{8P}$, $R^{8Q}$, $R^{8R}$, $R^{8S}$, $R^{8T}$, $R^{8U}$, $R^{8V}$, $R^{8W}$, $R^{8X}$, $R^{8Y}$, and $R^{8Z}$ is, independently, selected from H, $C_{1-4}$ alkyl, $C_{2-4}$ alkenyl, $C_{2-4}$ alkynyl, and $C_{2-4}$ heteroalkyl; $X^8$ is selected from —$CR^{8AA}R^{8AB}$—, —$NR^{8AC}C(O)$—, —$OC(O)$—, —SC(O)—, —$C(O)NR^{8AD}$—, —$CO_2$—, and —$OC(S)$—; and each of $R^{8AA}$, $R^{8AB}$, $R^{8AC}$, and $R^{8AD}$ is, independently, selected from H, $C_{1-4}$ alkyl, $C_{2-4}$ alkenyl, $C_{2-4}$ alkynyl, and $C_{2-4}$ heteroalkyl; each of $R^{8D}$, $R^{8E}$, $R^{8F}$, and $R^{8G}$ is, independently, selected from H, $C_{1-4}$ alkyl, $C_{2-4}$ alkenyl, $C_{2-4}$ alkynyl, $C_{2-4}$ heteroalkyl, $C_{2-6}$ heterocyclyl, $C_{6-12}$ aryl, $C_{7-14}$ alkaryl, and $C_{3-10}$ alkheterocyclyl; $R^{8H}$ is H or $C_{1-4}$ alkyl; and each of $R^{8I}$, $R^{8J}$, and $R^{8K}$ is, independently, selected from H, $C_{1-4}$ alkyl, $C_{2-4}$ alkenyl, $C_{2-4}$ alkynyl, and $C_{2-4}$ heteroalkyl; or $R^{8I}$ and $R^{8J}$ together complete a heterocyclic ring having two nitrogen atoms. Where $R^{8I}$ and $R^{8J}$ form a heterocyclic ring having two nitrogen atoms, the resulting guanidine group is, desirably, selected from

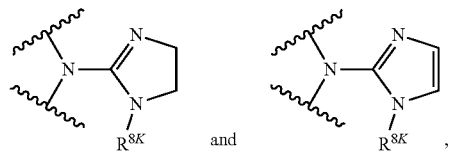

where $R^{8K}$ is H or $CH_3$. Desirably, $R^{8I}$ and $R^{8J}$ combine to form an alkylene or alkenylene of from 2 to 4 carbon atoms, e.g., ring systems of 5, 6, and 7-membered rings. The guanylated nitrogen in formula V is identified herein as N'. In a preferred embodiment, $X^8$ is —C(O)NH—. Exemplary compounds of formula VIII include N-guanidyl derivatives (e.g., —C(NH)NH$_2$ derivatives) of anesthetic drugs, such as such as desethyl-N-guanidyl dibucaine. These derivatives can be prepared using methods analogous to those described in Schemes 2-5.

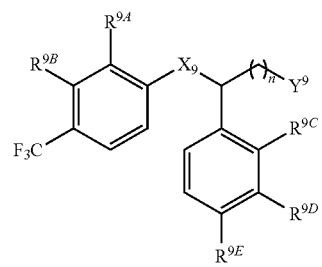

(IX)

In formula IX, n=0-6; each of $R^{9A}$, $R^{9B}$, $R^{9C}$, $R^{9D}$, and $R^{9E}$ is, independently, selected from H, halogen, $C_{1-4}$ alkyl, $C_{2-4}$ alkenyl, $C_{2-4}$ alkynyl, $OR^{9I}$, $NR^{9J}R^{9K}$, $NR^{9L}C(O)R^{1M}$, $S(O)R^{9N}$, $SO_2R^{9O}R^{9P}$, $SO_2NR^{9Q}R^{9R}$, $SO_3R^{9S}$, $CO_2R^{9T}$, $C(O)R^{9U}$, and $C(O)NR^{9V}R^{9W}$; and each of $R^{9I}$, $R^{9J}$, $R^{9K}$, $R^{9L}$, $R^{9M}$, $R^{9N}$, $R^{9O}$, $R^{9P}$, $R^{9Q}$, $R^{9R}$, $R^{9S}$, $R^{9T}$, $R^{9U}$, $R^{9V}$, and $R^{9W}$ is, independently, selected from H, $C_{1-4}$ alkyl, $C_{2-4}$ alkenyl, $C_{2-4}$ alkynyl, and $C_{2-4}$ heteroalkyl; $X^9$ is selected from —$CR^{9X}R^{9Y}$—, —O—, —S—, and —$NR^{9Z}$—; and each of $R^{9X}$, $R^{9Y}$, and $R^{9Z}$ is, independently, selected from H, $C_{1-4}$ alkyl, $C_{2-4}$ alkenyl, $C_{2-4}$ alkynyl, and $C_{2-4}$ heteroalkyl; $Y^9$ is $NR^{9AA}NR^{9AB}NR^{9AC}$ or $NR^{9AD}Z^9$; each of $R^{9AA}$, $R^{9AB}$, and $R^{9AC}$ is, independently, selected from H, $C_{1-4}$ alkyl, $C_{2-4}$ alkenyl, and $C_{2-4}$ alkynyl; $R^{9AD}$ is H or $C_{1-4}$ alkyl; $Z^9$ is

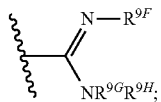

each of $R^{9F}$, $R^{9G}$, and $R^{9H}$ is, independently, selected from H, $C_{1-4}$ alkyl, $C_{2-4}$ alkenyl, and $C_{2-4}$ alkynyl, or $R^{9F}$ and $R^{9G}$ together complete a heterocyclic ring having two nitrogen atoms. Where $R^{9F}$ and $R^{9G}$ form a heterocyclic ring having two nitrogen atoms, the resulting guanidine group is, desirably, selected from

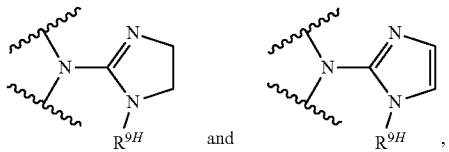

where $R^{9H}$ is H or $CH_3$. Desirably, $R^{9F}$ and $R^{9G}$ combine to form an alkylene or alkenylene of from 2 to 4 carbon atoms, e.g., ring systems of 5, 6, and 7-membered rings. In a preferred embodiment, $X^9$=—O—. Exemplary compounds of formula IX include N-guanidyl derivatives (e.g., —C(NH)NH$_2$ derivatives), such as N-guanidyl fluoxetine, and methylated quaternary ammonium derivatives, such as N,N-dimethyl fluoxetine. These derivatives can be prepared using methods analogous to those described in Schemes 1-5.

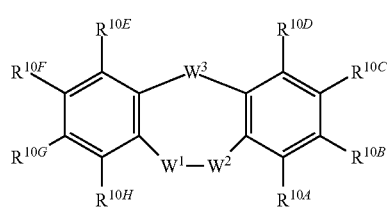

(X)

In formula X, $W_3$ is O, NH, $NCH_2R^{10J}$, $NC(O)CH_2R^{10J}$, $CHCH_2R^{10J}$, C=$CHR^{10J}$, or C=$CHR^{10K}$; $W_1$—$W_2$ is S, O, $OCHR^{10K}$, $SCHR^{10K}$, N=$CR^{10K}$, $CHR^{10L}$—$CHR^{10K}$, or $CR^{10L}$=$CR^{10K}$; each of $R^{10A}$, $R^{10B}$, $R^{10C}$, $R^{10D}$, $R^{10E}$, $R^{10F}$, $R^{10G}$, and $R^{10H}$ is, independently, selected from H, OH, halide, $C_{1-4}$ alkyl, and $C_{2-4}$ heteroalkyl; $R^{10J}$ is $CH_2CH_2X^{10A}$ or $CH(CH_3)CH_2X^{10A}$; $R^{10L}$ is H or OH; $R^{10K}$ is H, OH, or the group:

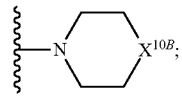

$X^{10A}$ is $NR^{10M}R^{10N}R^{10P}$, or $NR^{10Q}X^{10C}$; $X^{10B}$ is $NR^{10R}R^{10S}$, or $NX^{10C}$; each of $R^{10M}$, $R^{10N}$, $R^{10P}$, $R^{10R}$, and $R^{10S}$ is, independently, selected from $C_{1-4}$ alkyl, $C_{2-4}$ alkenyl, $C_{2-4}$ alkynyl, and $C_{2-4}$ heteroalkyl, or $R^{10R}$, and $R^{10S}$ together complete a heterocyclic ring having at least one nitrogen atom; $R^{10Q}$ is H or $C_{1-4}$ alkyl; $X^{10C}$ is

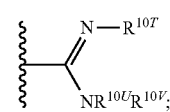

and each of $R^{10T}$, $R^{10U}$, and $R^{10V}$ is, independently, selected from H, C A alkyl, $C_{2-4}$ alkenyl, and $C_{2-4}$ alkynyl, or $R^{10T}$ and $R^{10V}$ together complete a heterocyclic ring having two nitrogen atoms. Where $R^{10T}$ and $R^{10V}$ form a heterocyclic ring having two nitrogen atoms, the resulting guanidine group is, desirably, selected from

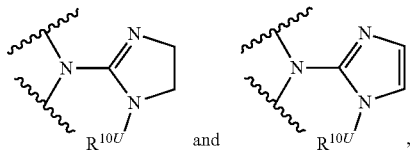

where $R^{10U}$ is H or $CH_3$. Desirably, $R^{10T}$ and $R^{10V}$ combine to form an alkylene or alkenylene of from 2 to 4 carbon atoms, e.g., ring systems of 5, 6, and 7-membered rings. Exemplary compounds of formula X include N-guanidyl derivatives (e.g., —C(NH)NH$_2$ derivatives) and methylated quaternary ammonium derivatives. N-guanidyl derivatives of formula X include, without limitation, N-guanidyl amoxapine, desmethyl-N-guanidyl trimipramine, desmethyl-N-guanidyl dothiepin, desmethyl-N-guanidyl doxepin, desmethyl-N-guanidyl amitriptyline, N-guanidyl protriptyline, N-guanidyl desipramine, desmethyl-N-guanidyl clomipramine, desmethyl-N-guanidyl clozapine, desmethyl-N-guanidyl loxapine, N-guanidyl nortriptyline, desmethyl-N-guanidyl cyclobenzaprine, desmethyl-N-guanidyl cyproheptadine, desmethyl-N-guanidyl olopatadine, desmethyl-N-guanidyl promethazine, desmethyl-N-guanidyl trimeprazine, desmethyl-N-guanidyl chlorprothixene, desmethyl-N-guanidyl chlorpromazine, desmethyl-N-guanidyl propiomazine, desmethyl-N-guanidyl prochlorperazine, desmethyl-N-guanidyl thiethylperazine, desmethyl-N-guanidyl trifluoperazine, desethyl-N-guanidyl ethacizine, and desmethyl-N-guanidyl imipramine. Methylated quaternary ammonium derivatives of formula X include, without limitation, N,N-dimethyl amoxapine, N-methyl trimipramine, N-methyl dothiepin, N-methyl doxepin, N-methyl amitriptyline, N,N-dimethyl protriptyline, N,N-dimethyl desipramine, N-methyl clomipramine, N-methyl clozapine, N-methyl loxapine, N,N-dimethyl nortriptyline, N-methyl cyclobenzaprine, N-methyl cyproheptadine, N-methyl olopatadine, N-methyl promethazine, N-methyl trimeprazine, N-methyl chlorprothixene, N-methyl chlorpromazine, N-methyl propiomazine, N-methyl moricizine, N-methyl prochlorperazine, N-methyl thiethylperazine, N-methyl fluphenazine, N-methyl perphenazine, N-methyl flupenthixol, N-methyl acetophenazine, N-methyl trifluoperazine, N-methyl ethacizine, and N-methyl imipramine. These derivatives can be prepared using methods analogous to those described in Schemes 1-5.

Other ion channel blockers that can contain an amine nitrogen which can be guanylated or quaternized as described herein include, without limitation, orphenadrine, phenbenzamine, bepridil, pimozide, penfluridol, flunarizine, fluspirilene, propiverine, disopyramide, methadone, tolterodine, tridihexethyl salts, tripelennamine, mepyramine, brompheniramine, chlorpheniramine, dexchlorpheniramine, carbinoxamine, levomethadyl acetate, gallopamil, verapamil, devapamil, tiapamil, emopamil, dyclonine, pramoxine, lamotrigine, fendiline, mibefradil, gabapentin, amiloride, diltiazem, nifedipine, nimodipine, nitrendipine, cocaine, mexiletine, propafenone, quinidine, oxethazaine, articaine, riluzole, bencyclane, lifarizine, and strychnine. Still other ion channel blockers can be modified to incorporate a nitrogen atom suitable for quaternization or guanylation. These ion channel blockers include, without limitation, fosphenytoin, ethotoin, phenytoin, carbamazepine, oxcarbazepine, topiramate, zonisamide, and salts of valproic acid.

Examples of these channel blockers, including still other derivatives that can be quaternized or guanylated according to the methods described herein are provided in Table 1.

TABLE 1

| No. | Channel Blocker | Exemplary References |
|---|---|---|
| 1 | orphenadrine | U.S. Pat. No. 2,567,351 (see, e.g., the compounds of Examples 1-6 and the formula described at col. 1, lines 10-24). U.S. Pat. No. 2,991,225 (see, e.g., the structure shown at col. 1, line 25). |
| 2 | phenbenzamine 2339; Antergan ®), | Passalacqua et al., "Structure and Classification of $H_1$-Antihistamines and (RP-Overview of Their Activities," in Histamine and H1-antihistamines in Allergic Disease, F.E.R. Simons, Ed., Informa Health Care (2002). |
| 3 | bepridil | U.S. Pat. No. 3,962,238 (see, e.g., Formulas I-V and compounds 1-6 of Table 1). US RE30577 |
| 4 | pimozide | See, e.g., Janssen et al., Arzneimittel-Forsch. 18:261, 279, 282 (1968), and Journal of Neuroscience, 22(2):396-403 (2002) |
| 5 | penfluridol | U.S. Pat. No. 3,575,990 (see, e.g., the compounds of Formula (I), claims 1-7, and Examples I-XXXIII). |
| 6 | flunarizine | U.S. Pat. No. 3,773,939 (see, e.g., Formula (I) and the compound described at col. 5, line 40). |
| 7 | fluspirilene | U.S. Pat. No. 3,238,216 (see, e.g., the compounds recited in any of claims 1-34). |
| 8 | propiverine | DD 106643 |
| 9 | disopyramide | U.S. Pat. No. 3,225,054 (see, e.g., the compounds of Examples 1-15 and claims 1-3) |
| 10 | methadone | DE711069 U.S. Pat. No. 2,983,757 |
| 11 | tolterodine | U.S. Pat. No. 5,382,600 (see, e.g., Formula (I), the compounds described at col. 3, lines 20-39, in Table 1, and in claims 1-7) |
| 12 | tridihexethyl salts | U.S. Pat. No. 2,913,494 (see, e.g., col. 1, lines 15-22) |

TABLE 1-continued

| No. | Channel Blocker | Exemplary References |
|---|---|---|
| 13 | tripelennamine | U.S. Pat. No. 2,502,151 (see, e.g., Formula (I) and the compounds recited in claims 1-13) |
| 14 | mepyramine (pyrilamine) | U.S. Pat. No. 2,502,151 |
| 15 | brompheniramine | U.S. Pat. No. 2,567,245 (see, e.g., the formula described at col. 1, lines 30-45, the compounds of Examples I-XXI, and the compounds recited in claims 1-15) U.S. Pat. No. 2,676,964 (see, e.g., the formula described at col. 1, lines 5-28, the compounds of Examples I-XLIV, and the compounds recited in claims 1-14) U.S. Pat. No. 3,061,517 (see, e.g., the formula at col. 1, lines 49-67, and the compounds described at col. 2, lines 17-19, col. 2, lines 40-43, col. 4, lines 2-7, and claims 1-6) |
| 16 | chlorpheniramine | U.S. Pat. No. 2,567,245 (see, e.g., the formula described at col. 1, lines 30-45, the compounds of Examples I-XXI, and the compounds recited in claims 1-15) U.S. Pat. No. 2,676,964 (see, e.g., the formula described at col. 1, lines 5-28, the compounds of Examples I-XLIV, and the compounds recited in claims 1-14) |
| 17 | dexchlorpheniramine | U.S. Pat. No. 3,061,517 (see, e.g., the formula at col. 1, lines 49-67, and the compounds described at col. 2, lines 17-19, col. 2, lines 40-43, col. 4, lines 2-7, and claims 1-6)U.S. Pat. No. 2,766,174 (see, e.g., the formula described at col. 1, lines 41-72) |
| 18 | carbinoxamine | U.S. Pat. No. 2,606,195 (see, e.g., the formula described at col. 1, lines 7-24, Examples I-VIII, and in claims 1-3) U.S. Pat. No. 2,800,485 GB 905993 |
| 19 | levomethadyl acetate | Pohland et al., J. Am. Chem. Soc. 71:460 (1949) |
| 20 | gallopamil | U.S. Pat. No. 3,261,859 (see, e.g., Formula (I), Examples 1-28, and claims 1-19) Theodore et al., J. Org. Chem. 52:1309 (1987) |
| 21 | verapamil | U.S. Pat. No. 3,261,859 (see, e.g., Formulas (I) and (IV), Examples 1-28, and claims 1-19) |
| 22 | devapamil | Godfraind, Calcium Channel Blockers, Birkhauser Verlag (January 2004). |
| 23 | tiapamil | |
| 24 | emopamil | |
| 25 | dyclonine | Pofft, Chem. Tech. (Berlin) 4:241 (1952) |
| 26 | pramoxine | U.S. Pat. No. 2,870,151 (see, e.g., the formula described at col. 1, lines 18-25, and the compounds of Examples I-XII and claims 1-13). |
| 27 | lamotrigine | EP21121 U.S. Pat. No. 4,602,017 (see, e.g., Formulas (I)-(III) and the compounds described at col. 2, line 63-col. 3, line 12, Examples 1-5, and claims 1-2) |
| 28 | mibefradil | U.S. Pat. No. 4,808,605 (see, e.g., Formula I described at col. 1, lines 10-33 and the compounds described at col. 3, line 58-col. 7, line 6, Examples 1-41, and claims 1-15). |
| 29 | gabapentin | U.S. Pat. No. 4,024,175 (see, e.g., Formula (I) described at col. 1, lines 5-17, Examples 1-12, and claims 1-11) |
| 30 | amiloride | U.S. Pat. No. 3,313,813 (see, e.g., the compounds described at col. 1, line 13-col.2, line 55, Examples 1-205, and claims 1-31) |

TABLE 1-continued

| No. | Channel Blocker | Exemplary References |
|-----|-----------------|---------------------|
| 31 | diltiazem | U.S. Pat. No. 3,562,257 (see, e.g., Formula (I) described at col. 1, lines 39-64, and the compounds described at col. 2, lines 15-30, Tables 1-3, and claims 1-43) U.S. Pat. No. 4,552,695 (see, e.g., the compound of Formula (I)) |
| 32 | nifedipine | U.S. Pat. No. 3,485,847 (see, e.g., the Formula described at col. 1, line 40-col. 2, line 6, the compounds of Examples 1-6, and claims 1-27) |
| 33 | nimodipine | U.S. Pat. No. 3,799,934 (see, e.g., the Formula described at col. 1, lines 39-69, the compounds described at col. 4, line 50-col. 5, line 16, Examples 1-53, and claims 1-13) |
| 34 | nitrendipine | |
| 35 | mexiletine | U.S. Pat. No. 3,954,872 (see, e.g., Formula (I) described at col. 1, lines 14-35, and the compounds of Examples 1-6 and claims 1-4) |
| 36 | propafenone | DE2001431 (see, e.g., claims 1-4) |
| 37 | quinidine | Turner et al., The Alkaloids, Vol. 3, 1-63 (1953) Mason et al., Ann. N.Y. Acad. Sci. 432:162-176 (1984) |
| 38 | oxethazaine | U.S. Pat. No. 2,780,646 (see, e.g., the formula described at col. 1, lines 18-42, and the compounds of Examples 1-14 and claims 1-8) |
| 39 | articaine | Becker et al., Anesth Prog. 53(3): 98-109 (Fall 2006) |
| 40 | riluzole | U.S. Pat. No. 4,370,338 (see, e.g., the compound described at col. 1, line 15) |
| 41 | bencyclane | HU 151865 |
| 42 | lifarizine | Grauert et al., J. Med. Chem. 45(17):3755-3764 (2002) |
| 43 | strychnine | Makarevich et al., "Quaternary salts of alkaloids,"Vol. 42, pages 473-476, Chemistry of Natural Compounds, Springer New York: 2006. |
| 44 | fendiline | U.S. Pat. No. 3,262,977 (see, e.g., Formula (I), Examples 1-9, and the compounds of claims 1-9) |

Calcium-Channel Blockers

Exemplary cationic calcium channel blockers include D-890, CERM 11888, N-methyl-verapamil, N-methylgallopamil, N-methyl-devapamil, and dodecyltrimethylammonium. Other exemplary compounds include any charged derivative, e.g., a quarternary amine derivative, of verapamil, gallopamil, devapamil, diltiazem, fendiline, mibefradil, terpene compounds (e.g., sesquiterpenes) such as those described in Norman et al. *Agricultural and Biological Chemistry* 49(10):2893-8 (1985), and other inhibitors of calcium channels (see, for example, Triggle, *European Journal of Pharmacology*, 375:311-325 (1999), Eller et al., *British Journal of Pharmacology*, 130:669-677 (2000), and Yamamoto et al., *Current Topics in Medicinal Chemistry*, 9:377-395 (2009), which can be prepared according to the methods described herein.

For example, Yamamoto et al. provides the following N-type calcium channel blockers (Table 2), which can be modified (e.g., quaternized or guanylated) according to the methods described herein.

TABLE 2

| No. | Channel Blocker | Exemplary References |
|-----|-----------------|---------------------|
| 45 | 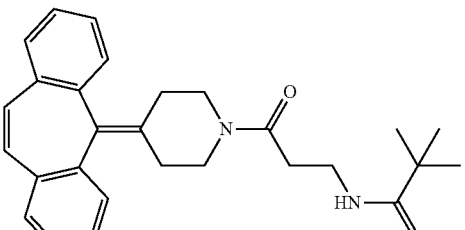 | Yamamoto et al., *Bioorg. Med. Chem.* 14: 5333-5339 (2006). |
| 46 | 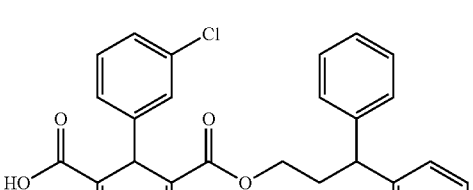 | Yamamoto et al., *Bioorg. Med. Chem. Lett.* 16: 798-802 (2006). |

TABLE 2-continued

| No. | Channel Blocker | Exemplary References |
|---|---|---|
| 47 | | Yamamoto et al., *Bioorg. Med. Chem. Lett.* 18: 4813-4815 (2008). |
| 48 | | See, e.g., WO08143263 and EP2149560 (e.g., Formula (I), the compounds of Tables 6-35, 43-110, 126-127, and the compounds of claims 1-6) |
| 49 | | Miller et al., *Soc. Neurosci. Abstr.* 25 (Part 2): 896.3 (1999) |
| 50 | | WO0236567 (see, e.g., formulas I-IV, the compounds of Table 2 (Examples 1-111), and claims 1-5) |
| 51 | | Zhang et al., *Eur. J. Pharmacol.* 587: 24-47 (2008) |

TABLE 2-continued

| No. | Channel Blocker | Exemplary References |
|---|---|---|
| 52 | | Baell et al., *Bioorg. Med. Chem.* 12: 4025-4037 (2004) |
| 53 | | Yamamoto et al., *22nd National Meeting of American Chemical Society*, American Chemical Scoiety: Washington, DC: Chicago, IL 2001; Kaneda et al, *Soc. Neurosci. Abstr.* 27: 332.15 (2001); Niidome et al., *Soc. Neurosci. Abstr.* 27: 332.14 (2001); and Suzuki et al., *Bioorg. Med. Chem. Lett.* 13: 919-922 (2003). |
| 54 | E-2051 | Kaneda, *Soc. Neurosci. Abstr.* 28: 490.1 (2002) |
| 55 | | WO07110449 (see, e.g., Formulas I-XIII, the compounds described at Paragraphs [0181]-[0183] and Examples 1-14, and claims 1-72) |
| 56 | | WO06040181 (see, e.g., Formulas I-X, the compounds described at Paragraphs [0105]-[0109] and Examples 1-37, and in claims 1-56) |
| 57 | | WO07118853 (see, e.g., Formulas I-XIII, the compounds described at Paragraph [0320] and Examples 1-19, and the compounds of claims 1-165) |

TABLE 2-continued

| No. | Channel Blocker | Exemplary References |
| --- | --- | --- |
| 58 | | WO07085357 (see, e.g., Formulas I-VII, the compounds described at Paragraphs [0065]-[0067], Examples 1-6, and claims 1-16) |
| 59 | | WO07028638 (see, e.g., Formulas I-XXVI, the compounds described at Paragraphs [0119]-[0123], Examples 1-24, and claims 1-20 |
| 60 | | WO07118854 (see, e.g., Formulas I-VII and the compounds of Examples 1-11 and claims 1-36) |
| 61 | | WO08008398 (see, e.g., Formulas I, I', I'', II, and II'; Examples 1-377, and claims 1-7) |
| 62 | | WO08150447 (see, e.g., Formulas I, I', I'', and the compounds of Examples 1-135 and claims 1-5 |

TABLE 2-continued

| No. | Channel Blocker | Exemplary References |
|---|---|---|
| 63 | | Knutsen et al., *Bioorg. Med. Chem. Lett.* 17: 662-667 (2007) |
| 64 | | O'Neill, *Brain Res.* 888: 138-149 (2001); Hicks et al., *Eur. J. Pharmacol.* 408: 241-248 (2000) |
| 65 | | WO07084394 (see, e.g., the compounds of Formulas 1 and Ia-Ig, and the compounds of Examples 1-11 and claims 1 and 2) |
| 66 | | WO08066803 (see, e.g., Formulas I and II, the compound of Example 1, and claims 1-11) |
| 67 | | WO07075524 (see, e.g., Formulas (I), (Ia)-(Ie), the compounds of Examples 1-184, and claims 1-16) |
| 68 | | WO08133867 (see, e.g., Formulas (I) and (II), the compounds of Examples 1-163, and claims 1-16) |

TABLE 2-continued

| No. | Channel Blocker | Exemplary References |
|---|---|---|
| 69 | | WO01045709 (see, e.g., Formula (1), the compounds of Example 4, and claims 24-38) WO06105670 (see, e.g., Formula (1), the compounds described at Paragraphs [0065] and [0066], and claims 1-13) |
| 70 | | WO04089377 (see, e.g., Formula (1), Examples 1-5, original claims 1-13, and amended claims 1-17) |
| 71 | | WO07071035 (see, e.g., Formula (1), the compounds of Examples 1-18, and claims 20-35) |
| 72 | | WO08043183 (see, e.g., Formulas (1) and (2), the compounds of Examples 1-16, and claims 16-28) |
| 73 | | WO04089922 (see, e.g., Formulas (1)-(4), the compounds of Examples 1-9, claims 1-17, and the compounds of FIG. 1) |

TABLE 2-continued

| No. | Channel Blocker | Exemplary References |
| --- | --- | --- |
| 74 | | WO04105750 (see, e.g., Formulas (l)-(8), the compounds of Examples 1-10, claims 1-23, and FIG. 1) |
| 75 | | WO08031227 (see, e.g., Formulas (1) and (2), the compounds of Examples 1-20, and claims 21-37) |
| 76 | | Tatsumi et al., *Jpn. J. Pharmacol.* 73: 193 (1997); Aoki et al., *Brain Res.* 890: 162-169 (2001); Katsumata et al., *Brain Res.* 969: 168-174 (2003); Tamura et al., *Brain Res.* 890: 170-176 (2001); Shi et al., *J. Thorac. Cardiovasc. Surg.* 129: 364-371 (2005); Small, *IDrugs*, 3: 460-465 (2000); Suma et al., *Jpn. J. Pharmacol.* 73: 193 (1997); Shimidzu et al., *Naunyn Schmiedebergs Arch. Pharamcol.* 355: 601-608 (1997); and Suma et al., *Eur. J. Pharmacol.* 336: 283-290 (1997). |
| 77 | | Seko et al, *Bioorg. Med. Chem. Lett.* 11: 2067-2070 (2001) |

TABLE 2-continued
| No. | Channel Blocker | Exemplary References |
|---|---|---|
| 78 | 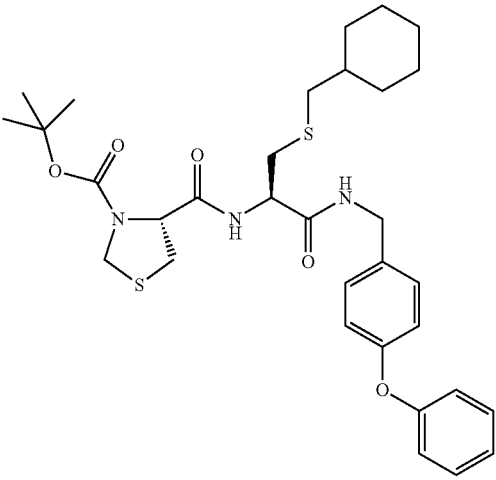 [SMILES: CC(C)(C)OC(=O)N1CSC[C@H]1C(=O)N[C@@H](CSCC1CCCCC1)C(=O)NCc1ccc(Oc2ccccc2)cc1] | Seko et al., *Bioorg. Med. Chem.* 11: 1901-1913 (2003). Seko et al., *Bioorg. Med. Chem. Lett.* 12: 915-918 (2002) |
| 79 | 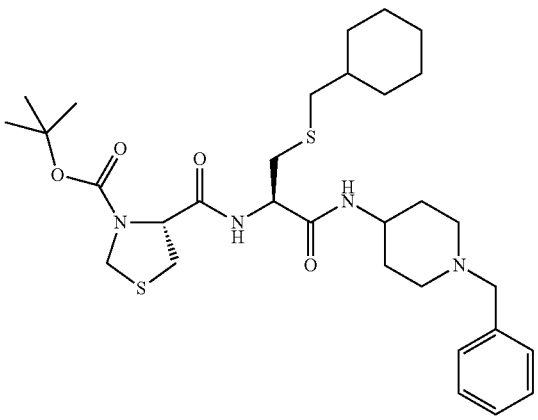 [SMILES: CC(C)(C)OC(=O)N1CSC[C@H]1C(=O)N[C@@H](CSCC1CCCCC1)C(=O)NC1CCN(Cc2ccccc2)CC1] | Seko et al., *Bioorg. Med. Chem. Lett.* 12: 2267-2269 (2002) |
| 80 | 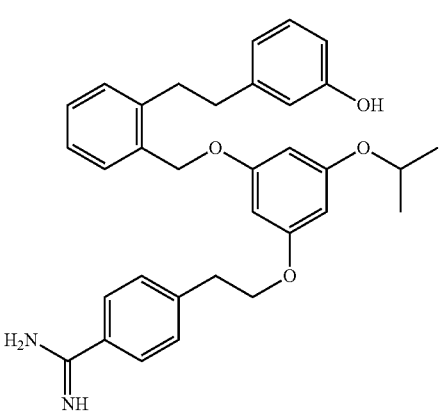 [SMILES: CC(C)Oc1cc(OCCc2ccc(C(=N)N)cc2)cc(OCc2ccccc2CCc2cccc(O)c2)c1] | Menzler et al., *Bioorg. Med. Chem. Lett.* 10: 345-347 (2000) |

TABLE 2-continued
| No. | Channel Blocker | Exemplary References |
|---|---|---|
| 81 | 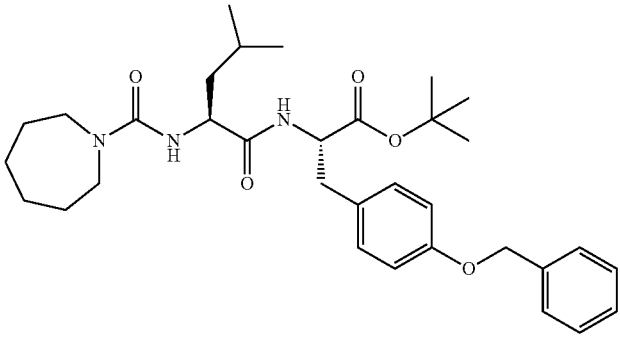 [SMILES: CC(C)C[C@H](NC(=O)N1CCCCCC1)C(=O)N[C@@H](Cc1ccc(OCc2ccccc2)cc1)C(=O)OC(C)(C)C] | Malone et al., 217th National Meeting of the American Chemical Society, American Chemical Society: Washington DC: Anaheim CA 1999; Hu et al., J. Med. Chem. 42: 4239-4249 (1999) |
| 82 | 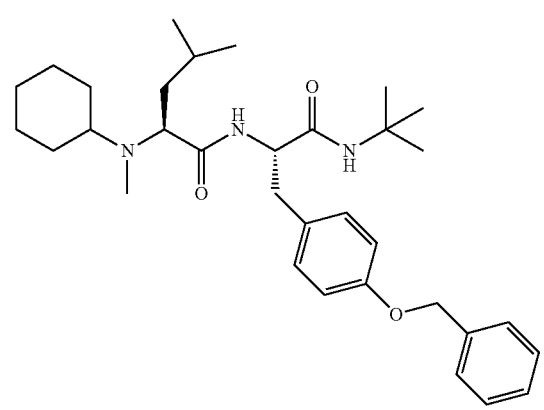 [SMILES: CC(C)C[C@@H](C(=O)N[C@@H](Cc1ccc(OCc2ccccc2)cc1)C(=O)NC(C)(C)C)N(C)C1CCCCC1] | Hu et al., Bioorg. Med. Chem. Lett. 9: 907-912 (1999) |
| 83 | 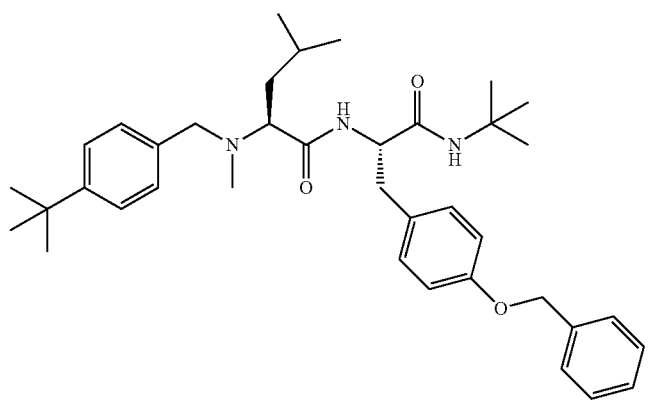 [SMILES: CC(C)C[C@@H](C(=O)N[C@@H](Cc1ccc(OCc2ccccc2)cc1)C(=O)NC(C)(C)C)N(C)Cc1ccc(C(C)(C)C)cc1] | Hu et al., Bioorg. Med. Chem. Lett. 9: 2151-2156 (1999) Ryder et al., Bioorg. Med. Chem. Lett. 9: 1813-1818 (1999) |
| 84 | 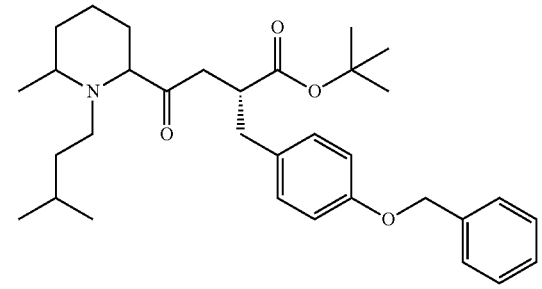 [SMILES: CC(C)CCN1C(C)CCCC1C(=O)C[C@@H](Cc1ccc(OCc2ccccc2)cc1)C(=O)OC(C)(C)C] | Hu et al., Bioorg. Med. Chem. Lett. 9: 1121-1126 (1999) |

TABLE 2-continued

| No. | Channel Blocker | Exemplary References |
|---|---|---|
| 85 | | Bennett et al., *Pain* 33: 87-107 (1988) |
| 86 | | Hu et al., *Bioorg. Med. Chem.* 8: 1203-1212 (2000) |
| 87 | | Hu et al., *Bioorg. Med. Chem.* 8: 1203-1212 (2000) |
| 88 | | Hu et al., *J. Med. Chem.* 42: 4239-4249 (1999) |
| 89 | | Schelkun et al., *Bioorg. Med. Chem. Lett.* 9: 2447-2452 (1999). |

TABLE 2-continued
| No. | Channel Blocker | Exemplary References |
|---|---|---|
| 90 | 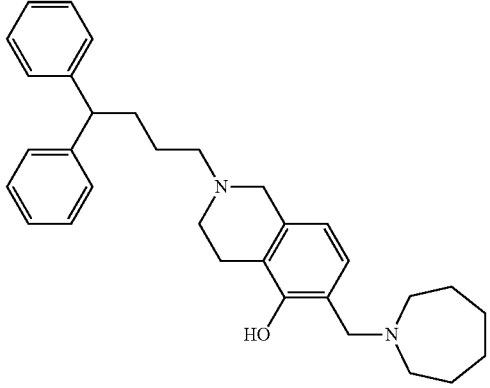 [SMILES: Oc1c(CN2CCCCCC2)ccc2c1CCN(CCCC(c1ccccc1)c1ccccc1)C2] | Yuen et al., *Bioorg. Med. Chem. Lett.* 8: 2415-2418 (1998) |
| 91 | 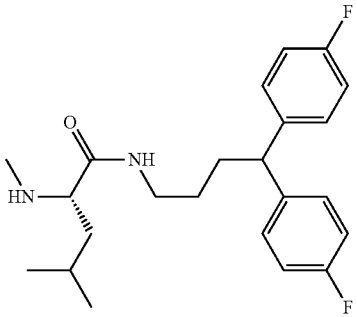 [SMILES: CN[C@@H](CC(C)C)C(=O)NCCCC(c1ccc(F)cc1)c1ccc(F)cc1] | Song et al., *J. Med. Chem.* 43: 3474-3477 (2000) |
| 92 | 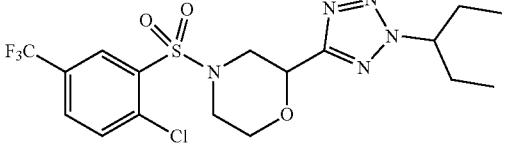 | WO07125398 (see, e.g., Formula (I), the compounds of Examples 1-29, and claims 1-9) |
| 93 | 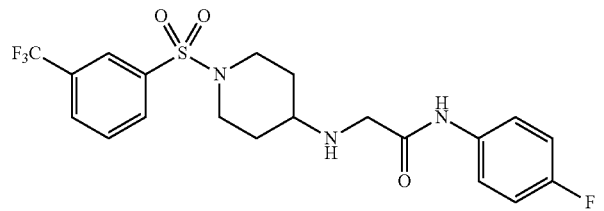 [SMILES: O=C(CNC1CCN(S(=O)(=O)c2cccc(C(F)(F)F)c2)CC1)Nc1ccc(F)cc1] | WO08124118 (see, e.g., Formula I-VI, the compounds of Paragraphs [0129] and Examples 1-5, and claims 1-42) |
| 94 | 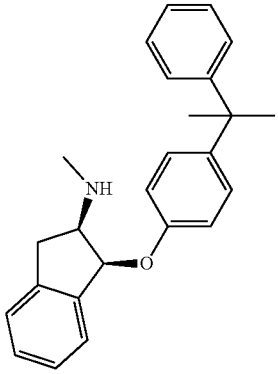 [SMILES: CN[C@@H]1Cc2ccccc2[C@@H]1Oc1ccc(C(C)(C)c2ccccc2)cc1] | Campbell et al., *Eur. J. Pharmacol.* 401: 419-428 (2000) |

TABLE 2-continued

| No. | Channel Blocker | Exemplary References |
| --- | --- | --- |
| 95 | | Teodori et al., *J. Med. Chem.* 47: 6070-6081 (2004) |
| 96 | | Teodori et al., *J. Med. Chem.* 47: 6070-6081 (2004) |
| 97 | | Schroeder et al., *Mol. Divers.* 8: 127-134 (2004). |
| 98 | | WO06030211 (see, e.g., Formula (I), the compounds described at page 9, line 17-page 15, line 12, Examples 1-99, and claims 1-12) |

Farnesyl Amine Compounds

Compounds having a structure according to Formula (XI) can also be used in the invention as calcium channel blockers.

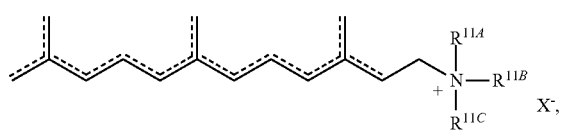

(XI)

where each $R^{11A}$, $R^{11B}$, and $R^{11C}$ is selected, independently, from H or $C_{1-4}$ alkyl, and where 0, 1, 2, or 3 of the dashed bonds represents a carbon-carbon double bond (i.e., compounds of Formula (XI) can include 0, 1, 2, or 3 double bonds), provided that when 2 or 3 carbon-carbon double bonds are present, the double bonds are not adjacent to one another. Compounds that include 0, 1, or 2 double bonds can be prepared according to methods known in the literature, e.g., partial or total hydrogenation of the parent triene.

In some embodiments, compounds of Formula (XI) can be represented by the following formula (XI-A), (XI-A)

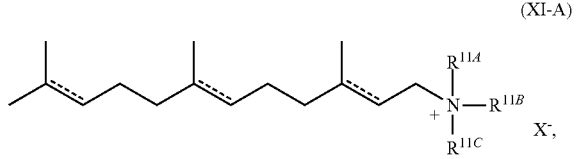

where each $R^{11A}$, $R^{11B}$, $R^{11C}$, and X is according to Formula (XI), and where each dashed bond represents an optional carbon-carbon double bond.

Still other farnesyl amine compounds can include those compounds that have a structure according to Formula (XI-B), (XI-B)

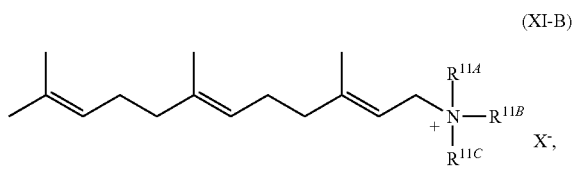

where each $R^{11A}$, $R^{11B}$, $R^{11C}$, and X is according to Formula (XI).

Exemplary compounds of Formula (XI) include (99)

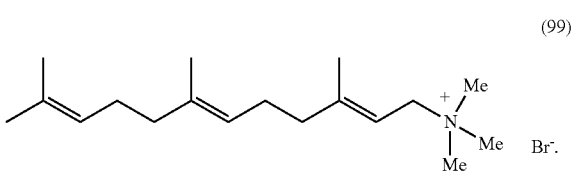

Cysteine-Derived Compounds

Amino acid derivatives, e.g., those described in U.S. Pat. No. 7,166,590 or in Seko et al., *Bioorg. Med. Chem. Lett.* 11(16):2067-2070 (2001), each of which is herein incorporated by reference, can also be used in the invention. For example, compounds having a structure according to Formula (XII) can be N-type calcium channel blockers.

(XII)

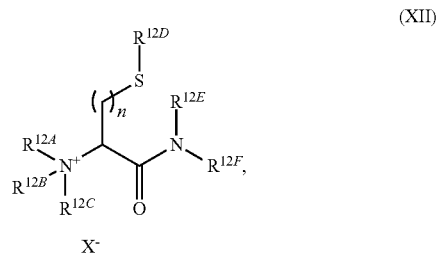

wherein each of $R^{12A}$, $R^{12B}$, $R^{12C}$, and $R^{12D}$ is, independently, selected from $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, and $C_{3-10}$ alkheterocyclyl; or $R^{12A}$ and $R^{12B}$ together complete a heterocyclic ring having at least one nitrogen atom, n is an integer between 1-5, each of $R^{12E}$ and $R^{12F}$ is, independently, selected from H, $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, or $C_{3-10}$ alkheterocyclyl, and X is any pharmaceutically acceptable anion.

Exemplary compounds of Formula (XII) include (100)

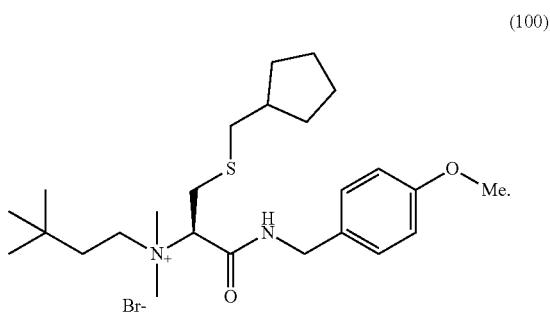 [SMILES: COc1ccc(CNC(=O)[C@H](CSCC2CCCC2)[N+](C)(C)CCC(C)(C)C)cc1 ; [Br-]]

Flunarizine and Related Compounds

Still other compounds that can be used in the invention are charged derivatives of flunarizine and related compounds (see, e.g., U.S. Pat. Nos. 2,883,271 and 3,773,939, as well as Zamponi et al., *Bioorg. Med. Chem. Lett.* 19: 6467 (2009)), each of which is hereby incorporated by reference. For example, compounds according to Formulas (XIII-A), (XIII-B), and (XIII-C) can be prepared according to, e.g., Zamponi et al., and used in the invention, (XIII-A)

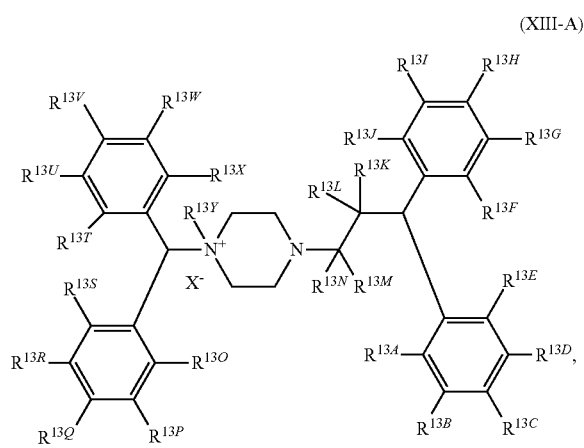

(XIII-B)

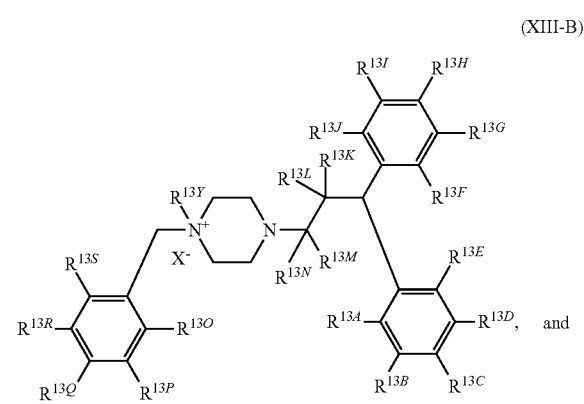

and

-continued
(XIII-C)

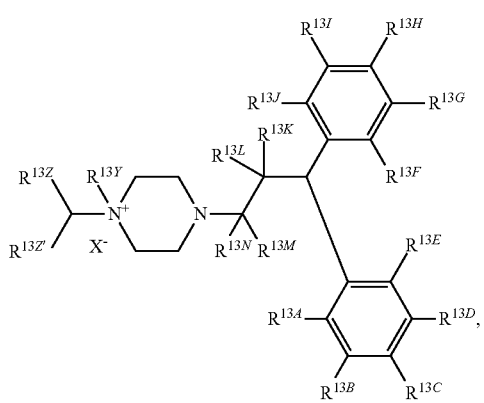

where each $R^{13A}$-$R^{13J}$ and $R^{13O}$-$R^{13T}$ is selected, independently, from H, halogen, $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, and $C_{3-10}$ alkheterocyclyl, $OR^{13AA}$, $NR^{13AB}R^{13AC}$, $NR^{13AD}C(O)R^{13AE}$, $S(O)R^{13AF}$, $SO_2R^{13AG}R^{13AH}$, $SO_2NR^{13AI}R^{13AJ}$, $SO_3R^{13AK}$, $CO_2R^{13AL}$, $C(O)R^{13AM}$, and $C(O)NR^{13AN}R^{13AO}$; and each of $R^{3AA}$-$R^{13AO}$ is, independently, selected from H, $C_{1-4}$ alkyl, $C_{2-4}$ alkenyl, $C_{2-4}$ alkynyl, and $C_{2-4}$ heteroalkyl;

each $R^{13K}$, $R^{13L}$, $R^{13M}$, and $R^{13N}$ is, independently, H or $C_{1-4}$ alkyl, or $R^{13K}$ and $R^{13L}$, or $R^{13M}$ and $R^{13N}$, combine to form C=O, or $R^{13K}$ and $R^{13M}$ combine to form C=C;

$R^{13Y}$ is H or $C_{1-4}$ alkyl;

$R^{13Z}$ and $R^{13Z'}$ are, independently, selected from H, halogen, $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, and $C_{3-10}$ alkheterocyclyl; and $X^-$ is any pharmaceutically acceptable anion.

Exemplary compounds according to Formulas (XIII-A)-(XIII-C) include (101)

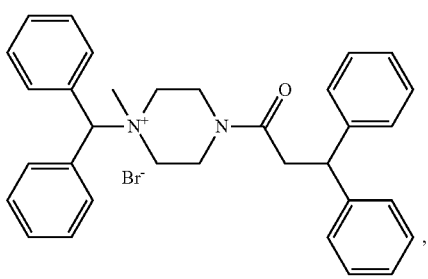

(102)

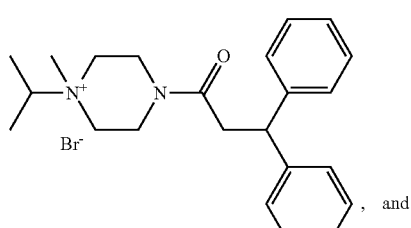
, and (103)

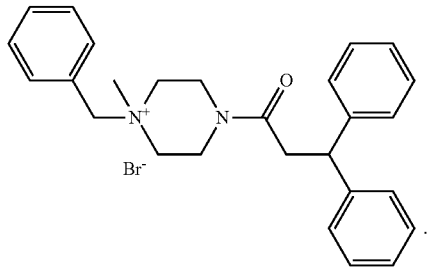
.

Mibefradil Derivatives

Derivatives of mibrefradil, such as those described in U.S. Pat. No. 4,808,605, hereby incorporated by reference can also be used. Exemplary mibrefadil derivatives include compounds of Formula (XIV), (XIV)

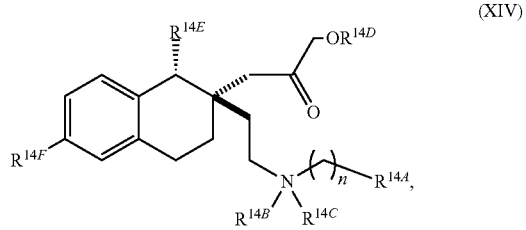

where
n is an integer between 0-5;
$R^{14A}$ is heterocyclyl (e.g., a heteroaryl such as benzimidazole),
each of $R^{14B}$, $R^{14C}$, $R^{14D}$, and $R^{14E}$ is, independently, $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, and $C_{3-10}$ alkheterocyclyl; and
$R^{14F}$ is selected from H, halogen, $C_{1-4}$ alkyl, $C_{2-4}$ alkenyl, $C_{2-4}$ alkynyl, $C_{2-4}$ heteroalkyl, $C_{7-14}$ alkaryl, $C_{3-10}$ alkcycloalkyl, and $C_{3-10}$ alkheterocyclyl, $OR^{14G}$, $NR^{14H}R^{14I}$, $NR^{14J}C(O)R^{14K}$, $S(O)R^{14L}$, $SO_2R^{14M}R^{14N}$, $SO_2NR^{14O}R^{14P}$, $SO_3R^{14Q}$, $CO_2R^{14R}$, $C(O)R^{14S}$, and $C(O)NR^{14T}R^{14V}$; and each of $R^{14G}$-$R^{13AO}$ is, independently, selected from H, $C_{1-4}$ alkyl, $C_{2-4}$ alkenyl, $C_{2-4}$ alkynyl, and $C_{2-4}$ heteroalkyl.

An exemplary compound of Formula (XIV) is (104)

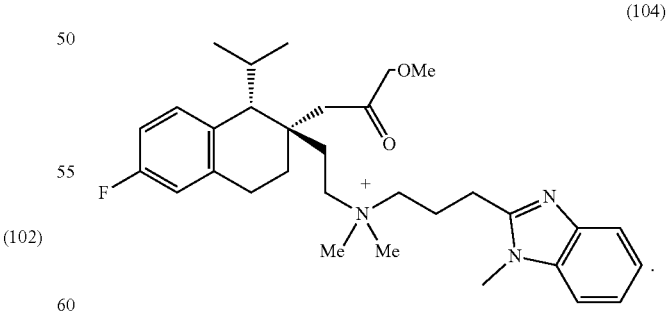
.

4-Piperidinylaniline Compounds

Charged derivatives of 4-piperidinylaniline compounds (e.g., Compounds (86)-(88) of Table 2) can be prepared according to methods known in the literature and described herein. For example, charged N-alkyl derivatives (e.g., N-methyl) of Compounds (86)-(88) can be prepared and used in the compositions, methods, and kits described herein.

Still other channel blockers that can be quaternized or guanylated according to the methods described herein are described, for example, in PCT Publication No. WO 2004/093813 (see, e.g., Tables 5, 6, and 8), which is herein incorporated by reference. For example, the channel blockers shown in Table 3 can be quaternized or guanylated as described herein.

TABLE 3

| No. | Channel Blocker | Exemplary References |
|---|---|---|
| 105 | Isradipine | |
| 106 | Nickel Chloride | |
| 107 | A-53930A | JP 08208690 |
| 108 | AE-0047 Watanidipine dihydrochloride | EP 00424901 |
| 109 | AGN-190604 | Inflammation, 19(2):261-275 (1995) |
| 110 | AGN-190744 | EP372940 |
| 111 | AH-1058 | European Journal of Pharmacology, 398(1):107-112 (2000) |
| 112 | AHR 5360C | European Journal of Pharmacology 146(2-3): 215-22 (1988) |
| 113 | AHR 12234 | Archives Internationales de Pharamcodynamie et de Therapie 301:131-50 (1989) |
| 114 | AHR-12742 | ZA 08604522 |
| 115 | AHR-16303B | Journal of Cardiovascular Pharmacology 17(1):134-44 (1991) |
| 116 | AHR-16462B | Drug Development Research, 22(3): 259-271 (1991) |
| 117 | AIT 110 | |
| 118 | AIT 111 | |
| 119 | AJ 2615 | WO 8601203 A1 |
| 120 | AJ-3941 | Arzneimittel Forschung 46(6):567-71 (1996) |
| 121 | (+)-alismol | JP 04077420 A2 |
| 122 | AM-336 (synthetic version of CVID marine cone snail venom) | WO9954350 |
| 123 | AM 543 | |
| 124 | amlodipine | U.S. Pat. No. 4,572,902 |
| 125 | S-(−)amlodipine | GB 2233974 A1 |
| 126 | AN 132 | EP 196648 |
| 127 | animpamil LU 42668 | EP 64158 A1 |
| 128 | antioquine (alkaloid from stem bark) | Journal of natural Products 55(9):1281-6 (1992) |
| 129 | AP-1067 | IDDB 268934 |
| 130 | AQ-AH-208 | CH 645628 A |
| 131 | AR 12456 (derivative of trapidil) | BE 902218 A1 Cardiovascular Drug Reviews 9(4):385-397 (1991) |
| 132 | aranidipine | U.S. Pat. No. 4,446,325 |
| 133 | atosiban | EP 00112809 |
| 134 | azenidipine CS 905 | EP 88266922 |
| 135 | B 84439 | EP 240828 |
| 136 | barnidipine (derivative of nicardipine) | U.S. Pat. No. 4,220,649 DE 02904552 |
| 137 | BAY-E-6927 | DE 2117571 |
| 138 | BAY-K-9320 | EP 9206 |
| 139 | BAY-T-7207 | |
| 140 | BBR-2160 | EP 28204 A2 |
| 141 | BDF 8784 | EP 25111 |
| 142 | belfosdil/BMY 21891/SR7037 | EP 173041 A1 |
| 143 | Bencylealne/EGYT-201 | FR 151193 |
| 144 | benipidine/KW3049/Nakadipine | U.S. Pat. No. 4,448,964 |
| 145 | bepridil | U.S. Pat. No. 3,962,238 |
| 146 | bisaramil/RGH 2957 | WO 9622096 |
| 147 | BK 129 | Methods and Findings in Experimental and Clinical Pharamcology 14(3):175-81 (1992) |

TABLE 3-continued

| No. | Channel Blocker | Exemplary References |
|---|---|---|
| 148 | BMS-181102 | EP 559569 |
| 149 | BMS-188107 | U.S. Pat. No. 5,070,088 |
| 150 | BMY 20014 | DE 3512995 A1 |
| 151 | BMY 20064 | DE 3512995 A1 |
| 152 | BMY-43011 | Bioorganic and Medicinal Chemistry Letters, 3(12):2817-2820 (1993) |
| 153 | BN 50149 | WO 9323082 |
| 154 | BN 50175 | WO 9323082 |
| 155 | BN 50394 | WO 9323082 |
| 156 | BR 1022 | Current Science 83(4):426-431 (2002) |
| 157 | BRL 3287A | WO 9323082 |
| 158 | BRL-32872 | WO 09323024 |
| 159 | buflomedil | U.S. Pat. No. 4,326,083 |
| 160 | butoprozine | DE 2707048 |
| 161 | CAF 603 | Organic and Bioorganic Chemistry, 22:3349:52 (1994) |
| 162 | calciseptine (venom polypeptide) | WO 2000 069900 |
| 163 | calcium antagonists | WO 9205165 |
| 164 | calcium channel antagonists | WO 00236586 WO 0236567 |
| 165 | calcium channel blocker (L-type) | Journal of Medicinal Chemistry, 39(15):2922-2938 (1996) |
| 166 | calcium channel blockers | EP 400665 A2 U.S. Pat. No. 4,965,356 |
| 167 | calcium channel blockers | WO 9526325 |
| 168 | carvedilol | U.S. Pat. No. 4,503,067 |
| 169 | caryachine | British Journal of Pharmacology, 116(8):3211-8 (1995) |
| 170 | CD-349 | EP 92936 A1 |
| 171 | CD-832 | EP 00370821 |
| 172 | CER-2 metabolite of furnipidine | WO 9919302 |
| 173 | cerebrocrast | DE 3534385 |
| 174 | CERM 11956 | EP 138684 |
| 175 | CERM-12816 | IDDB 283075 |
| 176 | CGP 22442 | WO 9323082 |
| 177 | CGP 26797 | WO 9323082 |
| 178 | CGP 28727 | WO 9323082 |
| 179 | CGP 32413 | WO 9323082 |
| 180 | changrolin | Sci. Sin. (Engl. Ed.) 22(10):1220-8 (1979) |
| 181 | CHF-1521 (combination of delapril and manidipine) | |
| 182 | cilnidipine | U.S. Pat. No. 4,672,068 |
| 183 | cinnarizine | U.S. Pat. No. 3,799,934 |
| 184 | civamide | WO 9640079 U.S. Pat. No. 5,840,762 |
| 185 | clentiazem/TA3090 | EP 00127882 U.S. Pat. No. 4,567,175 |
| 186 | clevidipine | WO 9512578 |
| 187 | CNS-1067 | IDdb 211675 |
| 188 | CNS-1237 | Annals of the New York Academy of Sciences, 765 (Neuroprotective Agents):210-29 (1995) |
| 189 | CNS-2103 (from spider venom) | WO 9214709 A2 |
| 190 | COR 28-22 | WO 9323082 |
| 191 | COR 2707C | WO 9323082 |
| 192 | COR 3752C | WO 9323082 |
| 193 | CP-060S | WO 9500471 A1 |
| 194 | CPC-301 | IDdb 231888 |
| 195 | CPC 304 | IDdb 185705 |
| 196 | CPC-317 | IDdb 185700 |
| 197 | CPU 23 | Yaoxue Xuebao, 25(11): 815-23 (1990) CAN 114:143097 |
| 198 | CPU-86017 | EP 00538844 |
| 199 | CRE 202 | WO 9323082 |
| 200 | CRE 204 | WO 9323082 |
| 201 | CRE 1005 | WO 9323082 |
| 202 | CRL-42752 | WO 00003987 |
| 203 | cronidipine (LF 2-0254) | EP 240398 A1 |
| 204 | CV 159 | FR 2511370 A1 |
| 205 | D-2024 (verapamil(S)) | WO 09509150 |
| 206 | D2603 | WO 9323082 |

TABLE 3-continued

| No. | Channel Blocker | Exemplary References |
|---|---|---|
| 207 | dagapamil | WO 9323082 |
|  |  | EP 64158 A1 |
| 208 | darodipine PY108068 | EP 00000150 |
| 209 | dauricine NSC 36413 | Acta Pharmacologica Sinica 7(6): 543-7 (1986) |
| 210 | desmethyl verapamil |  |
| 211 | DHM 9 | WO 8604581 A1 |
| 212 | DHP 218/PAK 9 | EP 00121117 |
| 213 | diclofurime | DE 79-29227999 |
| 214 | dihydropyridine calcium channel blockers | Journal of Medicinal Chemistry 41(4):509-514 (1998) |
| 215 | diltiazem | U.S. Pat. No. 3,562,257 |
| 216 | diperdipine | EP 00218996 |
| 217 | diptluzine | DE 3318577 A1 |
| 218 | diproteverine BRL 40015 | BE 866208 |
| 219 | dopropidil | EP 00031771 |
| 220 | dotarizinc/FI 6026 | U.S. Pat. No. 4,883,797 |
| 221 | DTZ-323 | Molecular Pharmacology, 51(2):262-268 (1997) |
| 222 | E-2050 | JP 2001199949 A2 |
| 223 | E 4080 | EP 344577 A2 |
| 224 | cfonidipine hydrochloride | U.S. Pat. No. 4,885,284 |
| 225 | EG 1088 | EP 56637 A1 |
| 226 | EGIS 3966 | DE 4027052 A1 |
| 227 | eglodipine | DE 3825962 A1 |
| 228 | emopamil (racemic) SZ 45 | DE 3344755 A1 |
| 229 | (S)-emopamil | DE 3344755 A1 |
| 230 | enalapril_nitrendipine, Vita-Inveest | EP 00884054 |
| 231 | etafenonee LG 11457 | DE 1265758 |
| 232 | ethosuximide |  |
| 233 | eugenodilol | JP 11255719 A2 |
| 234 | evodiamine | JP 52077098 |
| 235 | F-0401 | EP 00320984 |
| 236 | falipamil AQA 39 | Journal of Medicinal Chemistry, 33(5):1496-504 (1990) |
| 237 | fantofarone SR 33557 | EP 235111 A1 |
|  |  | U.S. Pat. No. 4,957,925 |
| 238 | fasudil (iv formulation), Asahi | U.S. Pat. No. 4,678,783 |
| 239 | FCE-24265 | EP 373645 A1 |
| 240 | FCE-26262 |  |
| 241 | FCE-27335 |  |
| 242 | FCE-27892 |  |
| 243 | FCE-28718 | EP 00755931 |
| 244 | fedopamil |  |
| 245 | felodipine | U.S. Pat. No. 4,264,611 |
| 246 | felodipine + ramipril (Astra/Aventis) | WO 09607400 |
| 247 | fendiline | U.S. Pat. No. 3,262,977 |
| 248 | feniline |  |
| 249 | flezelastine, D 18024 | EP 590551 A2 |
| 250 | flordipine |  |
| 251 | fluodipine | U.S. Pat. No. 3,773,939 |
| 252 | fluphenazine, S94 SQ 4918 Triflumethazine Vespazine | Journal of Medicinal Chemistry, 19(6):850-2 (1976) |
| 253 | fostedil KB944 | EP 10120 |
| 254 | FPL 62129 | EP 125803 A2 |
| 255 | FR 46171 |  |
| 256 | FR-172516 | JP 09040647 |
| 257 | FRC 9411 |  |
| 258 | FRG 8653 |  |
| 259 | FRG-8701 |  |
| 260 | furaldipine |  |
| 261 | fumidipine (CRE 319) | Journal of Medicinal Chemistry, 38(15):2830-41 (1995) |
| 262 | GOE 5057 |  |
| 263 | GOE 5584 A | EP 173933 A1 |
| 264 | GOE 93007 |  |
| 265 | GR 60139 |  |
| 266 | GR 55234A (R-enantiomer of telupidine) | Haemotalogica, 79(4):328-33 (1994) |
| 267 | GR 55235A (L-enantiomer of telupidine) | Haemotalogica, 79(4):328-33 (1994) |
| 268 | GS-386 |  |
| 269 | GYKI 46544 |  |
| 270 | H32438 |  |
| 271 | HA 22 | U.S. Pat. No. 5,240,947 |
| 272 | HA 23 | U.S. Pat. No. 5,240,947 |
| 273 | HA 1004 |  |
| 274 | GA 1077 |  |
| 275 | HE 30346 |  |
| 276 | HNS 32 | JP 08311007 A2 |
| 277 | HOE 166 | Molecular Pharmacology 33(4):363-9 (1988) |
| 278 | HOE 263 |  |
| 279 | HP 406 | U.S. Pat. No. 4,521,537 |
| 280 | ICI 206970 | EP 293170 A1 19881130 |
| 281 | iganidipine | JP 63225355 A2 19880920 |
| 282 | IHC 72 | Acta Pharmaceutica Sinica, 27(6):407-11 (1992) |
| 283 | ipenoxazone |  |
| 284 | isradipine | U.S. Pat. No. 4,466,972 |
| 285 | JTV-519 | WO 09212148 |
| 286 | KB 2796 |  |
| 287 | KP-840 | Yakubutsu, Seishin, Kodo, 12(6):353 (1992) |
| 288 | KP 873 |  |
| 289 | KT-362 | Archiv Der Pharmazie, 328(4):313-6 (1995) |
| 290 | KT 2230 | General Pharmacology, 22(3):443-8 (1991) |
| 291 | KW 3049 (see benipidine) |  |
| 292 | L-366682 | EP 00444898 |
| 293 | L-651582 |  |
| 294 | L 735821 | WO 9514471 A1 19950601 British Journal of Pharmacology, 132(1):101-110 (2001) |
| 295 | lacidipine GR 43659 Sn305 | U.S. Pat. No. 4,801,599 DE 03529997 |
| 296 | LAS 30356 |  |
| 297 | LAS 30398 |  |
| 298 | LAS 30538 | Journal of Pharmacy and Pharmacology, 44(10:830-5 (1992) |
| 299 | LAS Z077 |  |
| 300 | LCB-2514 |  |
| 301 | lemildipine | P 59152373 A2 |
| 302 | lercanidipine | U.S. Pat. No. 4,705,797 |
| 303 | leualacin | EP 00358418 |
| 304 | levosemotiadil SA 3212 | WO 08700838 |
| 305 | lidoflazine R7904 | U.S. Pat. No. 3,267,104 |
| 306 | lifarizine RS 87476 | US 0435417 |
| 307 | LOE-908 |  |
| 308 | lomerizine KB 2796 | U.S. Pat. No. 4,663,325 EP 00158566 |
| 309 | LU 49700 (main metabolite of gallopamil) | DE 3642331 A1 |
| 310 | LU 49938 |  |
| 311 | LY-042826 | European Journal of Pharmacology, 408(3):241-248 (2000) |
| 312 | LY-393615 | European Journal of Pharmacology, 408(3):241-248 (2000) |
| 313 | manidipine/CV 4093/franidipine | U.S. Pat. No. 4,892,875 EP 00094159 |
| 314 | MCI 176 (MY7674) | EP 169537A2 |
| 315 | McN 5691 (see RWJ 26240) |  |
| 316 | McN-6186 |  |
| 317 | MCN 6497 |  |
| 318 | MD 260792 |  |
| 319 | MDL 143 |  |
| 320 | MDL 12330A |  |

TABLE 3-continued

| No. | Channel Blocker | Exemplary References |
|---|---|---|
| 321 | MDL 16582A | WO 9323082 |
| 322 | MDL 72567 | GB 2137622 A1 19841010 CAN 102:95548 |
| 323 | MEM 1003/nimopidine analog/BAY Z 4406 | |
| 324 | mepirodipine | |
| 325 | mesudipine | |
| 326 | mibefradil | EP 00268148 U.S. Pat. No. 4,808,605 |
| 327 | minodipine | |
| 328 | mioflazine | |
| 329 | MJ 14712 | |
| 330 | monatepil maleate (AD 2615) | WO 08601203 U.S. Pat. No. 4,749,703 |
| 331 | MPC 1304 | |
| 332 | MPC 2101 | FR 2514761 A1 |
| 333 | MR-14134 | Pharmacology, 51(2):84-95 (1995) |
| 334 | N-3601 | EP 254322 A1 |
| 335 | N 20776 | |
| 336 | N-allyl seceboldine | |
| 337 | naltiazem Ro 23-6152 | U.S. Pat. No. 4,652,561 |
| 338 | NB 818 | |
| 339 | NC 1100 | |
| 340 | NC O 700 | |
| 341 | NCC 09-0026 | |
| 342 | nexopamil | EP 00271013 |
| 343 | NH 2250 | |
| 344 | NH 2716 | |
| 345 | nicainoprol RU 42924 | DE 2934609 |
| 346 | nicardipine (nifelan) | U.S. Pat. No. 3,985,847 |
| 347 | nictiazem | |
| 348 | nifedipine | U.S. Pat. No. 3,485,847 |
| 349 | nigulipine | WO 8807525 A1 |
| 350 | niludipine | |
| 351 | nilvadipine FK 235 | U.S. Pat. No. 4,338,322 DE 02940833 |
| 352 | nimodipine | U.S. Pat. No. 3,842,096 |
| 353 | misoldipine Bay y 5552 | U.S. Pat. No. 4,154,839 |
| 354 | nitrendipine Bay k 5009 | U.S. Pat. No. 3,799,934 |
| 355 | NMDA/calcium channel antagonists, Allelix | WO 09745115 |
| 356 | NKY 722 | |
| 357 | NMED 126 (MC-34D) | WO 0145709 A1 U.S. Pat. No. 6,387,897 |
| 358 | NMED 427 | WO 0145709 A1 U.S. Pat. No. 6,387,897 |
| 359 | NMED 724 | WO 0145709 A1 U.S. Pat. No. 6,387,897 |
| 360 | NMED 826 | WO 0145709 A1 U.S. Pat. No. 6,387,897 |
| 361 | NMED JM-G-10 | WO 0145709 A1 U.S. Pat. No. 6,387,897 |
| 362 | NMED 157 39-1B4 | WO 0145709 A1 U.S. Pat. No. 6,387,897 |
| 363 | NMED 160 39-45-3 | WO 0145709 A1 U.S. Pat. No. 6,387,897 |
| 364 | NNC-09-0026 | WO 9201672 |
| 365 | NP 252 | Life Sciences, 48(2):183-8 (1991) |
| 366 | NS 626 | |
| 367 | NS-638 | U.S. Pat. No. 5,314,903 EP 545845 A1 |
| 368 | NS-649 | EP 520200 A2 |
| 369 | NS-696 | |
| 370 | NS-7 | WO 09607641 |
| 371 | NS 3034 | |
| 372 | NZ 105 | |
| 373 | olradipine S 11568 | FR 2602231 A1 |
| 374 | ONO-2921 | WO 0000470 A1 |
| 375 | OPC 13340 | |
| 376 | OPC 88117 | EP 236140 A2 |
| 377 | ORG 13020 | |
| 378 | Org-13061 | Fundamental & Clinical Pharmacology, 11(5):416-426 (1997) |
| 379 | OSAT (nifedipine) | |
| 380 | osthole | JP 47000430 |
| 381 | oxodipine IQB 837V | ES 531033 A1 |
| 382 | P 0825 | |
| 383 | P 1268 | |
| 384 | palonidipine hydrochloride | Ep 128010 A2 |
| 385 | PCA-50922 | |
| 386 | PCA-50938 | Brain Research 772(1,2):57-62 (1997) |
| 387 | PCA-50941 | |
| 388 | PCA 50982 | |
| 389 | PD-0204318 | WO 9943658 A1 |
| 390 | PD-029361 | IDdb 300520 |
| 391 | PD 122860 | Ep 206747 A2 |
| 392 | PD 151307 | U.S. Pat. No. 6,423,689 J. Med. Chem. 43:3472 (2000) |
| 393 | PD-157667 | U.S. Pat. No. 5,767,129 |
| 394 | PD-158143 | WO 9705125 A1 |
| 395 | PD 173212 | |
| 396 | PD 175069 | WO 9854123 A1 |
| 397 | PD 176078 | WO 9955688 J. Med. Chem. 43:3474 (2000) |
| 398 | PD 181283 | Bioorganic & Medicinal Chemistry Letters, 9(16):2453-2458 (1999) |
| 399 | pelanserin | |
| 400 | perhexiline | GB 1025578 |
| 401 | petrosynol | Tetrahedron, 49(45):10435-8 (1993) |
| 402 | PF 244 | |
| 403 | PFS 1144 (EO 122) | DE 2802208 |
| 404 | pirmenol | U.S. Pat. No. 4,112,103 |
| 405 | pirprofurol | |
| 406 | | |
| 407 | PN 200110 | |
| 408 | PNU 156654E | WO 9705102 A1 |
| 409 | pranidipine | EP 00145434 |
| 410 | prenylamine | |
| 411 | propiverine | DD 106643 |
| 412 | ptilomycalin AM | |
| 413 | QM 96233 | |
| 414 | QM 96159 | |
| 415 | QM 96127 | |
| 416 | QX 314 | Biophysical Journal, 27(1):39-55 (1979) |
| 417 | R 56865 | EP 184257 A1 |
| 418 | R 59494 | Ep 184257 A1 |
| 419 | R 71811 | |
| 420 | Rec 152288 | |
| 421 | Rec 152375, Rec 15/375 | |
| 422 | RGH-2716 (TDN 3451) | EP 414421 A2 |
| 423 | RGH 2970 | |
| 424 | riodipine | |
| 425 | Ro-11-2933 | EP 00523493 |
| 426 | Ro 18-3981 | |
| 427 | Ro 40-5967 | |
| 428 | RO 445912 dithiane derivatives of tiapamil | Biochemical Pharmacology, 50(2):187-96 (1995) |
| 429 | ronipamil | |
| 430 | RS-5773 | EP 00353032 |
| 431 | RS 93007 | |
| 432 | RS 93522 | U.S. Pat. No. 4,595,690 |
| 433 | RU-43945 | WO 9323082 A1 |
| 434 | RWJ-22108 | US 04845225 |
| 435 | RWJ-22726 | US 04845225 |
| 436 | RWJ 26240 McN 5691 | EP 146721 A2 |
| 437 | RWJ 26899 | EP 237191 A1 |
| 438 | RJW-26902 | |
| 439 | RWJ-29009 | EP 00493048 |
| 440 | RWJ-37868 | WO 0048584 |
| 441 | ryanodine | |
| 442 | S-(−)-amlodipine | |
| 443 | S 11568 | |
| 444 | S 12967 | ZA 9000231 A |
| 445 | S-12968 | EP 00406502 |

TABLE 3-continued

| No. | Channel Blocker | Exemplary References |
|---|---|---|
| 446 | S-2150 | Ep 00615971 |
| 447 | S-312-d | JP 03052890 |
| 448 | S 830327 | |
| 449 | SA 2572 | JP 63104969 A2 |
| 450 | SA 2995 | |
| 451 | SA 3212 | |
| 452 | sabeluzole | Ep 184257 A1 |
| 453 | safinamide | EP 400495 A1 |
| 454 | sagandipine | |
| 455 | salicylaldoxime | Clinical and Experimental Pharmacology and Physiology 26(12):964-9 (1999) |
| 456 | SANK-71996 | |
| 457 | SB-201823A | WO 09202502 |
| 458 | SB-206284A | |
| 459 | SB 221420A | WO 9002494 A1 |
| 460 | SB-237376 | WO 0209761 A2 |
| 461 | SB 262470 | WO 0183546 A1 |
| 462 | SC 30552 | |
| 463 | SDZ-249482 | |
| 464 | selodipine | |
| 465 | semotiadil (SD 3211) | U.S. Pat. No. 4,786,635 JP 09012576 |
| 466 | SIM 6080 | Ep 293925 A2 |
| 467 | sipatrigine | EP 372934 A2 |
| 468 | sinomenine (active from a Chinese medicinal plant) | WO 0269971 A1 |
| 469 | siratiazem | WO 09117153 |
| 470 | SKF-45675 | |
| 471 | SKF-96365 | European Journal of Pharmacology 188(6):417-21 (1990) |
| 472 | SKT-M-26 | |
| 473 | SL-34.0829 | WO 0209761 A2 |
| 474 | SL 651708 | |
| 475 | SL 851016 | |
| 476 | SL-870495 | |
| 477 | SM-6586 | EP 00177965 |
| 478 | SNX-124 | |
| 479 | SNX 185 | WO 9310145 A1 |
| 480 | SNX-236 | WO 09313128 |
| 481 | SNX-239 | Pain, 60(1):83-90 (1995) |
| 482 | SNX-483 (peptides from tarantula venom) | WO 9805780 A2 |
| 483 | sornidipine | |
| 484 | SQ 31486 | EP 205334 A2 |
| 485 | SQ 31727 | |
| 486 | SQ 31765 | |
| 487 | SQ 32321 | |
| 488 | SQ 32324 | |
| 489 | SQ 32547 | EP 400665 A2 |
| 490 | SQ 32926 | EP 400665 A2 |
| 491 | SQ-33351 | WO 09006118 |
| 492 | SQ 33537 | |
| 493 | SQ 34399 | |
| 494 | SR-33805 | EP 576347 A1 |
| 495 | SUN 5647 | |
| 496 | SUN 6087 | |
| 497 | SUN-N8075 | WO 9923072 A2 |
| 498 | T-477 | EP 00441539 |
| 499 | TA-993 | JP 01050872 |
| 500 | taludipine | |
| 501 | tamolarizine | EP 00354068 |
| 502 | TDN-345 | |
| 503 | Teczem | |
| 504 | temiverine | CAN 131:193592 |
| 505 | terflavoxate | EP 72620 A1 |
| 506 | terodiline TD 758 | U.S. Pat. No. 3,371,014 |
| 507 | tetrandrine | Clinical and Experimental Pharmacology and Physiology, 23(8):715-753 (1996) |
| 508 | TH-1177 | |
| 509 | TH-9229 | |
| 510 | thapsigargin | WO 09607415 British Journal of Pharmacology, 95(3):705-712 (1985) |
| 511 | tiapamil | |
| 512 | tinctormine | Chemical & Pharmaceutical Bulletin 40(12):3355-7 (1992) |
| 513 | TJN 220 (O-ethylfangchinoline) | JP 63179878 A2 |
| 514 | TMB 8 | Journal of Cell Science 79:151-160 (1985) |
| 515 | TN-871 | European Journal of Pharmacology 342 (2/3):167-175 (1998) |
| 516 | TR 2957 | |
| 517 | trapidil | |
| 518 | trimetazidine | U.S. Pat. No. 3,262,852 |
| 519 | TY 10835 | Pharmacometrics, 1998, 54:3 (153) |
| 520 | U-88999 | WO 9204338 |
| 521 | U-92032 | WO 09204338 |
| 522 | U-92798 | WO 9204338 A1 |
| 523 | UK 1745 | EP 653426 A1 |
| 524 | UK-51656 | EP 00089167 |
| 525 | UK 52831 | JP 59118782 A2 |
| 526 | UK 55444 | EP 00132375 |
| 527 | UK 56593 | |
| 528 | UK-84149 | EP 404359 A1 |
| 529 | ULAH 99 | European Journal of Pharmacology, 229(1):55-62 (1992) |
| 530 | vantanipidine | EP 257616 A2 |
| 531 | verapamil, verelan | U.S. Pat. No. 3,261,859 |
| 532 | S-verapamil, D-2024, levoverapamil | WO 09509150 |
| 533 | vexibinol Sophoraflavanone G | Chemical and Pharmaceutical Bulletin 38(4):1039-44 (1990) |
| 534 | vinigrol | |
| 535 | vintoperol RGH 2981 RT 303 | WO 9207851 |
| 536 | vingrol | |
| 537 | vintoperol/RGH 2981/RT 303 | WO 9207851 |
| 538 | VUF-8929 | EP 467435 A2 |
| 539 | VULM 993 | |
| 540 | vantanipidine | Ep 257616 A2 |
| 541 | W 787 | |
| 542 | WAS 4206 | |
| 543 | WK 269 | |
| 544 | WY 27569 | |
| 545 | WY 44644 | |
| 546 | WY 44705 | |
| 547 | WY 46622 | |
| 548 | WY 47324 | |
| 549 | xanthonolol | U.S. Pat. No. 5,495,005 |
| 550 | Y 19638 | |
| 551 | Y-22516 | WO 9323082 |
| 552 | Y 208835 | |
| 553 | YC 114 | |
| 554 | YH-334 | EP 00366548 |
| 555 | YM 15430-1 (see YM 430) | |
| 556 | YM-16151-4 (YM 151) | EP 00167371 |
| 557 | YM-430 (YM 15430) | WO 0209761 A2 |
| 558 | YS 035 | BE 897244 |
| 559 | YS 161 | |
| 560 | Z-6568 | Journal of Mass Spectrometry, 31(1):37-46 (1996) |
| 561 | ziconotiide omega conotoxin/MVIIA/SNX-111 | WO 9107980 |
| 562 | ZM-224832 | EP 00343865 |
| 563 | zonisamide | U.S. Pat. No. 4,172,896 |

Synthesis

The synthesis of charge-modified ion channel blockers may involve the selective protection and deprotection of alcohols, amines, ketones, sulfhydryls or carboxyl functional groups of the parent ion channel blocker, the linker, the bulky group, and/or the charged group. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxyls include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a Lewis acid, or hydrogenation) are required to remove each, exclusive of other protecting groups in a molecule. The conditions required for the addition of protecting groups to amine, alcohol, sulfhydryl, and carboxyl functionalities and the conditions required for their removal are provided in detail in T. W. Green and P. G. M. Wuts, *Protective Groups in Organic Synthesis* (2$^{nd}$ Ed.), John Wiley & Sons, 1991 and P. J. Kocienski, *Protecting Groups*, Georg Thieme Verlag, 1994.

Charge-modified ion channel blockers can be prepared using techniques familiar to those skilled in the art. The modifications can be made, for example, by alkylation of the parent ion channel blocker using the techniques described by J. March, *Advanced Organic Chemistry: Reactions, Mechanisms and Structure*, John Wiley & Sons, Inc., 1992, page 617. The conversion of amino groups to guanidine groups can be accomplished using standard synthetic protocols. For example, Mosher has described a general method for preparing mono-substituted guanidines by reaction of aminoiminomethanesulfonic acid with amines (Kim et al., *Tetrahedron Lett.* 29:3183 (1988)). A more convenient method for guanylation of primary and secondary amines was developed by Bernatowicz employing 1H-pyrazole-1-carboxamidine hydrochloride; 1-H-pyrazole-1-(N,N'-bis(tert-butoxycarbonyl)carboxamidine; or 1-II-pyrazole-1-(N,N'-bis (benzyloxycarbonyl)carboxamidine. These reagents react with amines to give mono-substituted guanidines (see Bernatowicz et al., *J. Org. Chem.* 57:2497 (1992); and Bernatowicz et al., *Tetrahedron Lett.* 34:3389 (1993)). In addition, thioureas and S-alkyl-isothioureas have been shown to be useful intermediates in the syntheses of substituted guanidines (Poss et al., *Tetrahedron Lett.* 33:5933 (1992)). In certain embodiments, the guanidine is part of a heterocyclic ring having two nitrogen atoms (see, for example, the structures below).
The ring system can include an alkylene or

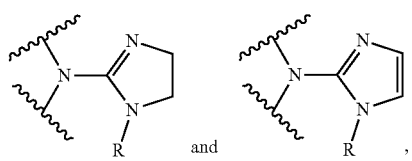

alkenylene of from 2 to 4 carbon atoms, e.g., ring systems of 5, 6, and 7-membered rings. Such ring systems can be prepared, for example, using the methods disclosed by Schlama et al., *J. Org. Chem.* 62:4200 (1997).

Charge-modified ion channel blockers can be prepared by alkylation of an amine nitrogen in the parent compound as shown in Scheme 1.

Scheme 1

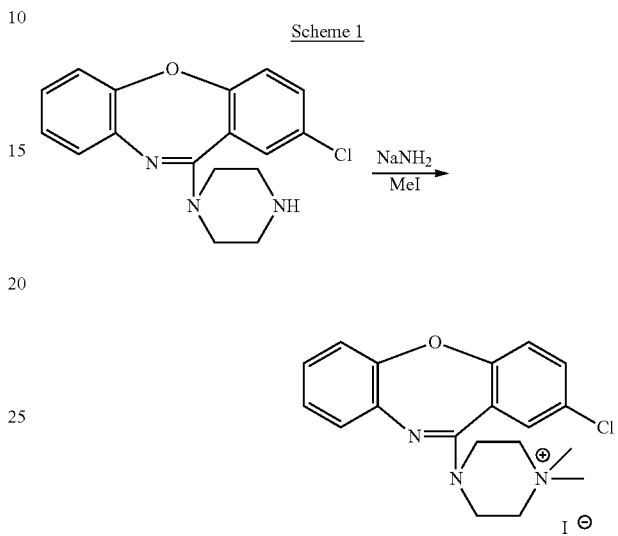

Alternatively, charge-modified ion channel blockers can be prepared by introduction of a guanidine group. The parent compound can be reacted with a cynamide, e.g., methylcyanamide, as shown in Scheme 2 or pyrazole-1-carboxamidine derivatives as shown in Scheme 3 where Z is H or a suitable protecting group. Alternatively, the parent compound can be reacted with cyanogens bromide followed by reaction with methylchloroaluminum amide as shown in Scheme 4. Reagents such as 2-(methylthio)-2-imidazoline can also be used to prepare suitably functionalized derivatives (Scheme 5).

Scheme 2

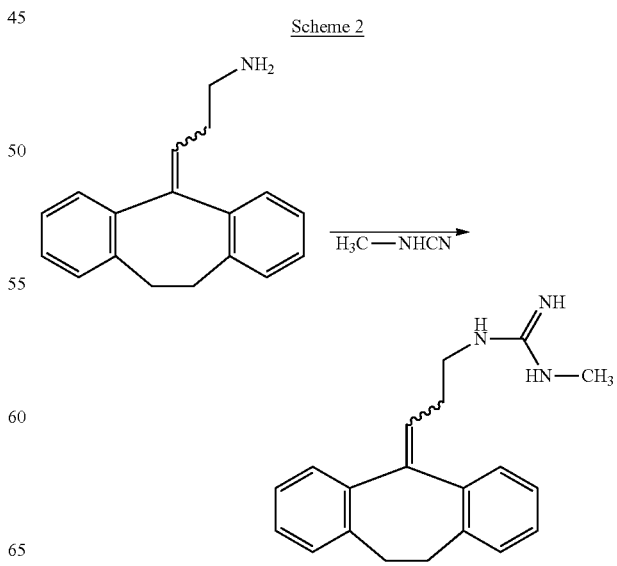

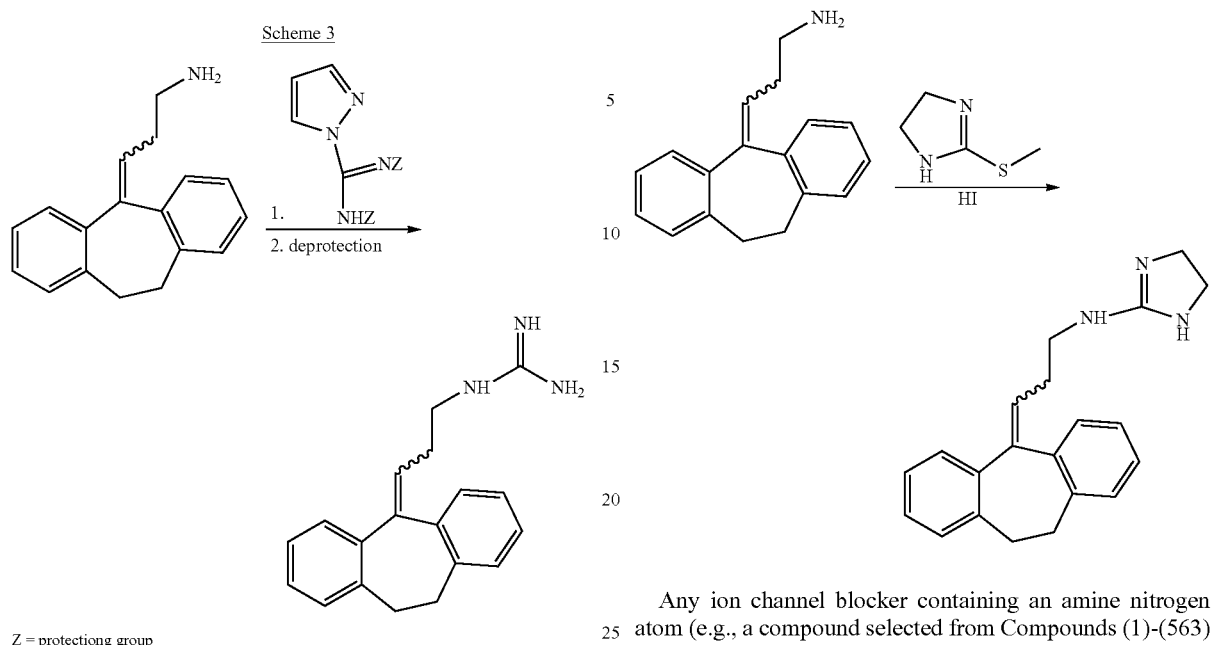

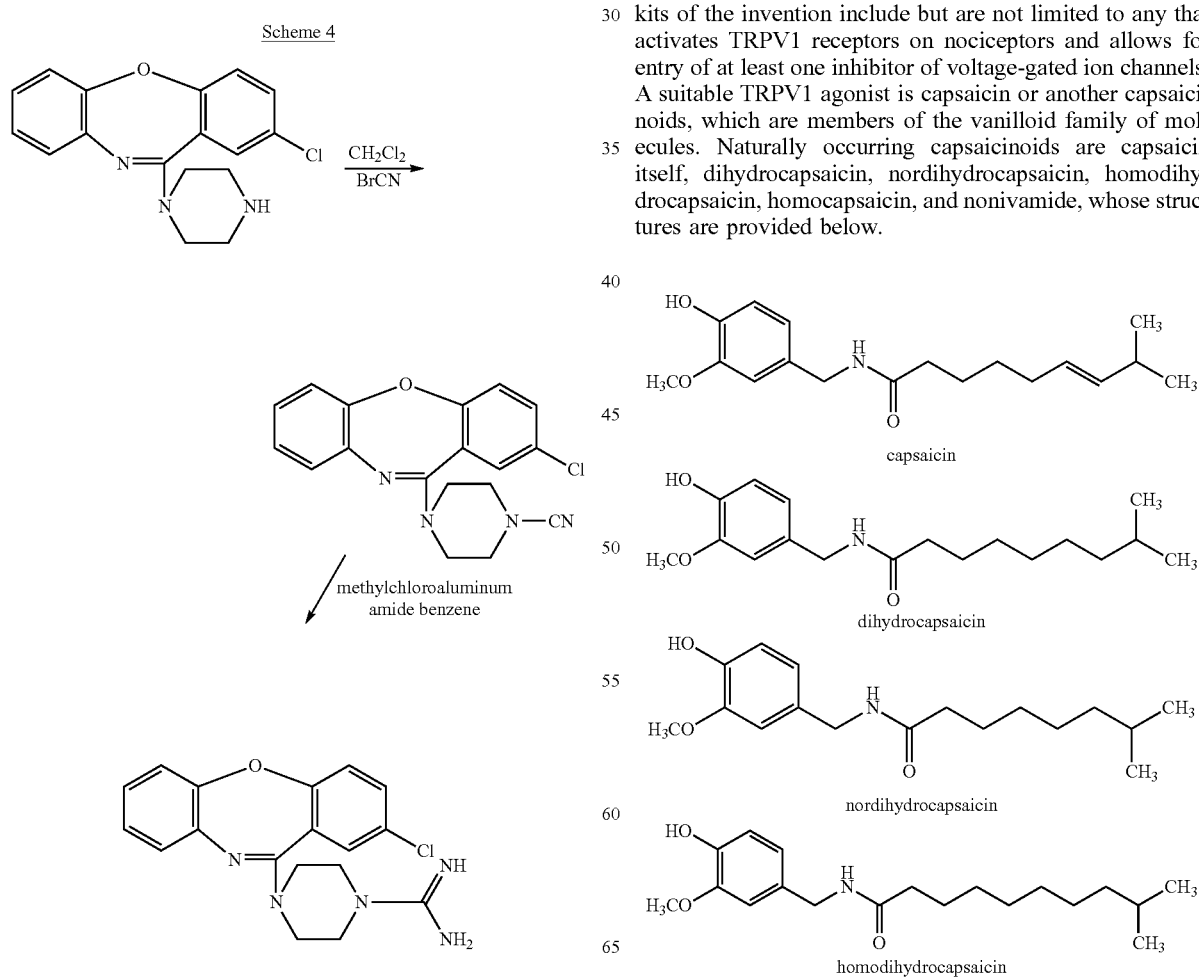

Any ion channel blocker containing an amine nitrogen atom (e.g., a compound selected from Compounds (1)-(563) or a compound according to Formulas (I)-(XIV)) can be modified as shown in Schemes 1-5.

TRPV1 Agonists

TRPV1 agonists that can be employed in the methods and kits of the invention include but are not limited to any that activates TRPV1 receptors on nociceptors and allows for entry of at least one inhibitor of voltage-gated ion channels. A suitable TRPV1 agonist is capsaicin or another capsaicinoids, which are members of the vanilloid family of molecules. Naturally occurring capsaicinoids are capsaicin itself, dihydrocapsaicin, nordihydrocapsaicin, homodihydrocapsaicin, homocapsaicin, and nonivamide, whose structures are provided below.

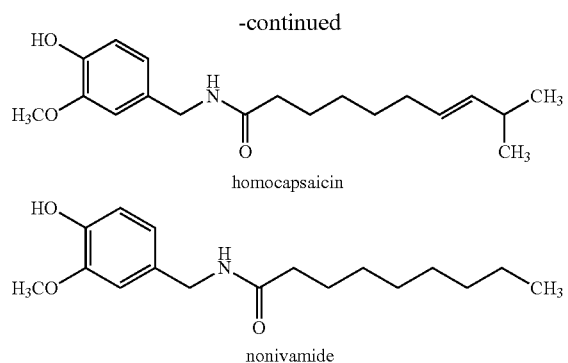

homocapsaicin nonivamide

Other suitable capsaicinoids and capsaicinoid analogs and derivatives for use in the compositions and methods of the present invention include naturally occurring and synthetic capsaicin derivatives and analogs including, e.g., vanilloids (e.g., N-vanillyl-alkanedienamides, N-vanillyl-alkanedienyls, and N-vanillyl-cis-monounsaturated alkenamides), capsiate, dihydrocapsiate, nordihydrocapsiate and other capsinoids, capsiconiate, dihydrocapsiconiate and other coniferyl esters, capsiconinoid, resiniferatoxin, tinyatoxin, civamide, N-phenylmethylalkenamide capsaicin derivatives, olvanil, N-[(4-(2-aminoethoxy)-3-methoxyphenyl)methyl]-9Z-octa-decanamide, N-oleyl-homovanillamide, triprenyl phenols (e.g., scutigeral), gingerols, piperines, shogaols, guaiacol, eugenol, zingerone, nuvanil, NE-19550, NE-21610, and NE-28345. Additional capsaicinoids, their structures, and methods of their manufacture are described in U.S. Pat. Nos. 7,446,226 and 7,429,673, which are hereby incorporated by reference.

Additional suitable TRPV1 agonists include but are not limited to eugenol, arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldopamine (NADA), 6'-iodoresiniferatoxin (6'-IRTX), C18 N-acylethanolamines, lipoxygenase derivatives such as 12-hydroperoxyeicosatetraenoic acid, inhibitor cysteine knot (ICK) peptides (vanillotoxins), piperine, MSK195 (N-[2-(3,4-dimethylbenzyl)-3-(pivaloyloxy)propyl]-2-[4-(2-aminoethoxy)-3-methoxyphenyl]acetamide), JYL79 (N-[2-(3,4-dimethylbenzyl)-3-(pivaloyloxy)propyl]-N'-(4-hydroxy-3-methoxybenzyl)thiourea), hydroxy-alpha-sanshool, 2-aminoethoxydiphenyl borate, 10-shogaol, oleylgingerol, oleylshogaol, and SU200 (N-(4-tert-butylbenzyl)-N'-(4-hydroxy-3-methoxybenzyl)thiourea).

Still other TRPV1 agonists include amylocaine, articaine, benzocaine, bupivacaine, carbocaine, carticaine, chloroprocaine, cyclomethycaine, dibucaine (cinchocaine), dimethocaine (larocaine), etidocaine, hexylcaine, levobupivacaine, lidocaine, mepivacaine, meprylcaine (oracaine), metabutoxycaine, piperocaine, prilocaine, procaine (novacaine), proparacaine, propoxycaine, risocaine, ropivacaine, tetracaine (amethocaine), and trimecaine.

TRP1A Agonists

TRP1A agonists that can be employed in the methods and kits of the invention include any that activates TRP1A receptors on nociceptors or pruriceptors and allows for entry of at least one inhibitor of voltage-gated ion channels. Suitable TRP1A agonists include but are not limited to cinnamaldehyde, allyl-isothiocynanate, diallyl disulfide, icilin, cinnamon oil, wintergreen oil, clove oil, acrolein, hydroxy-alpha-sanshool, 2-aminoethoxydiphenyl borate, 4-hydroxynonenal, methyl p-hydroxybenzoate, mustard oil, and 3'-carbamoylbiphenyl-3-yl cyclohexylcarbamate (URB597). Still other agonists include amylocaine, articaine, benzocaine, bupivacaine, carbocaine, carticaine, chloroprocaine, cyclomethycaine, dibucaine (cinchocaine), dimethocaine (larocaine), etidocaine, hexylcaine, levobupivacaine, lidocaine, mepivacaine, meprylcaine (oracaine), metabutoxycaine, piperocaine, prilocaine, procaine (novacaine), proparacaine, propoxycaine, risocaine, ropivacaine, tetracaine (amethocaine), and trimecaine.

P2X Agonists

P2X agonists that can be employed in the methods and kits of the invention include any that activates P2X receptors on nociceptors or pruriceptors and allows for entry of at least one inhibitor of voltage-gated ion channels. Suitable P2X agonists include but are not limited to 2-methylthio-ATP, 2' and 3'-O-(4-benzoylbenzoyl)-ATP, and ATP5'-O-(3-thiotriphosphate).

TRPM8 Agonists

TRPM8 agonists that can be employed in the methods and kits of the invention include any that activates TRPM8 receptors on nociceptors or pruriceptors and allows for entry of at least one inhibitor of voltage-gated ion channels. Suitable TRPM8 agonists include but are not limited to menthol, iciclin, eucalyptol, linalool, geraniol, and hydroxycitronellal.

Additional Agents

If desired, one or more additional biologically active agents typically used to treat neurogenic inflammation may be used in combination with a composition of the invention described herein. The biologically active agents include, but are not limited to, acetaminophen, NSAIDs, glucocorticoids, narcotics (e.g. opioids), tricyclic antidepressants, amine transporter inhibitors, anticonvulsants, antiproliferative agents, and immune modulators. The biologically active agents can be administered prior to, concurrent with, or following administration of a composition of the invention, using any formulation, dosing, or administration known in the art that is therapeutically effective.

Non-steroidal anti-inflammatory drugs (NSAIDs) that can be administered to a patient (e.g., a human) suffering from neurogenic inflammation in combination with a composition of the invention include, but are not limited to, acetylsalicylic acid, amoxiprin, benorylate, benorilate, choline magnesium salicylate, diflunisal, ethenzamide, faislamine, methyl salicylate, magnesium salicylate, salicyl salicylate, salicylamide, diclofenac, aceclofenac, acemethacin, alclofenac, bromfenac, etodolac, indometacin, nabumetone, oxametacin, proglumetacin, sulindac, tolmetin, ibuprofen, alminoprofen, benoxaprofen, carprofen, dexibuprofen, dexketoprofen, fenbufen, fenoprofen, flunoxaprofen, flurbiprofen, ibuproxam, indoprofen, ketoprofen, ketorolac, loxoprofen, naproxen, oxaprozin, pirprofen, suprofen, tiaprofenic acid, mefenamic acid, flufenamic acid, meclofenamic acid, tolfenamic acid, phenylbutazone, ampyrone, azapropazone, clofezone, kebuzone, metamizole, mofebutazone, oxyphenbutazone, phenazone, sulfinpyrazone, piroxicam, droxicam, lornoxicam, meloxicam, tenoxicam, and the COX-2 inhibitors celecoxib, etoricoxib, lumiracoxib, parecoxib, rofecoxib, valdecoxib, and pharmaceutically acceptable salts thereof.

Glucocorticoids that can be administered to a patient (e.g., a human) suffering from neurogenic inflammation in combination with a composition of the invention include, but are not limited to, hydrocortisone, cortisone acetate, prednisone, prednisolone, methylprednisolone, dexamethasone, betamethasone, triamcinolone, beclometasone, fludrocortisones acetate, deoxycorticosterone acetate, aldosterone, and pharmaceutically acceptable salts thereof.

Narcotics that can be administered to a patient (e.g., a human) suffering from neurogenic inflammation in combination with a composition of the invention include, but are not limited, to tramadol, hydrocodone, oxycodone, morphine, and pharmaceutically acceptable salts thereof.

Antiproliferative and immune modulatory agents that can be administered to a patient (e.g., a human) suffering from neurogenic inflammation in combination with a composition of the invention include, but are not limited to, alkylating agents, platinum agents, antimetabolites, topoisomerase inhibitors, dihydrofolate reductase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF-alpha agonists, TNF-alpha antagonists or scavengers, interleukin 1 (IL-1) antagonists or scavengers, endothelin A receptor antagonists, retinoic acid receptor agonists, hormonal agents, antihormonal agents, photodynamic agents, and tyrosine kinase inhibitors.

Formulation of Compositions

The administration of a combination of the invention may be by any suitable means that results in the reduction of inflammation at the target region (e.g., any inflamed tissue or mucosal surface). The inhibitor(s) of voltage-gated ion channels may be contained in any appropriate amount in any suitable carrier substance, and are generally present in amounts totaling 1-95% by weight of the total weight of the composition. The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, gastrointesitnal, reproductive or oral mucosa.

Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Each compound of a combination therapy, as described herein, may be formulated in a variety of ways that are known in the art. For example, the first and second agents of the combination therapy may be formulated together or separately. Desirably, the first and second agents are formulated together for the simultaneous or near simultaneous administration of the agents.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions.

The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Controlled Release Formulations

Each compound of the invention, alone or in combination with one or more of the biologically active agents as described herein, can be formulated for controlled release (e.g., sustained or measured) administration, as described in U.S. Patent Application Publication Nos. 2003/0152637 and 2005/0025765, each incorporated herein by reference. For example, a compound of the invention, alone or in combination with one or more of the biologically active agents as described herein, can be incorporated into a capsule or tablet, that is administered to the site of inflammation.

Any pharmaceutically acceptable vehicle or formulation suitable for local infiltration or injection into a site to be treated (e.g., a painful surgical incision, wound, or joint), that is able to provide a sustained release of compound of the invention, alone or in combination with one or more of the biologically active agents as described herein, may be employed to provide for prolonged elimination or alleviation of inflammation, as needed. Slow release formulations known in the art include specially coated pellets, polymer formulations or matrices for surgical insertion or as sustained release microparticles, e.g., microspheres or microcapsules, for implantation, insertion, infusion or injection, wherein the slow release of the active medicament is brought about through sustained or controlled diffusion out of the matrix and/or selective breakdown of the coating of the preparation or selective breakdown of a polymer matrix. Other formulations or vehicles for sustained or immediate delivery of an agent to a preferred localized site in a patient include, e.g., suspensions, emulsions, gels, liposomes and any other suitable art known delivery vehicle or formulation acceptable for subcutaneous or intramuscular administration.

A wide variety of biocompatible materials may be utilized as a controlled release carrier to provide the controlled release of a compound of the invention, alone or in combination with one or more biologically active agents, as described herein. Any pharmaceutically acceptable biocompatible polymer known to those skilled in the art may be utilized. It is preferred that the biocompatible controlled release material degrade in vivo within about one year, preferably within about 3 months, more preferably within about two months. More preferably, the controlled release material will degrade significantly within one to three months, with at least 50% of the material degrading into non-toxic residues, which are removed by the body, and 100% of the compound of the invention being released within a time period within about two weeks, preferably within about 2 days to about 7 days. A degradable controlled release material should preferably degrade by hydrolysis, either by surface erosion or bulk erosion, so that release is not only sustained but also provides desirable release rates. However, the pharmacokinetic release profile of these formulations may be first order, zero order, bi- or multi-phasic, to provide the desired reversible local anesthetic effect over the desired time period.

Suitable biocompatible polymers can be utilized as the controlled release material. The polymeric material may comprise biocompatible, biodegradable polymers, and in certain preferred embodiments is preferably a copolymer of lactic and glycolic acid. Preferred controlled release materials which are useful in the formulations of the invention include the polyanhydrides, polyesters, co-polymers of lactic acid and glycolic acid (preferably wherein the weight ratio of lactic acid to glycolic acid is no more than 4:1 i.e., 80% or less lactic acid to 20% or more glycolic acid by weight)) and polyorthoesters containing a catalyst or degradation enhancing compound, for example, containing at least 1% by weight anhydride catalyst such as maleic anhydride. Examples of polyesters include polylactic acid, polyglycolic acid and polylactic acid-polyglycolic acid copolymers. Other useful polymers include protein polymers such as collagen, gelatin, fibrin and fibrinogen and polysaccharides such as hyaluronic acid.

The polymeric material may be prepared by any method known to those skilled in the art. For example, where the polymeric material is comprised of a copolymer of lactic and glycolic acid, this copolymer may be prepared by the procedure set forth in U.S. Pat. No. 4,293,539, incorporated herein by reference. Alternatively, copolymers of lactic and glycolic acid may be prepared by any other procedure known to those skilled in the art. Other useful polymers include polylactides, polyglycolides, polyanhydrides, polyorthoesters, polycaprolactones, polyphosphazenes, polyphosphoesters, polysaccharides, proteinaceous polymers, soluble derivatives of polysaccharides, soluble derivatives of proteinaceous polymers, polypeptides, polyesters, and polyorthoesters or mixtures or blends of any of these. Pharmaceutically acceptable polyanhydrides which are useful in the present invention have a water-labile anhydride linkage. The rate of drug release can be controlled by the particular polyanhydride polymer utilized and its molecular weight. The polysaccharides may be poly-1,4-glucans, e.g., starch glycogen, amylose, amylopectin, and mixtures thereof. The biodegradable hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch (HES), hydroxyethyl amylose, dialdehyde starch, and the like. The polyanhydride polymer may be branched or linear. Examples of polymers which are useful in the present invention include (in addition to homopolymers and copolymers of poly(lactic acid) and/or poly(glycolic acid)) poly[bis(p-carboxyphenoxy) propane anhydride](PCPP), poly[bis(p-carboxy)methane anhydride] (PCPM), polyanhydrides of oligomerized unsaturated aliphatic acids, polyanhydride polymers prepared from amino acids which are modified to include an additional carboxylic acid, aromatic polyanhydride compositions, and co-polymers of polyanhydrides with other substances, such as fatty acid terminated polyanhydrides, e.g., polyanhydrides polymerized from monomers of dimers and/or trimers of unsaturated fatty acids or unsaturated aliphatic acids. Polyanhydrides may be prepared in accordance with the methods set forth in U.S. Pat. No. 4,757,128, incorporated herein by reference. Polyorthoester polymers may be prepared, e.g., as set forth in U.S. Pat. No. 4,070,347, incorporated herein by reference. Polyphosphoesters may be prepared and used as set forth in U.S. Pat. Nos. 6,008,318, 6,153,212, 5,952,451, 6,051,576, 6,103,255, 5,176,907 and 5,194,581, each of which is incorporated herein by reference.

Proteinaceous polymers may also be used. Proteinaceous polymers and their soluble derivatives include gelation biodegradable synthetic polypeptides, elastin, alkylated collagen, alkylated elastin, and the like. Biodegradable synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alanine, L-lysine, L-phenylalanine, L-valine, L-tyrosine, and the like.

In additional embodiments, the controlled release material, which in effect acts as a carrier for a compound of the invention, alone or in combination with one or more biologically active agents as described herein, can further include a bioadhesive polymer such as pectins (polygalacturonic acid), mucopolysaccharides (hyaluronic acid, mucin) or non-toxic lectins or the polymer itself may be bioadhesive, e.g., polyanhydride or polysaccharides such as chitosan.

In embodiments where the biodegradable polymer comprises a gel, one such useful polymer is a thermally gelling polymer, e.g., polyethylene oxide, polypropylene oxide (PEO-PPO) block copolymer such as Pluronic™ F127 from BASF Wyandotte. In such cases, the local anesthetic formulation may be injected via syringe as a free-flowing liquid, which gels rapidly above 30° C. (e.g., when injected into a patient). The gel system then releases a steady dose of a compound of the invention, alone or in combination with one or more biologically active agents as described herein, at the site of administration.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in a combination therapy, as described herein, can, independently, be one to four times daily for one day to one year, and may even be for the life of the patient. Chronic, long-term administration will be indicated in many cases.

Topical Formulations

A composition of the invention, alone or in combination with one or more of the biologically active agents described herein, can also be adapted for topical use with a topical vehicle containing from between 0.0001% and 25% (w/w) or more of active ingredient(s).

In a preferred combination, the active ingredients are preferably each from between 0.0001% to 10% (w/w), more preferably from between 0.0005% to 4% (w/w) active agent. The cream can be applied one to four times daily, or as needed.

Performing the methods described herein, the topical vehicle containing the composition of the invention, or a combination therapy containing a composition of the invention is preferably applied to the site of inflammation on the patient. For example, a cream may be applied to the hands of a patient suffering from arthritic fingers.

Formulations for Nasal and Inhalation Administration

The pharmaceutical compositions of the invention can be formulated for nasal or intranasal administration. Formulations suitable for nasal administration, when the carrier is a solid, include a coarse powder having a particle size, for example, in the range of approximately 20 to 500 microns which is administered by rapid inhalation through the nasal passage. When the carrier is a liquid, for example, a nasal spray or as nasal drops, one or more of the formulations can be admixed in an aqueous or oily solution, and inhaled or sprayed into the nasal passage.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount, Capsules and cartridges of, for example, gelatin for use in an inhaler or insufflator can be formulated containing a powder mix of the compound and a suitable powder base such as lactose or starch.

EXAMPLES

The following example is intended to illustrate the invention, and is not intended to limit it.

Example 1: Treatment of Neurogenic Inflammation with Intravenous Injection of QX-314

FIG. 1 is a graph showing the effect of intravenous QX-314 (0.4 mg/kg) on the edema elicited by injection of complete Freund's adjuvant (CFA) in the rat hindpaw determined by measuring the total volume of the hindpaw by plethysmography. The degree of swelling produced by injection of CFA is reduced by administration of QX-314 reflecting reduction in neurogenic edema resulting from the blockade of nociceptors by QX314. QX-314 by itself has no effect different from administration of saline.

Example 2: Entry of N-Methyl-Verapamil into Dorsal Root Ganglion Neurons Through Capsaicin-Activated TRPV1 Channels N-methyl-verapamil, a charged derivative of the known calcium channel blocker verapamil and structurally related to D-890, can be loaded into dorsal root ganglion neurons through activation of TRPV1 channels by capsaicin. The internally-loaded N-methyl-verapamil then produces long-lasting inhibition of the voltage-dependent calcium channels in the neurons. Entry of the drug into the cell, and its blocking action, depends on applying the drug in the presence of capsaicin to activate the TRPV1 channels present in the neuronal membrane.

Figure 2:
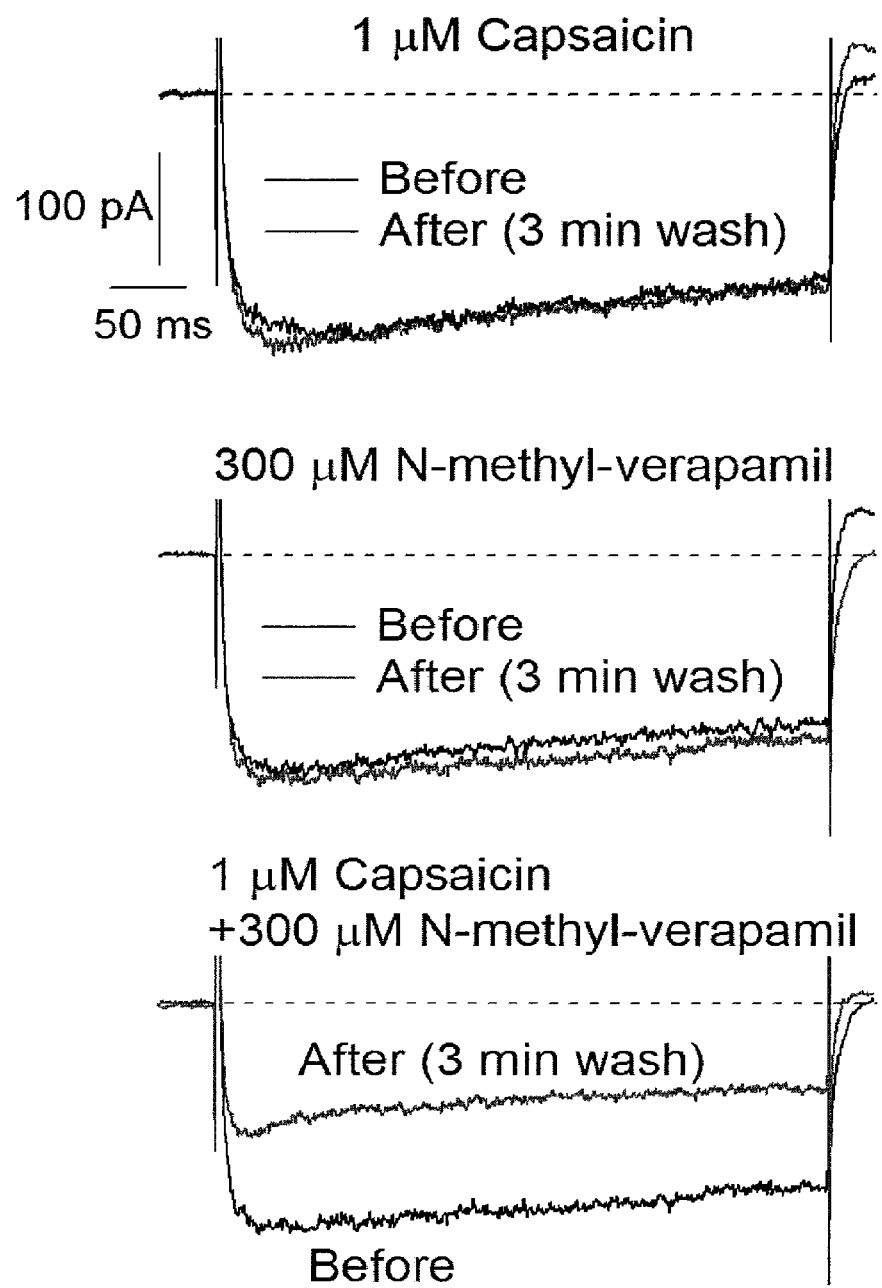
FIG. 2 shows the inhibition of voltage-dependent calcium channel current in a dorsal root ganglion (DRG) neuron by N-methyl-verapamil applied in the presence of capsaicin to open TRPV1 channels. Entry of the drug into the cell, and its blocking action, depends on applying the drug in the presence of capsaicin to activate the TRPV1 channels present in the neuronal membrane.

As shown in FIG. 2, the inhibition of voltage-dependent calcium channel current in a DRG neuron by N-methyl-verapamil applied in the presence of capsaicin to open TRPV1 channels. The traces show currents through voltage-activated calcium channels in a dissociated rat dorsal root ganglion neuron, recorded in whole-cell mode. Current was carried by 2 mM $Ba^{2+}$ on a background of 155 mM N-methyl-D-glucamine (to eliminate Na current), with an internal CsCl-based solution. Calcium channels were opened by a voltage step from −80 mV to −20 mV. When channels are opened, inward-going current is carried by $Ba^{2+}$ ions flowing into the cell.

Each panel shows calcium channel currents before and 3 minutes after exposure of the cell to either 1 μM capsaicin alone (top panel), 300 μM N-methyl-verapamil alone (middle panel), or 300 μM N-methyl-verapamil applied in the presence of 1 μM capsaicin to open TRPV1 channels (bottom panel). Control experiments using either capsaicin alone or N-methyl-verapamil alone each produce weak, transient effects that are rapidly reversed when the agents are washed away. The combination, however, produces an inhibition of calcium channel currents that persists after washout of the agents, consistent with N-methyl-verapamil having entered through TRPV1 channels and remaining trapped inside the cells, blocking the calcium channels from the inside.

OTHER EMBODIMENTS

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if each independent publication was specifically and individually incorporated by reference.

What is claimed is:

1. A compound represented by Formula (XII), $$\text{(XII)}$$

wherein
each of $R^{12A}$, $R^{12B}$, $R^{12C}$, and $R^{12D}$ is, independently, substituted or unsubstituted $C_{1-4}$ alkyl, substituted or unsubstituted $C_{2-4}$ alkenyl, substituted or unsubstituted $C_{2-4}$ alkynyl, substituted or unsubstituted $C_{2-4}$ heteroalkyl, $C_{7-14}$ alkaryl, $C_{3-10}$ alkcycloalkyl, or $C_{3-10}$ alkheterocyclyl; or $R^{12A}$ and $R^{12B}$ together complete a heterocyclic ring having at least one nitrogen atom;
n is an integer from 1 to 5;
each of $R^{12E}$ and $R^{12F}$ is, independently, H, substituted or unsubstituted $C_{1-4}$ alkyl, substituted or unsubstituted $C_{2-4}$ alkenyl, substituted or unsubstituted $C_{2-4}$ alkynyl, substituted or unsubstituted $C_{2-4}$ heteroalkyl, $C_{7-14}$ alkaryl, $C_{3-10}$ alkcycloalkyl, or $C_{3-10}$ alkheterocyclyl; and
X is any pharmaceutically acceptable anion.

2. The compound of claim 1, wherein each of $R^{12A}$, $R^{12B}$, and $R^{12C}$ is, independently, substituted or unsubstituted $C_{1-4}$ alkyl, substituted or unsubstituted $C_{2-4}$ alkenyl, substituted or unsubstituted $C_{2-4}$ alkynyl, or substituted or unsubstituted $C_{2-4}$ heteroalkyl.

3. The compound of claim 2, wherein each of $R^{12A}$, $R^{12B}$, and $R^{12C}$ is, independently, substituted or unsubstituted $C_{1-4}$ alkyl.

4. The compound of claim 1, wherein n is 1.

5. The compound of claim 1, wherein $R^{12D}$ is $C_{7-14}$ alkaryl, $C_{3-10}$ alkcycloalkyl, or $C_{3-10}$ alkheterocyclyl.

6. The compound of claim 5, wherein $R^{12D}$ is $C_{3-10}$ alkcycloalkyl.

7. The compound of claim 1, wherein each of $R^{12E}$ and $R^{12F}$ is, independently, H, $C_{7-14}$ alkaryl, $C_{3-10}$ alkcycloalkyl, or $C_{3-10}$ alkheterocyclyl.

8. The compound of claim 7, wherein each of $R^{12E}$ and $R^{12F}$ is, independently, H or $C_{7-14}$ alkaryl.

9. The compound of claim 1, wherein $R^{12D}$ is $C_{3-10}$ alkcycloalkyl, $R^{12E}$ is H, and $R^{12F}$ is $C_{7-14}$ alkaryl.

10. A pharmaceutical composition comprising the compound of claim 1 and a pharmaceutically acceptable excipient.

11. The pharmaceutical composition of claim 10, wherein the pharmaceutical composition is formulated for intraarticular, oral, parenteral, intravenous, intramuscular, rectal, cutaneous, subcutaneous, topical, transdermal, sublingual, nasal, vaginal, intravesicular, intraurethral, intrathecal, epidural, aural, or ocular administration to a human patient.

12. A method of treating a neurogenic inflammatory disorder in a human patient, the method comprising administering a therapeutically effective amount of the compound of claim 1 to the patient.

13. The method of claim 12, wherein the neurogenic inflammatory disorder is selected from asthma, rhinitis, conjunctivitis, arthritis, colitis, contact dermatitis, pancreatitis, chronic cough, diabetes, rheumatic disease, eczema, cystitis, gastritis, urethritis, migraine headache, psoriasis, sinusitis, chronic rhinosinusitis, traumatic brain injury, sepsis, polymicrobial sepsis, tendinopathy, chronic urticaria, rosacea, sunburn, inhaled tear gases, acute lung injury, inhalation of irritants, inhalation of pollutants, and exposure to chemical warfare agents.

14. The method of claim 12, wherein the compound is formulated for intraarticular, oral, parenteral, intravenous, intramuscular, rectal, cutaneous, subcutaneous, topical, transdermal, sublingual, nasal, vaginal, intravesicular, intraurethral, intrathecal, epidural, aural, or ocular administration to the patient.

15. A compound having the following structure:

wherein X is any pharmaceutically acceptable anion.

16. A pharmaceutical composition comprising the compound of claim 15 and a pharmaceutically acceptable excipient.

17. The pharmaceutical composition of claim 16, wherein the pharmaceutical composition is formulated for intraarticular, oral, parenteral, intravenous, intramuscular, rectal, cutaneous, subcutaneous, topical, transdermal, sublingual, nasal, vaginal, intravesicular, intraurethral, intrathecal, epidural, aural, or ocular administration to a human patient.

18. A method of treating a neurogenic inflammatory disorder in a human patient, the method comprising administering a therapeutically effective amount of the compound of claim 15 to the patient.

19. The method of claim 18, wherein the neurogenic inflammatory disorder is selected from asthma, rhinitis, conjunctivitis, arthritis, colitis, contact dermatitis, pancreatitis, chronic cough, diabetes, rheumatic disease, eczema, cystitis, gastritis, urethritis, migraine headache, psoriasis, sinusitis, chronic rhinosinusitis, traumatic brain injury, sepsis, polymicrobial sepsis, tendinopathy, chronic urticaria, rosacea, sunburn, inhaled tear gases, acute lung injury, inhalation of irritants, inhalation of pollutants, and exposure to chemical warfare agents.

20. The method of claim 18, wherein the compound is formulated for intraarticular, oral, parenteral, intravenous, intramuscular, rectal, cutaneous, subcutaneous, topical, transdermal, sublingual, nasal, vaginal, intravesicular, intraurethral, intrathecal, epidural, aural, or ocular administration to the patient.

21. The compound of claim 15, wherein X is Br, Cl, or I.

22. The pharmaceutical composition of claim 16, wherein the pharmaceutical composition is formulated for administration to the patient by way of injection, inhalation, or direct contact with the nasal, genitourinary, gastrointestinal, reproductive, or oral mucosa of the patient.

23. The method of claim 18, wherein the compound is formulated for administration to the patient by way of injection, inhalation, or direct contact with the nasal, genitourinary, gastrointestinal, reproductive, or oral mucosa of the patient.

24. The pharmaceutical composition of claim 10, wherein the pharmaceutical composition is formulated for administration to the patient by way of injection, inhalation, or direct contact with the nasal, genitourinary, gastrointestinal, reproductive, or oral mucosa of the patient.

25. The method of claim 12, wherein the compound is formulated for administration to the patient by way of injection, inhalation, or direct contact with the nasal, genitourinary, gastrointestinal, reproductive, or oral mucosa of the patient.

* * * * *